(12) United States Patent
Paul et al.

(10) Patent No.: US 11,533,913 B2
(45) Date of Patent: Dec. 27, 2022

(54) TREATING WATER STRESS IN PLANTS

(71) Applicant: Rothamsted Research Limited, Hertfordshire (GB)

(72) Inventors: Matthew Jeremy Paul, Hertfordshire (GB); Cara Ashleigh Griffiths, Hertfordshire (GB)

(73) Assignee: Rothamsted Research Limited, Hertfordshire (GB)

( * ) Notice: Subject to any disclaimer, the term of this patent is extended or adjusted under 35 U.S.C. 154(b) by 0 days.

(21) Appl. No.: 15/741,557

(22) PCT Filed: Jul. 1, 2016

(86) PCT No.: PCT/GB2016/052011
§ 371 (c)(1),
(2) Date: Jan. 3, 2018

(87) PCT Pub. No.: WO2017/006095
PCT Pub. Date: Jan. 12, 2017

(65) Prior Publication Data
US 2018/0213793 A1 Aug. 2, 2018

(30) Foreign Application Priority Data
Jul. 3, 2015 (GB) .................................. 1511732

(51) Int. Cl.
*A01N 57/16* (2006.01)
*A01N 57/24* (2006.01)
*C07H 13/00* (2006.01)

(52) U.S. Cl.
CPC ............ *A01N 57/16* (2013.01); *A01N 57/24* (2013.01); *C07H 13/00* (2013.01)

(58) Field of Classification Search
None
See application file for complete search history.

(56) References Cited

U.S. PATENT DOCUMENTS

| 2003/0017947 A1* | 1/2003 | Kawai .................... A01N 43/16 504/292 |
| 2010/0024066 A1 | 1/2010 | Leyman et al. |
| 2014/0113820 A1 | 4/2014 | Sagar et al. |

FOREIGN PATENT DOCUMENTS

| CN | 101374952 | 2/2009 |
| CN | 103687490 A | 3/2014 |

(Continued)

OTHER PUBLICATIONS

Ali, Q., and M. Ashraf. "Induction of drought tolerance in maize (*Zea mays* L.) due to exogenous application of trehalose: growth, photosynthesis, water relations and oxidative defence mechanism." Journal of Agronomy and Crop Science 197.4 (2011): 258-271.*

(Continued)

*Primary Examiner* — Alton N Pryor
(74) *Attorney, Agent, or Firm* — Riverside Law LLP

(57) ABSTRACT

The present invention relates to methods and uses of photo-labile compounds which are trehalose-6-phosphate or trehalose-6-phosphonate or agriculturally acceptable salts thereof in the treatment of water stress in plants. The invention also concerns methods and the use of the compounds for resurrection of water stressed plants, and for improvement of yield of crop plants under water stressed conditions compared with untreated plants.

12 Claims, 32 Drawing Sheets

(56) References Cited

FOREIGN PATENT DOCUMENTS

| WO | 1997042326 | 11/1997 |
| WO | 2001052653 | 7/2001 |
| WO | 2005097551 | 10/2005 |
| WO | 2012146914 | 11/2012 |

OTHER PUBLICATIONS

Hao-Wen Li et al., 2011, "Overexpression of the trehalose-6-phosphate synthase geneenhances abiotic stress tolerance in rice", Planta, vol. 234, No. 5:pp. 1007-1018.

Ramon Suarez et al., 2008, "Improvement of Drought Tolerance and Grain Yield in Common Bean by Overexpressing Trehalose-6-Phosphate Synthase in Rhizobia", Molecular Plant-Microbe Interactions, vol. 21,No. 7:pp. 958-966.

Avonce et al., The *Arabidopsis*Trehalose-6-P Synthase AtTPS1 Gene Is a Regulator of Glucose, Abscisic Acid, and Stress Signaling, (2004) Plant Physiol. 136: 3649-3659.

Debast et al., Altering Trehalose-6-Phosphate Content in Transgenic Potato Tubers Affects Tuber Growth and Alters Responsiveness to Hormones during Sprouting, 2011, Plant Physiol. 156: 1754-1771.

Garg et al., Trehalose accumulation in rice plants confers high tolerance levels to different abiotic stresses, 2002, PNAS 99: 15898-15903.

Holmstrom et al., Drought tolerance in tobacco, 1996, Nature 379: 683-684.

Hu Huifang, et al., A Preliminary Study on Exogenous Trehalose to Improve Drought Resistance of Cucumber, Journal of Shenyang Agricultural University, 2008 pp. 83-85.

Jang et al., Expression of a Bifunctional Fusion of the *Escherichia coli* Genes for Trehalose-6-Phosphate Synthase and Trehalose-6-Phosphate Phosphatase in Transgenic Rice Plants Increases Trehalose Accumulation and Abiotic Stress Tolerance without Stunting Growth, 2003, Plant Physiol 131: 516-524.

Karim et al., Improved drought tolerance without undesired side effects in transgenic plants producing trehalose, 2007, Plant Mol Biol 64: 371-386.

Lee et al., Accumulation of trehalose within transgenic chloroplasts confers drought tolerance, 2003, Mol Breeding 11: 1-13.

Romero et al., Expression of the yeast trehalose-6-phosphate synthase gene in transgenic tobacco plants: pleiotropic phenotypes include drought tolerance, 1997, Planta 201: 293-297.

Xiangli Xu, et al. Effects of Exogenous Trehalose on Drought Resistance of Tobacco Seedlings under Drought Stress, Journal of Anhui Agricultural Sciences, 2010 33:18675-18677.

\* cited by examiner

TREATING WATER STRESS IN PLANTS

CROSS-REFERENCE TO RELATED APPLICATIONS

This application is the U.S. national phase application filed under 35 U.S.C. § 371 claiming benefit to International Patent Application No. PCT/GB2016/052011, filed on Jul. 1, 2016, which claims priority to Great Britain provisional application no. 1511732.8, filed Jul. 3, 2015, the disclosures of which are incorporated herein by reference in their entirety.

FIELD OF THE INVENTION

The present invention relates to photo-labile compounds that increase the amount or concentration of Trehalose-6-Phosphate (T6P) in plants and methods and uses of these for treating water stress in a wide range of plant species. The invention also concerns methods and the use of the compounds for resurrection of water stressed plants, and for improvement of yield of crop plants under water stressed conditions compared with untreated plants.

BACKGROUND

Global crop yields must double in the next 35 years to meet projected demand for food (Ray et al., 2013, PLoS ONE 8, e66428; Grassini et al., 2013, Nat Commun 4, doi: 10.1038/ncomms3918). This requirement is coming at a time of unprecedented climatic variability (Lobell and Tebaldi, 2014, Environmental Research Letters 9, 074003). Current methods of crop improvement are not keeping pace with crop yield increases required (Ray et al., 2013, PLoS ONE 8, e66428).

This requirement for substantial increases in crop yields is set against a backdrop of a depletion of global water resources, increasing drought frequency (both moderate and severe) and increasing drought intensity (UN 2012). Water stress is already extremely common in plants and it is known to limit the productivity of all major crop species. For example, approximately 80% of agricultural land in the United States experiences drought annually (United States Department of Agriculture, Economic Research Service, 2012). Even seasonal mild or moderate water stress in critical growth stages can cause substantial yield reductions (10-20%) in systems with limited irrigation or those that rely solely on rainfall. As 80% of global agriculture takes place in rain-fed, rather than irrigated agricultural systems, with many of these systems experiencing extreme water scarcity, if the pressing need for step-changes in food production is to be met, increasing crop yields in water-limited environments must be prioritised. Therefore, a continuing need exists for the development of novel strategies to address plant water stress in the field.

The trehalose pathway has long been implicated in water stress and has previously been targeted using approaches founded on genetic modification (for example, see WO 97/42326). However, GM approaches targeting the trehalose pathway have yielded a rather confused picture in relation to T6P and drought tolerance. Some experiments which targeted the Trehalose pathway indicated that transgenic approaches, resulting in increased T6P levels in plants conferred drought resistance on model plants including *Arabidopsis*, rice and potato (Holmstrom et al., 1996, Nature 379: 683-684; Romero et al., 1997, Planta 201: 293-297; Lee et al., 2003, Mol Breeding 11: 1-13; Karim et al., 2007, Plant Mol Biol 64: 371-386; Miranda et al., 2007, Planta 226: 1411-1421; Garg et al., 2002, PNAS 99: 15898-15903; Jang et al., 2003, Plant Physiol 131: 516-524; Li et al., 2011, Planta 234: 1007-1018)

Additionally, genetic manipulation of this pathway has been shown to have a range of other, pleiotropic effects unrelated to water stress, for example altering responsiveness to hormones during sprouting (Debast et al., 2011, Plant Physiol. 156: 1754-1771) and many plants with alterations in trehalose levels show developmental defects and severely aberrant morphological phenotypes such as stunted growth, reduced seed number, sterility, abnormal root development and lancet-shaped leaves (reviewed in Avonce et al., (2004) Plant Physiol. 136: 3649-3659).

Any role of trehalose in conferring resistance to water stress is unclear. Whilst genetic modification (GM) allows some approaches (Campos et al., 2004, Field Crops Res 90: 19-34) it has temporal and strategic limitations and is not accepted as an approach across the globe (especially in Europe).

WO2012/146914 ISIS Innovation Limited discloses photo-labile Trehalose-6-Phosphate and phosphonate precursors, and agriculturally acceptable salts thereof and describes methods and uses of these compounds for increasing starch production in plants.

The present invention is based on a surprising discovery that application of T6P precursor compounds to plants during water stress and prior to alleviation of water stress by watering, results in dramatic improvements in subsequent plant growth compared with non-treated control plants.

Plant water stress, often a consequence of drought, can have major impacts on plant growth and development which can ultimately result in significant reductions in crop yield or in extreme cases complete crop failure. A practical application of the discovery of the invention is an ability to chemically trigger plant resistance to water stress and in doing so improve plant productivity under water-limited conditions, for example to increase yield from a crop species experiencing water shortage during any stage of vegetative growth.

SUMMARY OF THE INVENTION

Accordingly, the present invention provides the use of a compound of formula (I), a phosphonate analogue thereof, or agriculturally acceptable salts thereof:

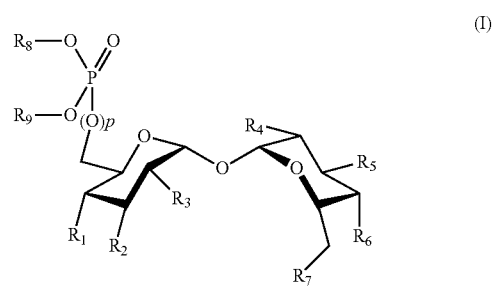

wherein;
p is 0 or 1;
$R_1$ to $R_7$ independently represent F, $N_3$, NR'R", $C_{1-4}$ alkyl, —($C_{1-4}$ alkyl)OH or OH, wherein R' and R" independently represent hydrogen or $C_{1-4}$ alkyl;

and $R_8$ and $R_9$ are the same or different and represent H or a photo-labile protecting group, wherein at least one of $R_8$ and $R_9$ represents a photo-labile protecting group;
as a treatment for a water stressed plant. The compounds defined herein are therefore used for treating water stress in plants.

The photo-labile protecting group may be of formula (II):

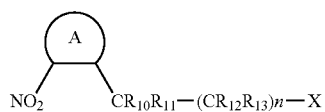

(II)

wherein;
ring A represents an aryl or heterocyclic group;
either (i) $R_{10}$ and $R_{11}$ are the same or different and are selected from hydrogen, $C_{1-4}$ alkyl which is unsubstituted or substituted with one or more halogen atoms, —OR', halogen, —NR'R" or —$CO_2R'$, wherein R' and R" are independently selected from hydrogen and $C_{1-4}$ alkyl, or (ii) two $R_{10}$ groups on adjacent photo-labile protecting groups together form a bond and $R_{11}$ represents hydrogen, $C_{1-4}$ alkyl which is unsubstituted or substituted with one or more halogen atoms, —OR', halogen, —NR'R" or —$CO_2R'$, wherein R' and R" are independently selected from hydrogen and $C_{1-4}$ alkyl;
n is 0 or 1; and $R_{12}$ and $R_{13}$ are the same or different and are selected from hydrogen, $C_{1-4}$ alkyl which is unsubstituted or substituted with one or more halogen atoms, —OR', halogen, —NR'R" or —$CO_2R'$, wherein R' and R" are independently selected from hydrogen and Cu alkyl; wherein X represents the link to the remainder of the compound of formula (I).

The photo-labile group may be selected from;

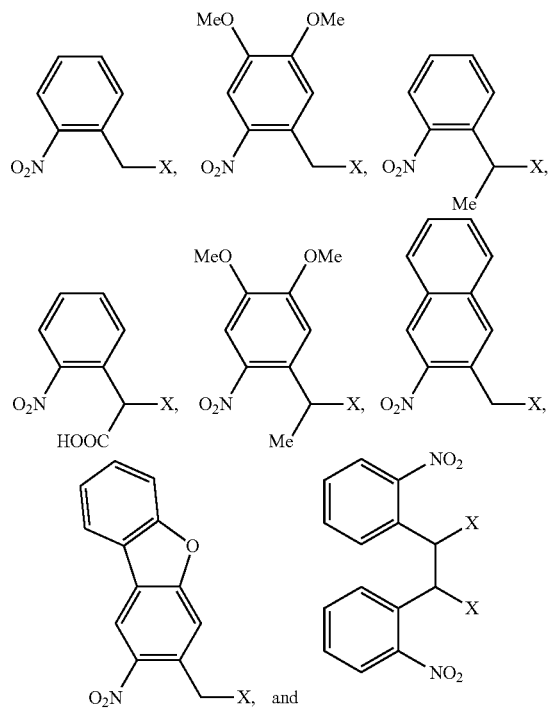

wherein X represents the link to the remainder of the compound of formula (I).

The photo-labile protecting group may be of formula (III):

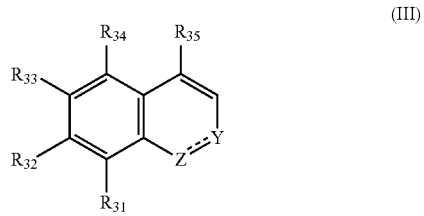

(III)

wherein;
either Z represents N, Y represents $CR_{36}$ and Z and Y are linked by a double bond; or Z represents O, Y represents C=O and Z and Y are linked by a single bond;
$R_{36}$ represents —$CR_{37}R_{38}X$;
when Y represents $CR_{36}$, $R_{35}$ represents hydrogen, and when Y represents C=O, $R_{35}$ represents —$CR_{37}R_{38}X$;
either (i) $R_{37}$ and $R_{36}$ are the same or different and are selected from hydrogen, Cu alkyl which is unsubstituted or substituted with one or more halogen atoms, —OR', halogen, —NR'R" or —$CO_2R'$, wherein R' and R" are independently selected from hydrogen and $C_{1-4}$ alkyl, or (ii) two $R_{37}$ groups on adjacent photolabile protecting groups together form a bond and $R_{38}$ represents hydrogen, $C_{1-4}$ alkyl which is unsubstituted or substituted with one or more halogen atoms, —OR', halogen, —NR'R" or —$CO_2R'$ wherein R' and R" are independently selected from hydrogen and C alkyl;
$R_{32}$ represents —OR', —NR'R", —$O(C_{1-4}$ alkyl)-COOR', —$O(C_{1-4}$ alkyl)-OR' or —$O(C_{1-4}$alkyl)-NR'R", wherein R' and R" independently represent hydrogen or $C_{1-4}$ alkyl; and
$R_{31}$, $R_{33}$ and $R_{34}$ are independently selected from hydrogen, halogen, —OR', —NR'R", —$O(C_{1-4}$alkyl)-COOR', —$O(C_{1-4}$ alkyl)-OR' or —$O(C_{1-4}$ alkyl)-NR'R", wherein R' and R" independently represent hydrogen or $C_{1-4}$ alkyl;
wherein X represents the link to the remainder of the compound of formula (I).

The photo-labile protecting group may be selected from:

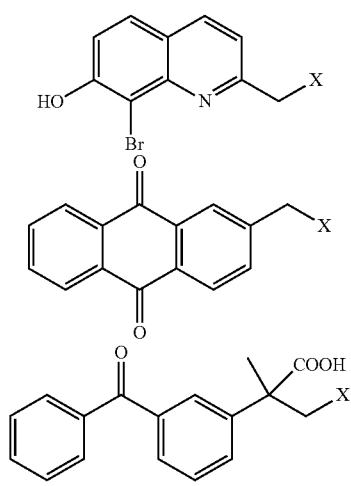

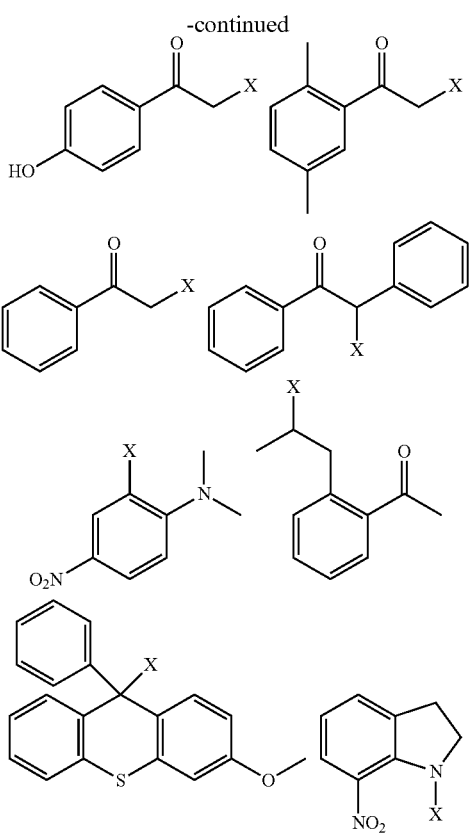

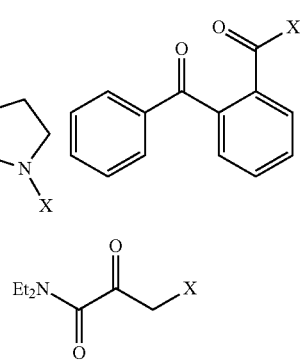

The present invention also provides the use of such a compound, wherein the photo-labile protecting group is of formula (II) and ring A represents a $C_{6-10}$ aryl group or a 5- to 14-membered heterocyclic group containing one or more atoms selected from N, O and S, wherein the aryl or heterocyclic group is unsubstituted or substituted with one or more substituents selected from $C_{1-4}$ alkyl, —OR', halogen, CN, —NR'R", —COOR', —($C_{1-4}$ alkyl)COOR' and —O($C_{1-4}$alkyl)COOR', wherein R' and R" are independently selected from hydrogen and $C_{1-4}$ alkyl, or wherein two adjacent substituents on the aryl or heterocyclic group together form a 5- or 6-membered heterocyclic ring containing one or more heteroatoms selected from N, O or S.

The photo-labile protecting group may be of formula (II) and ring A represents a phenyl, naphthalenyl or dibenzofuranyl ring.

The photo-labile protecting group may be of formula (IIa):

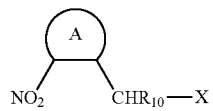

wherein;
ring A represents an unsubstituted or substituted group selected from phenyl, naphthyl or dibenzofuranyl, wherein a substituted phenyl, naphthyl or dibenzofuranyl group is a phenyl, naphthyl or dibenzofuranyl group having one or two methoxy substituents, or a phenyl, naphthyl or dibenzofuranyl group wherein two adjacent ring positions are substituted with a —$CH_2$—O—$CH_2$— moiety; and $R_{10}$ represents hydrogen, methyl, —CF3 or —COOH;
wherein X represents the link to the remainder of the compound of formula (I).

The photo-labile protecting group may be of formula (IIIa):

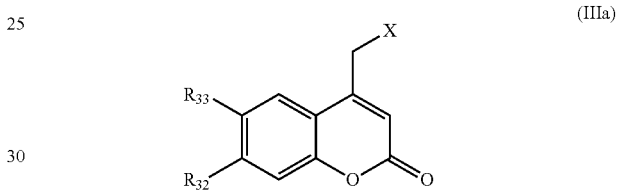

wherein;
$R_{32}$ represents —OR', —NR'R" or —O($C_{1-4}$alkyl)-COOR', wherein R' and R" independently represent hydrogen or $C_{1-2}$alkyl; and
$R_{33}$ represents hydrogen, Br, —OR', —NR'R" or —O($C_{1-4}$alkyl)-COOR', wherein R' and R" independently represent hydrogen or $C_{1-2}$ alkyl;
wherein X represents the link to the remainder of the compound of formula (I). Preferably, $R_{33}$ represents H and $R_{32}$ represents OMe, $NMe_2$, $NEt_2$ or —$OCH_2COOH$. Alternatively, $R_3$ may represent Br and $R_{32}$ may represent OH. Alternatively $R_3$ and $R_{32}$ may both represent —$OCH_2COOH$.

In accordance with the invention, $R_1$ to $R_7$ may represent hydroxyl.

In accordance with the invention, p may be 1.

Any of the compounds as described herein may be prepared in accordance with WO2012/146914 ISIS Innovations, incorporated herein by reference.

The present invention also provides a method of treating a water stressed plant, comprising treating the plant with a compound as hereinbefore defined.

The present invention also provides a method of resurrecting a plant experiencing water stress, wherein the method comprises treating the plant with a compound as hereinbefore defined.

In the following, the variously recited technical aspects of the methods of the invention apply equally to the claimed uses of the compounds hereinbefore defined.

In methods of the invention whether for alleviation of water stress in a plant or for resurrecting a plant experiencing acute water stress, the methods preferably comprise treating the plant in the vegetative growth phase; in other words at any time or period prior to anthesis.

The stages of plant shoot development are well characterised and morphological and anatomical traits that change in coordinated manner at predictable times in vegetative development are established for the majority of species. Vegetative growth phase or vegetative phase is therefore well known in the art and refers to the period of growth between germination and flowering, which terminates with the onset of the reproductive phase whereupon the plant acquires the capacity to produce structures required for sexual reproduction.

Most practically, this may be determined visually or alternatively relative to a characteristic profile of molecular markers defining the various phases of the plant life cycle; including for instance, but not limited to; a decrease in miR156, and miR157 expression or an increase in the expression of *squamosa* promoter binding protein/SBP-like (SBP/SPL) transcription factors which are known to regulate a variety of processes in shoot development, including inflorescence development and flowering time. In wheat plants for example, the vegetative phase is characterised by growth and leaf initiation and ends with spikelet initiation and floral initiation (reviewed in Sadras and Calderini, 2015, Crop Physiology: Applications for Genetic Improvement and Agronomy, $2^{nd}$ Ed., Elsevier).

Water stress refers to a situation where less water is available than is demanded by the plant tissues. Water stress may be continuous or discontinuous. The magnitude or severity of the stress in a plant may vary over time or as between different species or individuals at a particular time point, for example in a field of crop plants.

Several practical techniques for accurate measurement of plant water stress at tissue, individual plant and field scale are well known in the art. Usefully, at leaf level, water stress may be accurately estimated by measurement of plant water potential, which may be obtained by determining the negative pressure (tension) within the leaf. This may be achieved, for example, by excision and placement of a leaf from a plant into a sealed chamber, adding compressed gas to the chamber and recording the pressure at which water appears at surface of the cut end of the leaf.

At the whole plant level, canopy temperature has been widely used for many years to detect the onset and duration of plant water stress (Tanner, 1963; Weigand and Namken, 1966; Ehrler and van Bavel, 1967; Astin and van Bavel, 1972; Bartholic et al, 1972; and Ehrler, 1973). With the development of remote sensing and infra-red thermography techniques, canopy temperature has subsequently been demonstrated to be an effective method of field scale evaluation of crop water status at or near real-time.

Several commercially available tools exist for the measurement of plant water stress, for example the Plant Water Status Console (http://www.soilmoisture.com/letthe/) (Soilmoisture Equipment Corp., 801 S. Kellogg Ave., Goleta, Santa Barbara, Calif.).

Other measures of plant water stress may include, but are not limited to leaf temperature at the individual plant level or canopy temperature at the field scale (reviewed in Jackson et al., Water Resources Research 4: 1133-1138) whether alone or in combination with wet- and dry-bulb air temperatures and estimates of net radiation (crop water stress index); stem water potential, leaf water potential, xylem pressure potential, stomatal conductance. Reflectance at 970 nm measured using thermal infra-red spectroscopy has also been demonstrated, for example using a silicon-diode spectrometer. Measurements may also be species specific, for example the use of midday stem water potential (Naor, 2000, Acta Hortic. (ISHS) 537: 447-454) or diurnal trunk shrinkage in fruit trees (Intrigliolo and Castel, 2005, Tree Physiology 26: 303-311).

Preferably, the method, whether for resurrection of acutely water stressed plants or for alleviation of water stress, the method comprises treating the plant with the compound at least 24 hours prior to re-watering. A lesser period of time may also be used e.g. at least 8, at least 12 or at least 18 hours. Optionally, the plant may be treated at least 24, 25, 26, 27, 28, 29, 30, 31, 32, 33, 34, 35 or 36 hours prior to re-watering. Longer periods of time before re-watering fall within the scope of the invention e.g. a number of days selected from and including 2, 3, 4, 5, 6, 7, 8, 9, 10, 11, 12, 13 or 14 days. Typically, the plant is treated with one or more compounds in the range 24 to 336 hours prior to re-watering, optionally in the range 24 to 312, 24 to 288, 24 to 264, 24 to 240, 24 to 216, 24 to 192, 24 to 336, 24 to 168, 24 to 144, 24 to 72, 24 to 48, 24 to 36, 24 to 35, 24 to 34, 24 to 33, 24 to 32, 24 to 31, 24 to 30, 24 to 29, 24 to 28, 24 to 27, 24 to 26 or 24 to 25 hours prior to re-watering.

Preferably, the methods and uses of the invention comprise treating the plant with the compound wherein the plant is under water stress for a period falling in the range 8 hours to 10 days. Accordingly, the plant may be treated for example at least 8, at least 9, at least 10, at least 12 or at least 18 hours after the onset of water stress, however in normal circumstances, for example in the field, water stress typically remains undetected before 24 hours after the onset of stress. Commonly, the plant may be treated with one or more compounds from the period commencing after at least 24 hours of water stress until the point at which plant death occurs and recovery is no longer possible. Typically, the plant is treated with one or more compounds in the range 24 hours to 10 days after onset of water stress. Commonly the plant may be treated at least 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71 or 72 hours after the onset of water stress. Plants may be treated with the compounds following longer periods of water stress being a number of days selected from and including 5, 6, 7, 8, 9, 10, 11, 12, 13 or 14 days.

Typically, the plant is treated with one or more compounds in the range 8 to 336 hours after water stress, optionally in the range 10 to 336, 12 to 336, 18 to 336, 24 to 336, 24 to 312, 24 to 288, 24 to 264, 24 to 240, 24 to 216, 24 to 192, 24 to 336, 24 to 168, 24 to 144, 24 to 72, 24 to 48, 24 to 36, 24 to 35, 24 to 34, 24 to 33, 24 to 32, 24 to 31, 24 to 30, 24 to 29, 24 to 28, 24 to 27, 24 to 26 or 24 to 25 hours after the onset of water stress.

In methods and uses relating to the resurrection of plants experiencing acute water stress, the period of water stress may be one selected from 48 hours or more. Also a period selected from a number of days being 3, 4, 5, 6, 7, 8, 9, 10, 11, 12, 13 or 14 days.

In methods and uses of the invention, any of the compounds may be applied alone or in conjunction with other compounds. In particular, the compounds may commonly be applied together with at least one fertilizer, fungicide, herbicide, insecticide or plant growth regulator whether separately, sequentially or simultaneously.

Preferably, methods of the invention alleviate the effects of water stress on plants. Preferably application of any of the compounds disclosed herein results in a plant having increased yield compared with untreated plants.

Accordingly, in a further aspect, the present invention provides a method of improving crop yield of field grown crops, comprising treating the growing crop in vegetative phase prior to flowering with a compound as hereinbefore defined. An increased yield may refer to vegetative or reproductive parts of the plant, depending on the crop and whether biomass, harvest index or seed number or seed size is desired. In preferred embodiments, the size and/or number of seeds or grain produced by a plant treated in accordance with the methods of the invention is increased relative to untreated control plants or plant material that has endured the water stressed condition. Most preferably, the size and number of seeds produced by plants treated in accordance with methods of the invention is increased relative to untreated equivalent plants.

In accordance with all aspects of the present invention, the compounds disclosed herein may be used to treat any plant species, which may be monocots or dicots. The compounds disclosed herein may preferably be used to treat those plants which are typically exploited for grain or biomass production, exhibit high growth rates and are easily grown and harvested. In particular preferred plants include those which grow naturally or are cultivated in arid environments and/or those with high temperatures, low humidity, high vapour pressure deficits or receiving low quantities of water (rainfall and/or irrigation) relative to their water demand and water use efficiency (WUE). The compounds disclosed herein may usefully alleviate water stress in plants whether severe, moderate, mild, continuous or intermittent. The compounds disclosed herein may be used to resurrect those plants experiencing severe water stress, which would have otherwise died if left untreated (or if treated by re-watering alone).

In use, the compounds disclosed herein are usually applied directly onto the surface of the plant or crop. Typically, this may be achieved by direct application to the plant or crop, for example by spraying the compound or mixture of compounds directly onto the plant material, for example onto leaves, stems or roots of the plant during vegetative phase although other equally feasible methods of application will be known in the art. It is envisaged that the compounds disclosed herein may also be applied indirectly to the medium (e.g. soil or water) in which the plants or crop are grown.

Treatment of the plants in accordance with the methods of the invention may involve a single application of the compound either to the plant or to the growth medium. However, it will be understood that treatment may alternatively involve multiple applications of the same compound or indeed combinations of the compounds disclosed herein. Where multiple (i.e. two or more) different compounds are applied to the same crop, these may be applied simultaneously, separately (in any order) or sequentially.

The compounds disclosed herein are typically provided to the plant or crop in the form of an aqueous solution. However, the compounds disclosed herein may also be provided to the plant or crop in solid form such as a powder, dust or in granular form and combinations thereof.

Where the compounds disclosed herein are provided as an aqueous solution, normally the solution applied to the plant or growth medium will have a final compound concentration in the range 0.1 to 10 mM, optionally in the range 0.1 mM to 1 M, 0.1 to 900 mM, 0.1 to 800 mM, 0.1 to 700 mM, 0.1 to 600 mM, 0.1 to 500 mM, 0.1 to 400 mM, 0.1 to 300 mM, 0.1 to 200 mM, 0.1 to 100 mM, 0.1 to 50 mM, 0.1 to 40 mM, 0.1 to 30 mM, 0.1 to 20 mM, 0.1 to 10 mM, 0.1 to 9 mM, 0.1 to 8 mM, 0.1 to 7 mM, 0.1 to 6 mM, 0.1 to 5 mM, 0.1 to 4 mM, 0.1 to 3 mM, 0.1 to 2 mM or 0.1 to 1 mM. Optionally, the compounds disclosed herein may be applied at a final concentration of 1 mM, 2 mM, 3 mM, 4 mM, 5 mM, 6 mM, 7 mM, 8 mM, 9 mM, 10 mM, 11 mM, 12 mM, 13 mM, 14 mM, 15 mM, 16 mM, 17 mM, 18 mM, 19 mM, 20 mM, 21 mM, 22 mM, 23 mM, 24 mM, 25 mM, 26 mM, 27 mM, 28 mM, 29 mM, 30 mM, 31 mM, 32 mM, 33 mM, 34 mM, 35 mM, 36 mM, 37 mM, 38 mM, 39 mM, 40 mM, 41 mM, 42 mM, 43 mM, 44 mM, 45 mM, 46 mM, 47 mM, 48 mM, 49 mM, 50 mM, 51 mM, 52 mM, 53 mM, 54 mM, 55 mM, 56 mM, 57 mM, 58 mM, 59 mM, 60 mM, 61 mM, 62 mM, 63 mM, 64 mM, 65 mM, 66 mM, 67 mM, 68 mM, 69 mM, 70 mM, 71 mM, 72 mM, 73 mM, 74 mM, 75 mM, 76 mM, 77 mM, 78 mM, 79 mM, 80 mM, 81 mM, 82 mM, 83 mM, 84 mM, 85 mM, 86 mM, 87 mM, 88 mM, 89 mM, 90 mM, 91 mM, 92 mM, 93 mM, 94 mM, 95 mM, 96 mM, 97 mM, 98 mM, 99 mM, 100 mM. Preferably, the compounds disclosed herein are applied at a final concentration of 0.1 mM, 0.2 mM, 0.3 mM, 0.4 mM, 0.5 mM, 0.6 mM, 0.7 mM, 0.8 mM, 0.9 mM, 1 mM, 1.1 mM, 1.2 mM, 1.3 mM, 1.4 mM, 1.5 mM, 1.6 mM, 1.7 mM, 1.8 mM, 1.9 mM or 2 mM. More preferably the compounds disclosed herein are applied at a final concentration of 1 mM.

The present invention provides the use of a composition comprising any of the compounds disclosed herein (and combinations thereof) or an agriculturally acceptable salt thereof in treating a water stressed plant. Accordingly, the compounds disclosed herein and agriculturally acceptable salts thereof are preferably to be applied to the plant or growth medium as an aqueous solution.

In embodiments where the compound may be applied to plants as a powder or dust, the compounds disclosed herein may be provided alone or in combination with other compounds disclosed herein and/or together with an unreactive solid carrier and/or a surfactant, for example a wetting agent. A suitable inert solid carrier may be selected from but not limited to the group comprising clays (for example attapulgite, kaolin or montmorillonite), purified or finely divided silicates and/or diatomaceous earth. Suitable surfactants may be ionic or non-ionic and have dispersing, penetrating or wetting abilities. Commonly, these surfactants may include alkylbenzenesulfonates, alkyl sulfates, sulfonated lignins, naphthalenesulfonates, condensed naphthalenesulfonates and non-ionic surfactants such as products of condensation of ethylene oxide with alkylphenols. Such surfactants may typically comprise 0.5 to 10 percent by weight of the final product for application to the plant or medium.

Solid compositions such as powders containing a compound of the invention preferably contain at least 0.1%, e.g. from 0.1 to 95% by weight of the compound of the invention and from 0.1 to 75% of an inert carrier or surfactant.

When plants are treated with any of the compounds disclosed herein by indirect application, for instance to the growth medium or soil rather than directly onto the plant surface it may be found that dusts or granular formulations are most practical. Common granular formulations may include, but are not limited to any of the compounds disclosed herein, either alone or in combination, dispersed (for instance by spraying) on an inert carrier such as coarsely ground clay.

For convenience, compounds disclosed herein may be combined with other active ingredients used for the treatment of plants, for example they may be incorporated into other agrochemical products such as fertilisers, herbicides, anti-bacterial or anti-fungal agents and/or pesticides.

Appropriate recipient plants may include grasses, trees, crops, shrubs, vegetables and ornamentals. More particularly, plants suitable for treatment with compounds disclosed herein in the present invention are those which produce a high yield of grain for food, feedstock or biomass for fuel or paper production. Examples of suitable plant types include but are not limited to fast growing crops, for example wheat, soybean, alfalfa, corn, rice, maize, sorghum, panicum oat, sugar cane and sugar beet. Preferably, the plant is a cereal crop selected from the genera *Triticum, Zea, Oryza, Hordeum, Sorghum, Panicum, Avena, Saccharum* or *Secale*. More preferably the plant is a *Triticum* sp. plant. Even more preferably the plant is a *Triticum aestivum* plant.

Other appropriate plants may include those plants which have a high water demand and/or are used for biofuel or cellulose production, for example trees, shrubs and grasses. Preferred trees for use in the invention include poplar, hybrid poplar, willow, silver maple, sycamore, sweetgum and *eucalyptus*. Preferred herbaceous plants include tobacco. Perennial grasses include switchgrass (*Panicum virgatum*), prairie Cordgrass (*Spartina* sp.), reed canary grass (*Phalaris arundinacea*), purple false brome (*Brachypodium distachyon*) and *Miscanthus* sp.

Commonly said recipient plant may also be selected from: poplar; *eucalyptus*; Douglas fir; pine; walnut; ash; birch; oak; teak; spruce. Preferably said plant is used typically as a crop, whether for food or other purposes. In preferred aspects of the invention said plant may be selected from: corn (*Zea mays*), canola (*Brassica napus, Brassica rapa* ssp.), flax (*Linum usitatissimum*), alfalfa (*Medicago sativa*), rice (*Oryza sativa*), rye (*Secale cerale*), sorghum (*Sorghum bicolor, Sorghum vulgare*), sunflower (*Helianthus annuas*), wheat (*Tritium aestivum*), soybean (*Glycine max*), tobacco (*Nicotiana tabacum*), potato (*Solanum tuberosum*), peanuts (*Arachis hypogaea*), cotton (*Gossypium hirsutum*), sweet potato (*Iopmoea batatus*), cassava (*Manihot esculenta*), coffee (*Cofea* spp.), coconut (*Cocos nucifera*), pineapple (*Anana comosus*), citrus tree (*Citrus* spp.) cocoa (*Theobroma cacao*), tea (*Camellia senensis*), banana (*Musa* spp.), avocado (*Persea americana*), fig (*Ficus casica*), guava (*Psidium guajava*), mango (*Mangifer indica*), olive (*Olea europaea*), papaya (*Carica papaya*), cashew (*Anacardium occidentale*), macadamia (*Macadamia intergrifolia*), almond (*Prunus amygdalus*), sugar beet (*Beta vulgaris*), oat (*Avena* sp.) or barley (*Hordeum vulgare*).

Additionally, the compounds of the invention may be used to treat water stress in vegetables and ornamental plants depending on the application chosen, and in particular those with commercial value, whether because they produce an edible crop (e.g. roots, tubers, stems, leaves, flowers, fruits, seeds) and/or for their aesthetic appearance (e.g. flowers, leaves, scent, fruit, stems, bark, or combination thereof). Accordingly, the recipient plant may also be selected from, for example: Parsnips, Radishes, Carrots, Beets, Daikon, Turnip, Celeriac, Rutabaga, Jicama, Asparagus, Celery, Rhubarb, Hearts of Palm, Bamboo Shoots, Broccoli, Ginger, Potato, Taro, Nopales, Rabe, Radicchio, Turnip, Spinach, Lettuce, Cabbage, Rocket, Swiss Chard, Napa, Cabbage, Bok Choy, Kale, Collard Greens, Leek Beet Greens, Artichoke, Broccoli, Cauliflower, Calendula, Squash Blossoms, Acorn Squash, Bell Pepper, Eggplant, Cucumber, Squash, Tomato, Tomatillo, Zucchini, Sweet Corn, Chili Pepper, Melons, Orange, Tangerine, Lime, Lemon, Grapefruit, Berries, Pears, Apples, Cherries, Peaches, Sunflower Seeds, Fava beans, French beans, Runner beans, Pigeon Peas, Snow Pea, Snap Peas, Sugar Peas, Peas, Almonds, Walnuts, Pecans or Peanuts.

Examples of ornamental plants include but are not limited to; *Acacia, Achillea*, African Boxwood, African Lily, African Violet, *Agapanthus, Ageratum, Ageratum houstonim, Allium, Alpina, Alstroemeria, Amaranthus hypochondriacus, Amaryllis, Ammi majus, Anconitum, Anemone, Anigozanthus*, Annual *Delphinium*, Anthurium, Antirrhinum *majus, Asparagus, Aster, Aster* spp., *Astilbe, Azalea*, Baby's Breath, Bachelor's Button, *Banksia, Begonia*, Bellflower; Bells of Ireland, Big Flax, Billy Buttons, Blazing Star; Bleeding Heart, *Boronia, Bouvardia*, Broom, *Buddleia, Bupleurum*, Butterfly Bush, Butterfly Orchid, California Pepperberry, Calla Lily, Campanul, Candytuft, Canterbury Bells, Carnation, *Carthamus, Caspia, Cattleya, Celosia, Celosia argenta, Centaurea cyanus, Chamelaucium*, Chimney Bells, *Chrysanthemum, Chrysanthemum×morifolium, Clarkia, Consolida ambigua, Convallaria*, Coral Bell, *Cordyline, Coreopsis*, Cornflower, *Craspedia*; Curly Willow, *Cyclamen, Cymbidium, Cymbidium* Orchid, Daffodil, Daisy, Daisy Mums, Daylily, *Delphinium, Dendrobium, Dendrobium* Orchid, *Dianthus barbatus, Dianthus caryophyllus, Dianthus caryophyllus nana*, Dragon's Tongue, Drumstick, *Enthusiasm, Erica* spp, *Eustoma grandiflorum*, False Bird of Paradise, False Spirea, Farewell-To-Spring, Flamingo Flower, Floss Flower, *Freesia, Freesia×hybrida*, Fuji or spider Mums, Gay Feather, *Genista* spp., *Geranium, Gerbera, Gerbera* spp., Ginger, *Gladiolus, Gladiolus* hybrid *nanus*, Goat's Beard, Godetia, Golden Rod, Guersney Lily, Gyp, *Gypsophila paniculata*, Heather, *Helianthus annuus, Heliconia* spp., *Hippeastrum, Hosta, Hydrangea, Iberis amara*; Impatiens; Inca Lily, Iris, Iris spp., Ivory Lily, Jade plant, Japhette Orchid, Jonquil, Kalanchoe, Kangaroo Paw, napweed, Larkspur, *Lathyrus odoratus, Lavandula*, Lavender, *Liatris*, Lilac, *Lilium* spp., Lilly-of-the-Valley, Lily, Lily of the Field, Lily of the Nile, *Limonium, Limonium* spp., Lisianthus, Lobster Claw, Love in the mist, Love-lies-bleeding, *Mattholia incana*, Memosa, Minature Carnation, Mini Carnation; Miniature *Gladiolus, Moluccella laevis*, Monkshood, Mother-in-law tongue, *Musa*, Myrsine, Myrtle, *Myrtus, Narcissus, Nephrolepis*, Nerine, Nerine Lily, *Nigella*; Orchid; Ornamental Onion; *Omithogalum, Paeonia*, Painted Tongue, Peony, Peruvian lily, *Petunia, Phalaenopsis, Philodendron, Phlox*, Pincushion Flower, Pitt, *Pittosporum*, Pixie Carnation; Pointsettia, *Polianthes tuberosa*, Pompon *Chrysanthemum*, Poppy Anemone; *Porium, Protea* spp.; Purple Coneflower, Pussy Willow, Queen Ann's Lace, *Ranunculus*, Rattlesnake, Red Ribbons, *Rosa* spp., Rose, *Rudbeckia*, Safflower, *Salix, Salvia, Sansevieria*, Satin Flowers, *Scabiosa, Schinus*, Sea lavender, *Sedum*, Shell Flowers, Snake Plant, Snapdragon, *Solidago, Solidaster* spp., Speedwell, Spider Lily, Spider Mums, Spray Carnation, Star of Bethlehem, Statice, Stenamezon, Stock, Summer's Darling, Sunflower, Sweet Pea, Sweet William, Sword Fern, *Syringa vulgaris*, Tailflowers, Tassel flower, Thouroughwax, Throatwort, *Trachelium*, Tree Fern, Trumpet Lily, Tuberose, Tulip, *Tulipa, Veronica*, Wattle, Waxflower, Wild Plantain, Windflower, Wolfsbane, Youth and Old Age, *Zantedeschia, Zinna, Zinnia elegans* or *Zygocactus*.

In the present invention, plants, plant material or plant part may refer to leaves, stems, roots, stalks, root tips, tissue or cells.

Plants, plant material or plant parts with "alleviated water stress" may refer to plants which lived where untreated plants would not. Plants may also demonstrate increased yield compared with untreated equivalent plants which may manifest itself, for example, as increases in biomass relative to untreated plants and/or increases or reductions in the number and/or size of seed produced by the plants relative to untreated plants or plant material.

BRIEF DESCRIPTION OF THE DRAWINGS

The invention will now be described in detail with reference to Examples and with reference to the accompanying drawings, in which.

DETAILED DESCRIPTION

Examples

Figure 1:
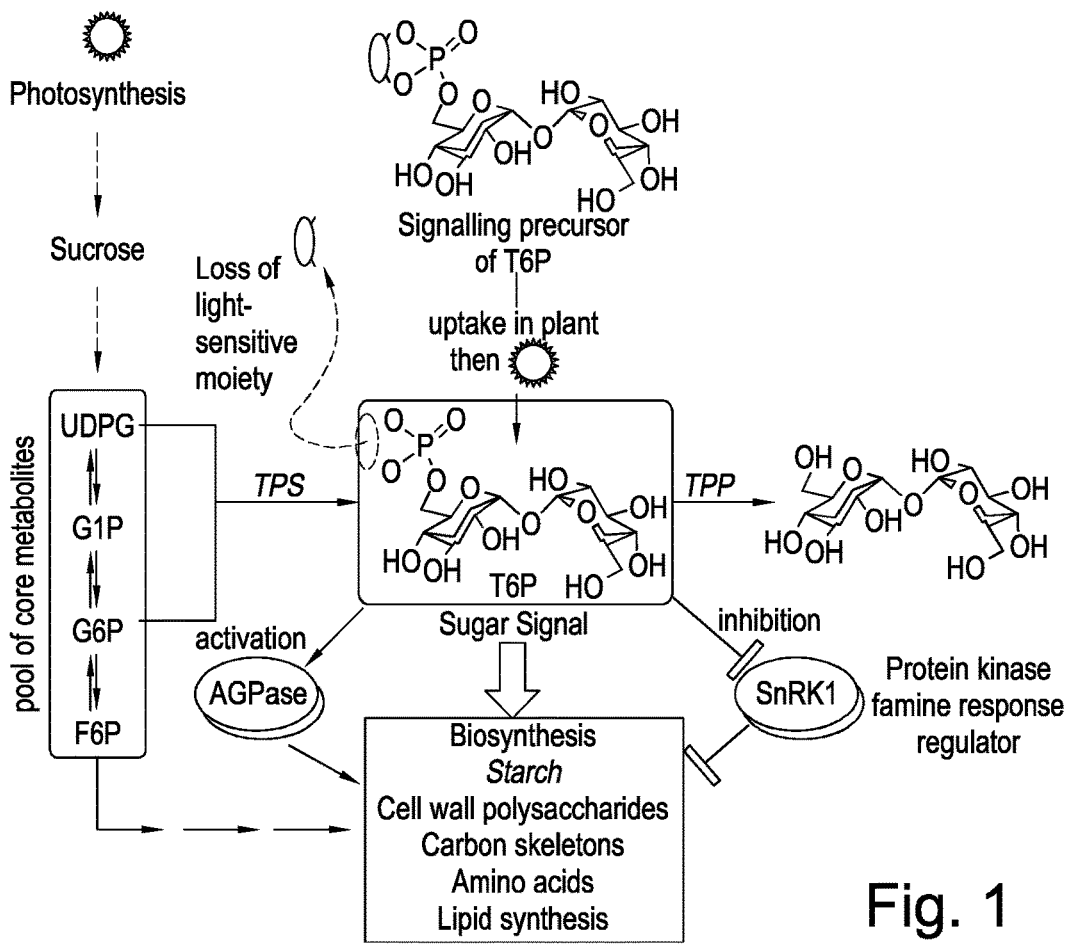
FIG. 1 shows a schematic diagram of a chemical strategy to control trehalose-6-phosphate (T6P) in plants.

The trehalose 6-phosphate (T6P) synthesis pathway in plants is summarized in FIG. 1. Photosynthesis generates sucrose, which is translocated to growing regions of the plant. Inside the cell it feeds a pool of core metabolites which are substrates for biosynthetic processes that determine growth and productivity. T6P is synthesised from UDPG and G6P by trehalose 6-phosphate synthase (TPS) and therefore reflects the abundance of sucrose. It is broken down by trehalose phosphate phosphatase (TPP). Increasing T6P (a) stimulates starch synthesis through posttranslational redox activation of ADP-glucose pyrophosphorylase (AGPase) which catalyzes the first committed step of starch biosynthesis and (b) inhibits SnRK1, a protein kinase central to energy conservation and survival during energy deprivation. Inhibition of SnRK1 by T6P thus diverts carbon skeleton consumption into biosynthetic processes.

Example 1. Design and Synthesis of Signalling Precursors of T6P

Figure 2:
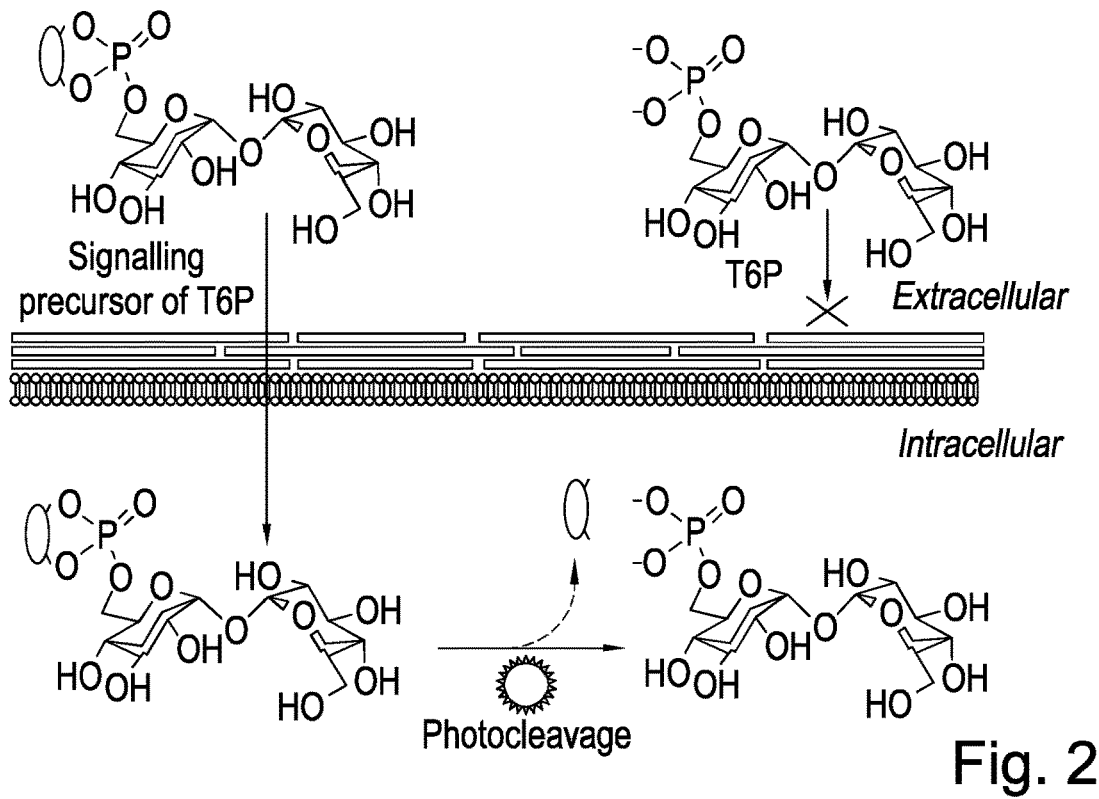
FIG. 2 shows a schematic diagram illustrating the principle of photo-activated release of T6P in planta from plant permeable signalling precursors of T6P.

T6P is plant impermeable (FIG. 2). In order to alter T6P levels in planta, plant permeable signalling precursor variants were designed and synthesised in a single pot reaction starting from suitable precursors.

Synthesis of signalling-precursor compounds 1-4

1H-tetrazole solution (0.45 M in CH$_3$CN) (0.6 mL, 0.24 mmol, 2.0 equiv.) was added into a stirred solution of 12 (100 mg, 0.12 mmol, 1 equiv.) and bis-(2-nitrobenzyl)-N,N-diisopropylphosphoramidite 9 (78.3 mg, 0.18 mmol, 1.5 equiv.) in anhydrous CH$_2$Cl$_2$ (5 mL) under an argon atmosphere at 0° C. The resulting reaction mixture was stirred at 0-5° C. and progress of the reaction was monitored by TLC (petroleum ether:ether; 8:2) and mass spectrometry. After complete disappearance of starting material (1 h), tBuOOH (0.1 mL) was added at 0° C. and stirring was continued for another 30 min. After 30 min the reaction mixture was concentrated in vacuo and the residue was suspended in methanol (2 mL) and stirred in the presence of 30 mg of Dowex-H$^+$ resin for 1 h at room temperature to globally remove TMS groups.

Dowex-H$^+$ was removed through filtration and the filtrate was concentrated, which on flash chromatography (water:

isopropanol:ethyl acetate, 1:2:8) purification yielded 1 (70 mg) in 87% isolable yield. Similar reaction protocols were adopted for the synthesis of compounds 2 and 3. Compound 4 was obtained when a stirred solution of 12 (100 mg, 0.12 mmol) in pyridine (2 mL) at room temperature was treated with POCl$_3$ (0.012 mL, 0.132 mmol) for 10 min followed by addition of 4,5-dimethoxy-2-nitrobenzyl alcohol (76.7 mg, 0.36 mmol) and continuous stirring for 1 h.

The resulting reaction mixture was concentrated in vacuo to yield crude product mixture, which was treated with Dowex-H$^+$ (30 mg) in methanol (2 mL). After filtration, concentration in vacuo and flash chromatography purification yielded 4 (45 mg, 62%) as a pure sticky solid. Full details of the synthesis of each of the compounds are provided below.

Synthetic Protocols, Experimental and Characterization Data for all Compounds

Synthesis of Bis-2-Nitrobenzyl-N,N-Diisopropylphosphoramidite 9

Diisopropylphosphoramidous dichloride 5 (2.0 g, 9.90 mmol) was dissolved in 15 mL of THF and the resulting solution was added slowly to a solution containing 4.2 mL (29.7 mmol) of triethylamine and 3.03 g (19.8 mmol) of 2-nitrobenzyl alcohol 6 in 10 mL of THF at 0° C. The reaction mixture was stirred at 0° C. for 30 min and then at 25° C. for another 2 h. The colorless precipitate was isolated by filtration and the solid was washed with 100 mL of ethyl acetate. The organic phase was washed successively with 15 mL portions of saturated NaHCO$_3$ and saturated NaCl and then dried (MgSO4) and concentrated under reduced pressure at 25° C. The residue was precipitated from ethyl acetate/hexane, affording bis (2-nitrobenzyl) N,N-diisopropylphosphoramidite 9 (3.0 g, 70%) as a colorless solid.[5] (see FIG. 3).

bis-(2-nitrobenzyl)-N,N-diisopropylphosphoramidite 9

Mp 71-72° C. [lit.[5] Mp 71-73° C.]1H NMR (400 MHz, CDCl$_3$) δ 8.10 (d, J=8.4 Hz, 2H, H-3 and H-3'), 7.86 (d, J=8.0 Hz, 2H, H-6 and H-6'), 7.67 (t, J=8.0 Hz, 2H, H-5 and H-5'), 7.44 (t, J=8.4 Hz, 2H, H-4 and H-4'), 5.21 (dd, J=16.4 Hz and J=6.8 Hz, 2H, CH$_2$Ar), 5.12 (dd, J=16.4 Hz and J=6.8 Hz, 2H, CH$_2$Ar), 3.77-3.71 (m, 2H, 2×CH(CH$_3$)$_2$), 1.25 (d, J=8.5 Hz, 12H, 2×CH(CH$_3$)$_2$); $^{13}$C NMR (100 MHz, CDCl$_3$) 146.8 (C-2 and C-2'), 136.1, 136.0 (C-I and C-I'), 133.7 (C-6 and C-6'), 128.5 (C-5 and C-5'), 127.8 (C-4 and C-4'), 124.6 (C-3 and C-3'), 62.5 (CH$_2$Ar), 62.3 (CH$_2$Ar), 43.4 (CH(CH$_3$)$_2$), 43.3 (CH(CH$_3$)$_2$), 24.7 (CH(CH$_3$)$_2$), 24.6 (CH(CH$_3$)$_2$); $^{31}$P NMR (162 MH, CDCl$_3$) δ 149.0; ESI-LRMS m/z calculated for C$_{20}$H$_{26}$N$_3$O$_6$P [M+H]$^+$ 436.1; Found 436.1.

Synthesis of bis-(4,5-dimethoxy-2-nitrobenzyl)-N, N-diisopropylphosphoramidite 10

Figure 4:
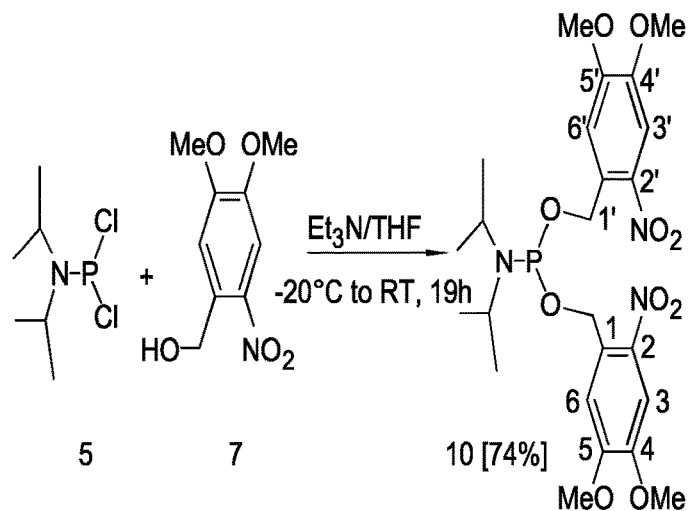
FIG. 4 shows the synthesis of bis-(4,5-dimethoxy-2-nitrobenzyl)-N,N diisopropylphosphoramidite 10.

To a −20° C. cooled suspension of 4,5-dimethoxy-2-nitrobenzyl alcohol 7 (2.1 g, 9.90 mmol) and triethylamine (1.5 mL, 10.8 mmol) in dry THF (10 mL) was added dropwise a solution of diisopropylphosphoramidous dichloride 5 (1.0 g, 4.95 mmol) in dry THF (2 mL). The mixture was allowed to warm to 20° C., stirred for 18 h, and a saturated solution of aq. NaHCO$_3$, (15 mL) added. The solid was filtered, washed with water (20 mL) and dried to give 2.0 g (74%) of 10$^6$. (see FIG. 4)

bis-(4,5-dimethoxy-2-nitrobenzyl)N,N-diisopropylphosphoramidite 10

$^1$H NMR (400 MHz, CDCl$_3$) δ 7.72 (s, 2H, H-3 and H-3'), 7.39 (s, 2H, H-6 and H-6'), 5.24 (dd, J=16.4 Hz and J=6.8 Hz, 2H, CH$_2$Ar), 5.15 (dd, J=16.4 Hz and J=6.8 Hz, 2H, CH$_2$Ar), 3.95 (s, 6H, 2×OMe), 3.94 (s, 6H, 2×OMe), 3.85-3.70 (m, 2H, 2×CH(CH$_3$)$_2$) 1.27 (d, J=8.5 Hz, 12H 2×CH(CH$_3$)$_2$); $^{13}$C NMR (100 MHz, CDCl$_3$) 153.8 (C-5 and C-5'), 147.5 (C-4 and C-4'), 138.6 (C-2 and C-2'), 131.7, 131.6 (C-3 and C-3'), 109.2 (C-1 and C-1'). 107.8 (C-6 and C6'), 62.5 (CH$_2$Ar), 62.4 (CH$_2$Ar), 56.3 (OMe). 43.4 (CH(CH$_3$)$_2$), 43.3 (CH(CH$_3$)$_2$), 25.6 (CH(CH$_3$)$_2$), 24.7 (CH(CH$_3$)$_2$); $^{31}$NMR (162 MHz, CDCl$_3$) 147.4; ESI-LRMS m/z calculated for C$_{24}$H$_{34}$N$_3$O$_{10}$P [M+H]$^+$: 556. L; Found 556.1.

Synthesis of bis-[1-(2-nitrophenyl)-ethyl]N,N-diisopropylphosphoramidite 11

Figure 5:
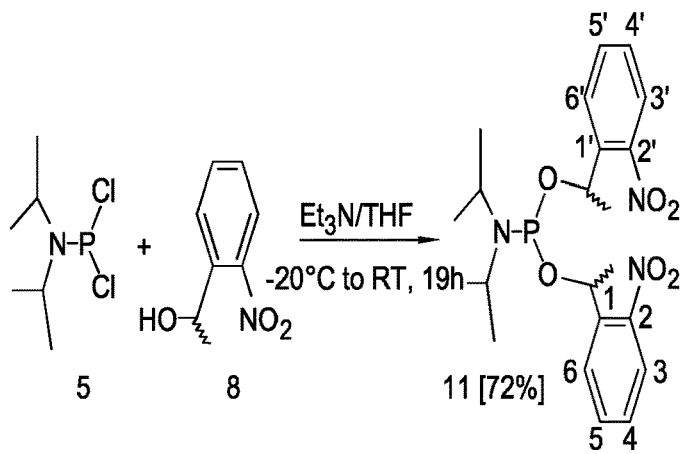
FIG. 5 shows the synthesis of bis-[1-(2-nitrophenyl)-ethyl]-N,N-diisopropylphosphoramidite 11.

Diisopropylphosphoramidous dichloride 5 (1.0 g, 4.95 mmol) was dissolved in 5 mL of dry THF and the resulting solution was added slowly to a solution containing 1.5 mL (10.89 mmol) of triethylamine and 1.65 g (9.90 mmol) of 1-methyl-2-nitrobenzyl alcohol 8 in 10 mL of THF at 0° C., The reaction mixture was stirred at 0° C. for 1 min and then at 25° C. for another 18 h. The reaction mixture was diluted with EtOAc. The organic phase was washed successively with 15 mL portions of saturated NaHCO$_3$ and saturated NaCl and then dried (MgSO4) and concentrated under reduced pressure at 25° C. to get crude product. The residue was purified by flash column chromatography using ethyl acetate/petroleum ether (5:95 v/v), affording bis-[1-(2-nitrophenyl)-ethyl]-N, N-diisopropylphosphoramidite 11 (1.6 g, 72%) as a colorless solid. (see FIG. 5)

Bis-[1-(2-nitrophenyl)-ethyl]-N, N-diisopropylphosphoramidite 11

Isolated as a dia-stereomeric mixture. $^1$H NMR (400 MHz, CDCl$_3$) δ 7.83-7.76 (m, 3H, H-3, H-3' and H-5), 7.54-7.46 (m, 3H, H-5', H-4 and H-4'), 7.33-7.18 (m, 2H, H-6 and H-6'). 5.48-5.29 (m, 2H, CH(CH$_3$)Ar), 3.62-3.44 (m, 2H, 2×CH(CH$_3$)$_2$), 1.55-1.48 (m, 3H, CH(CH$_3$)Ar), 1.40-1.35 (m, 3H, CH(CH$_3$)Ar), 1.13-1.07 (m, 6H, CH(CH$_3$)$_2$), 0.90-0.83 (m, 6H, CH(CH$_3$)$_2$), $^{13}$C NMR (100 MHz, CDCl$_3$)$^5$ 147.2, 147.1, 146.9 (C-2 and C-2'), 141.3. 141.1, 140.8 (C-1 and C-1'), 133.4, 133.3 (C-3 and C-3'), 128.5, 128.3 (C-5 and C-5'), 127.8, 127.7 (C-4 and C-4'), 124.0, 123.9 (C-6 and C-6'), 67.3, 67.2 (CH(CH$_3$)Ar), 67.0, 66.7 (CH(CH$_3$), 43.1. 43.0, 25.1, 25.0 (CH(CH$_3$)$_2$), 24.5, 24.4 (CH(CH$_3$)$_2$), 24.2. 24.1 (CH(CH$_3$)Ar); ESI-LRMS m/z calculated for C$_{22}$H$_{30}$N$_3$O$_6$P [M+11]$^+$; 464.1; Found 464.1.

Synthesis of Compound 1

Figure 6:
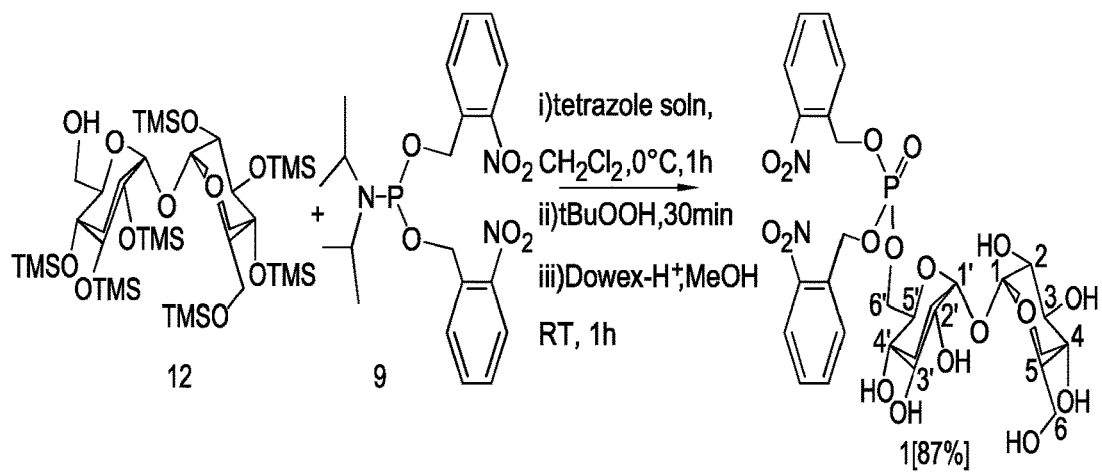
FIG. 6 shows the synthesis of compound 1.

To a solution of 12 (100 mg, 0.12 mmol, 1 equiv.) and 1H-tetrazol solution (16.8 mg, 0.24 mmol, 2.0 equiv. ~0.5 mL of 0.4 M solution in CH$_3$CN) in anhydrous CH$_2$Cl$_2$ (4 mL) under an argon atmosphere at 0° Cm bis-(2-nitrobenzyl) N,N-diisopropylphosphoramidite 9 (78.3 mg, 0.18 mmol, 1.5 equiv.) was added. The solution was stirred for 30 min and progress of the reaction was monitored by TLC (petroleum ether:ether; 8:2). After complete disappearance of starting material, tBuOOH (32.5 mg, 0.36 mmol, 3.0 equiv ~0.1 mL of 5 M solution in decane) was added at 0° C. and stirred for 30 min. After 30 min the reaction mixture was concentrated in vacuo and the residue was stirred with 30 mg of Dowex-H$^+$ resin in methanol (10 mL) for 1 h to obtain deprotected compound as a crude product. This crude product after flash chromatography purification yielded desired product 1 (70 mg) in 87% isolable yield. (see FIG. 6)

6-O-bis-(2-nitrobenzyloxyphosphoryl)-D-trehalose 1

$R_f$ 0.60 (1 water:2 isopropanol:4 ethyl acetate); $[\alpha]_D^{21}$+ 80.6 (c 1.0, MeOH); FT-IR (ATR) ν cm$^{-1}$ (3347 (br, OH), 1526 (s, N=O), 1343 (s, N=O), 1255 (P=O); $^1$H NMR (500 MHz, D$_2$O) δ 8.02 (d, J=8.0 Hz, 2H ArH), 7.66-7.65 (m, 4H, ArH), 7.50-7.46 (m, 2H, ArH), 5.43 (d, J=7.2 Hz, 4H, 2×(CH$_2$Ar), 4.96 (d, J$_{1',2'}$=3.6 Hz, 1H, H-1'), 4.93 (d, J$_{1,2}$=3.6 Hz, 1H, H-1), 4.40 (dd, J$_{6'a,6'b}$=11.0 Hz, J$_{6'a,5}$=2.0 Hz, 1H, H-6'a), 4.35 (dd, J$_{6'B,6'a}$=11.0 Hz, J$_{6'b,5}$=4.5 Hz, 1H, H-6'b), 3.93 (td, J$_{5'4'}$=10.0 Hz and J$_{5',6'a}$=2.0 Hz, 1H, H-5'), 3.71 (t, J$_{32'}$=9.2 Hz, J$_{3',4'}$=9.2 Hz, 1H, H-3'), 3.70-3.68 (m, 1H, H-5), 3.67 (t, J$_{3,2}$=9.6 Hz, J$_{3,4}$=9.6 Hz, 1H, H-3), 3.66-3.65 (m, 1H, H-6a), 3.58 (dd, J$_{6b,6a}$=12.0 Hz and J$_{6b,5}$=5.2 Hz, 1H, H-6b), 3.44 (dd, J$_{2'3'}$=9.9 Hz, J$_{2',1'}$=3.5 Hz, 1H, H-2'), 3.40 (dd, J$_{2,3}$=9.6 Hz, J$_{2,1}$=3.8 Hz, 1H, H-2), 3.27 (t, J$_{4'3'}$=9.6 Hz, J$_{4'5'}$=9.6 Hz, 1H, H-4'), 3.22 (t, J$_{4,3}$=9.6 Hz, J$_{4,5}$=9.6 Hz, 1H, H-4); $^{13}$C NMR (125 MHz, D2O) δ 147.7 (qCAr), 132.2 (qCAr), 132.1 (ArC), 132.0 (ArC), 129.4 (ArC), 129.0 (ArC), 128.9 (ArC), 125.0 (ArC), 94.4 (C-1'), 94.3 (C-1), 73.5 (C-3'), 73.3 (C-3), 72.8 (C-2'), 72.1 (C-2), 72.0 (C-5'), 71.0 (C-5), 70.9 (C-4'), 70.8 (C-4), 70.1 (C-6'), 67.2 (CH$_2$Ar), 66.6 (CH$_2$Ar), 61.6 (C-6); $^{31}$P NMR (162 MHz, D$_2$O) δ −0.11; ESI-HRMS m/z calculated for C$_{26}$H$_{33}$N$_2$O$_{18}$P [M+Na]$^+$715.1368; Found 715.1368.

Synthesis of Compound 2

Figure 7:
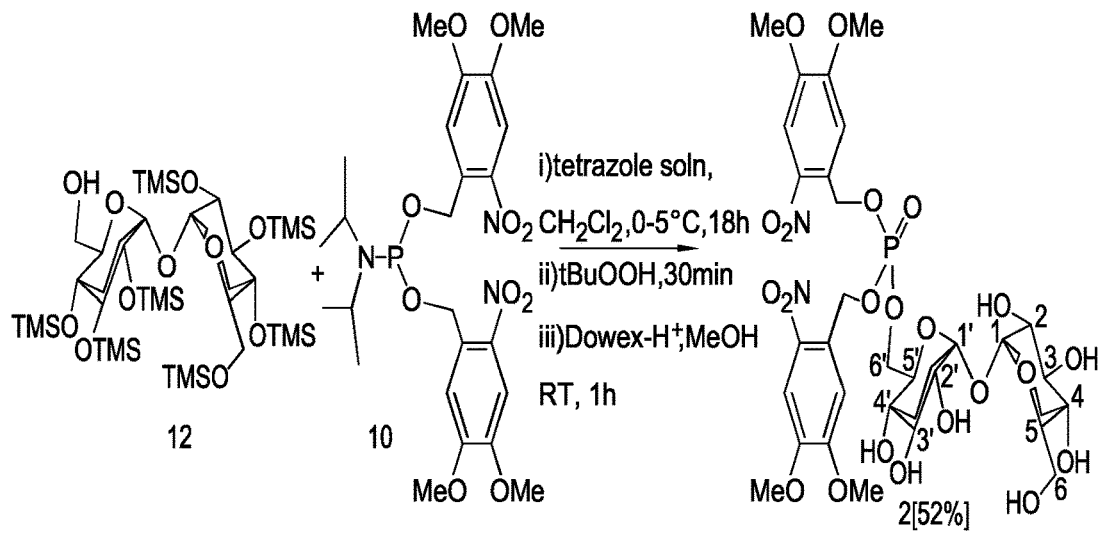
FIG. 7 shows the synthesis of compound 2.

To a solution of 12 (100 mg, 0.12 mmol, 1 equiv.) and 1H-tetrazol (84 mg, 1.2 mmol, 10 equiv. 3.0 mL of 0.4 M solution in CH$_3$CN) in anhydrous CH$_2$Cl$_2$ (8 mL) under an argon atmosphere at 0° C., bis-(4,5-dimethoxy-2-nitrobenzyl)-N,N-diisopropylphosphoramidite 10 (100 mg, 0.18 mmol, 1.5 equiv.) was added and the resulting reaction mixture was stirred at 0-5° C. The progress of the reaction was monitored by TLC (petroleum ether:ether; 8:2). After complete disappearance of starting material (18 h), tBuOOH (32.5 mg, 0.36 mmol, 3.0 equiv. ~0.1 mL of 5 M solution in decane) was added at 0° C. and the mixture stirred for a further 30 min. After 30 min the reaction mixture was concentrated in vacuo and the residue was stirred with 30 mg of Dowex-H$^+$ resin in methanol (10 mL) for 1 h to obtain deprotected compound as crude product. This crude product after flash chromatography purification yielded desired product 2 (50 mg) in 52% isolable yield. (see FIG. 7)

6-O-bis-(4,5-dimethoxy-2-nitrobenzyloxyphosphoryl)-D-trehalose 2

$R_f$ 0.50 (1 water; 2 isopropanol:4 ethyl acetate); $[\alpha]_D^{21}$+ 64.8 (c 1.1, MeOH); FT-IR (ATR) ν cm$^{-1}$ 3347 (br, OH), 1519 (s, N=O), 1326 (s, N=O), 1220 (P=O); $^1$H NMR (500 MHz, CD$_3$OD) β 7.53 (s, 2H, ArH), 7.03 (s, 2H, ArH), 5.37 (d, J=8.0 Hz, 4H, 2×CH2Ar), 4.95 (d, J$_{1',2'}$=4.0 Hz, 1H, H-1'), 4.91 (d, J$_{1,2}$=4.0 Hz, 1H, H-1), 4.30 (dd, J$_{6'a, 6'b}$=11.6 Hz, J$_{6'a,5}$=2.0 Hz, 1H, H-6'a), 4.35 (dd, J$_{6'b,6'a}$=11.0 Hz, J$_{6b,5}$=3.6 Hz, 1H, H-6'b), 3.94 (td, =10.0 Hz and J$_{5',6'a}$=2.0 Hz, 1H, H-5'), 3.71 (t, J$_{3',2'}$=9.6 Hz, J$_{3',4'}$=9.6 Hz, 1H, H-3'), 3.70-3.68 (m, 1H, H-5), 3.67 (t, J$_{3,2}$=9.6 Hz, J$_{3,4}$=9.6 Hz, 1H, H-3), 3.66-3.65 (m, 1H, H-6a), 3.58 (dd, J$_{6b,6a}$=11.6 Hz and J$_{6b,5}$=5.6 Hz, 1H, H-6b), 3.35 (dd, J$_{2'3'}$=8.4 Hz, J$_{2',1}$=4.0 Hz, 1H, H-2'), 3.33 (dd, J$_{2,3}$=8.5 Hz, J$_{2,1}$=3.8 Hz, 1H, H-2), 3.26 [t, J$_{4',3'}$=8.8 Hz, J$_{4'5'}$=8.8 Hz, 1H, H-4'), 3.24 (t, J$_{4,3}$=9.6 Hz, J$_{4,5}$=9.6 Hz, 1H, H-4); $^{13}$C NMR (125 MHz, CD$_3$OD) 154.2 (qCAr), 148.9. (qCAr), 143.7 (qCAr), 139.6 (ArC), 126.8 (ArqC), 126.6 (ArC), 110.4 (ArC), 110.3 (ArC), 108.2, 94.4 (C-1'), 94.3 (C-1), 73.5 (C-3'), 73.3 (C-3), 72.8 (C-2'), 72.1 (C-2), 72.0 (C-5'), 70.8 (C-5), 70.2 (C-6'), 69.7 (CH$_2$Ar), 66.6 (CH$_2$Ar), 61.6 (C-6), 56.1 (2×OMe), 55.8 (2×OMe); $^{31}$P NMR (162 MHz CD$_3$OD) δ −0.15; ESI-HRMS m/z calculated for C$_{30}$H$_{41}$N$_2$O$_{22}$P [M+Na]$^+$; 835.1786; Found 835.1782.

Synthesis of Compound 3

Figure 8:
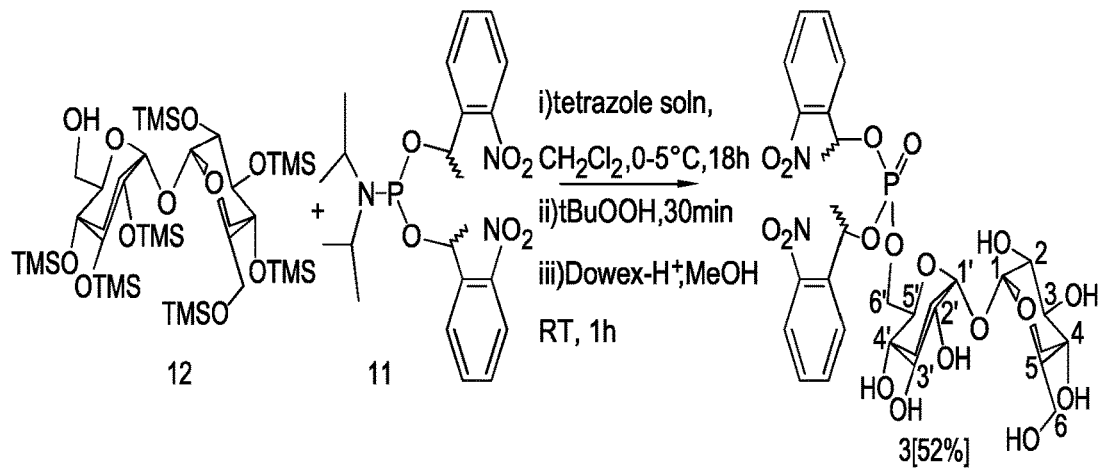
FIG. 8 shows the synthesis of compound 3.

To a solution of 12 (100 mg, 0.12 mmol, 1 equiv.) and 1H-tetrazol (84 mg, 1.2 mmol, 10 equiv. 3.0 mL of 0.4 M solution in CH$_3$CN) in anhydrous CH$_2$Cl$_2$ (8 mL) under an argon atmosphere at ° C., bis-[1-(2-nitrophenyl)-ethyl]-N, N-diisopropylphosphoramidite 11 (83.5 mg, 0.18 mmol, 1.5 equiv.) was added and the resulting reaction mixture was stirred at 0-5° C. The progress of the reaction was monitored by TLC (petroleum ether:ether; 8:2) and mass spectrometry. After complete disappearance of starting material (18 h), tBuOOH (32.5 mg, 0.36 mmol, 3.0 equiv. ~0.1 mL of 5 M solution in decane) was added at 0° C. and stirred for 30 min. After 30 min the reaction mixture was concentrated in vacuo and the residue was stirred with 30 mg of Dowex-H$^+$ resin in methanol (10 mL) for 1 h to obtain deprotected compound as crude product. This crude product after flash chromatography purification yielded desired product 3 (44 mg) in 52% isolable yield. (see FIG. 8)

6-O-bis[1-(2-nitrophenyl)-ethoxyphosphoryl]-D-trehalose 3

Isolated as mixture of four diastereomers. $R_f$ 0.65 (1 water:2 isopropanol:4 ethyl acetate); FT-IR (ATR) ν cm$^{-1}$ 3394 (br, OH), 1521 (s, N=O), 1326 (s, N=O), 1276 (P=O); $^1$H NMR (500 MHz, CD$_3$OD) δ 7.91-7.05 (m, 8H, ArH), 5.92-5.84 (m, 2H, 2×CHMe), 5.04-4.94 (in, 2H, H-1 and H-1'), 3.90-3.60 (m, 7H), 3.41-3.05 (m, 5H), 1.56-1.46 (m, 6H, 2×CHMe); $^{13}$C NMR (125 MHz, CD$_3$OD δ 148.8, 148.3, 148.2 148.1 (qCAr), 147.9, 145.4, 138.9, 138.3 (qCAr), 138.2, 135.4, 135.3, 135.2 (ArC), 130.4, 130.3, 129.9, 129.3, 129.2, 128.8 (ArC) 128.7, 128.6, 126.3, 125.6, 125.5 (ArC), 95.4 (C-1'), 95.3 (C-1), 79.8, 74.6 (C-3'), 74.4, 74.2, (C-3), 74.0, 73.9 (C-2'), 73.6, 73.3 (C-2), 73.2, 73.1 (C-5'), 73.0, 72.9 (C-5), 71.9, 71.8 (C-4'), 71.2, 71.1 (C-4), 71.0 (C-6'), 68.5, 68.4 (CHMe$_2$), 68.2, 68.1 (CHMe$_2$), 62.6, 62.1 (C-6), 30.7, 30.5, 24.7 (CHCH$_3$), 24.6, 23.5, 23.7 (CHCH$_3$); $^{31}$P NMR (162 MHz, CD$_3$OD) δ −1.70, −2.20, −2.50, −2.81 (P=O) four peaks from different diastereomers; ESI-HRMS m/z calculated for C$_{28}$H$_{37}$N$_2$O$_{18}$P [N+Na]$^+$: 743.1677; Found 743.1676.

Synthesis of Compound 4

Figure 9:
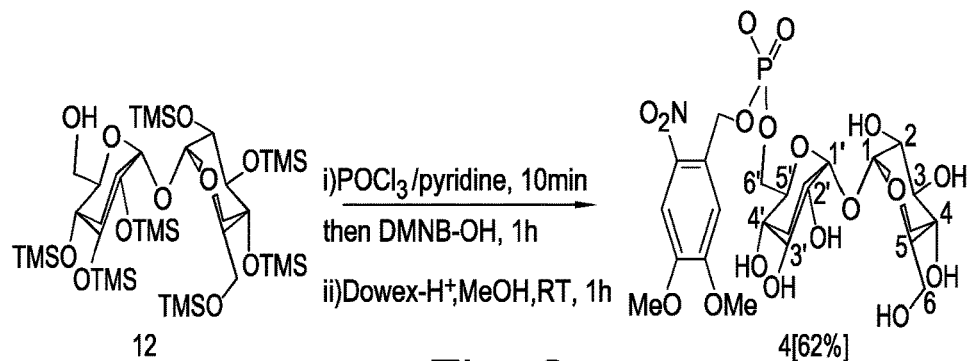
FIG. 9 shows the synthesis of compound 4.

To a stirred solution of compound 12 (100 mg, 0.12 mmol) in pyridine (2 mL) at room temperature, POCl$_3$ (0.012 mL, 0.132 mmol) was added dropwise and the mixture was stirred for a further 10 min. After 10 min 4,5-dimethoxy-2-nitrobenzyl alcohol (DMNB-OH) (76.7 mg, 0.36 mmol) was added and the reaction mixture stirred for further 1 h. The reaction mixture was concentrated in vacuo to get crude product mixture, which after treatment with Dowex-H+ (50 mg) in methanol (2 mL) furnished compound 2 and 4. After filtration, concentration in vacuo and flash chromatography purification yielded 4 (45 mg, 62%) as a gum. (see FIG. 9)

6-O-(4,5-dimethoxy-2-nitrobenzyloxyphosphoryl)-D-trehalose 4

$R_f$ 0.33 (1 water:2 isopropanol:4 ethyl acetate); $[\alpha]_D^{21}$+ 48.7 (c 1.1, MeOH); FT-IR (ATR) ν cm$^{-1}$ 3312 (br, OH), 1521 (s, N=O), 1326 (s, N=O), 1220 (P=O); $^1$H NMR (500 MHz, CD$_3$OD) δ 7.62 (s, 1H, ArH), 7.39 (s, 1H, ArH), 5.21 (d, J=6.0 Hz, 2H, CH$_2$Ar), 4.91 (d, $J_{1,2}$=4.0 Hz, 1H, H-1'), 4.87 (d, $J_{1,2}$=4.0 Hz, 1H, H-1), 4.14-3.98 (m, 2H, H-6'), 3.88 (s, 3H, OMe), 3.80 (s, 3H, OMe), 3.71-3.65 (m, 4H, H-6a, H-3', H-3 and H-5'), 3.57 (dd, $J_{6b,6a}$=12.0 Hz and $J_{6b,5}$=5.6 Hz, 1H, H-6b), 3.35 (dd, =7.2 Hz and $J_{2,1}$=3.6 Hz, 1H, H-2'), 3.32 (dd, $J_{2,3}$=6.8 Hz and $J_{2,1}$=3.4 Hz, 1H, H-2), 3.22-3.21 (m, 3H, H-4', H-4 and H-5); $^{13}$C NMR (125 MHz, CD$_3$OD) δ 155.5 (qC Ar), 149.0 (qC Ar) 139.9 (qC Ar), 132.1 (qC Ar), 110.8 (ArC), 109.0 (ArC), 95.3 (C-1'), 95.2 (C-1), 74.4 (C-3'), 74.3 (C-3), 73.7 (C-2'), 73.2 (C-2), 73.1 (C-5'), 72.7 (C-5), 71.8 (C-4'), 71.4 (C-4), 65.9 (CH$_2$Ar), 65.5 (C-6'), 62.6 (C-6), 57.0 (OMe), 56.8 (OMe); $^{31}$P NMR (162 MHz, CD$_3$OD) δ 2.18 (P=O): ESI-HRMS m/z calculated for C$_{21}$H$_{32}$NO$_{18}$P [M−H]$^-$: 616.1279; Found 616.1273.

Synthesis of Compound 13

Figure 10:
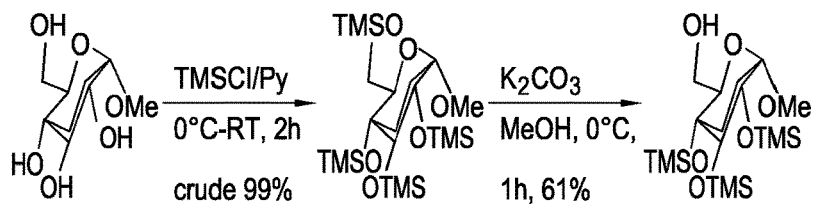
FIG. 10 shows the synthesis of compound 13.

Methyl tetra-O-trimethylsilyl-α-D-glucopyranoside (3.0 gm, 4.14 mmol, 1 equiv.) was dissolved in methanol (50 mL) and kept at 0° C. followed by the addition of K$_2$CO$_3$ solution in MeOH (50 mL, 4.5 g/L) at 0-4° C. and stirred for 1 h (TLC, EtOAc:petroleum ether; 1:4). After neutralization with AcOH (5 mL), the mixture was concentrated to yield crude product mixture. The crude product mixture was dissolved in dichloromethane (50 mL) and washed with water (3×15 mL). The dichloromethane layer was separated and concentrated in vacuo. Flash chromatography (EtOAc: petroleum ether; 1:9) yielded desired product 13 (1.56 g, 61%).[2] (see FIG. 10)

Methyl 2,3,4-tri-O-trimethylsilyl-α-D-glucopyranoside 13 colourless solid $[\alpha]_D^{21}$+95.3 (c 1, CHCl$_3$), [lit$_2$ $[\alpha]_D^{21}$+93 (c3, CHCl$_3$)]; $^1$H NMR (400 MHz, CDCl$_3$): δ 4.61 (d, $J_{1,2}$=3.6 Hz, 1H, H-1), 3.78-3.74 (m, 2H, H-6' and H-3), 3.68 (dd, $J_{6,5}$=4.4 Hz $J_{6,6}$=11.6 Hz, 1H, H-6), 3.57 (ddd, $J_{5,4}$=9.6 Hz, $J_{5,6}$=4.3 Hz, $J_{5,6'}$=3.1 Hz, 1H, H-5), 3.48 (dd, $J_{2,1}$=3.0 Hz, $J_{2,3}$=8.4 Hz, 1H, H-2), 3.45 (dd, J=6.4 Hz, J=2.4 Hz, 1H, H-4), 3.34 (s, 3H, OMe), 0.17 (s, 9H, Si(CH$_3$)$_3$), 0.15 (s, 9H, Si(CH$_3$)$_3$), 0.14 (s, 9H, Si(CH$_3$)$_3$); $^{13}$C NMR (100 MHz, CDCl$_3$); δ 99.6 (C-1), 74.8 (C-3), 73.7 (C-2), 71.9 (C-4), 71.5 (C-5), 61.8 (C6), 54.8 (OMe), 1.2 (s, 3C, Si(CH$_3$)$_3$), 0.86 (s, 3C, Si(CH$_3$)$_3$), 0.46 (s, 3C, Si(CH$_3$)$_3$); ESI-LRMS m/z calculated for C$_{16}$H$_{38}$O$_6$SI$_3$ [M+Na]$^+$: 433.18; Found 433.20.

Synthesis of Compound 14

Figure 11:
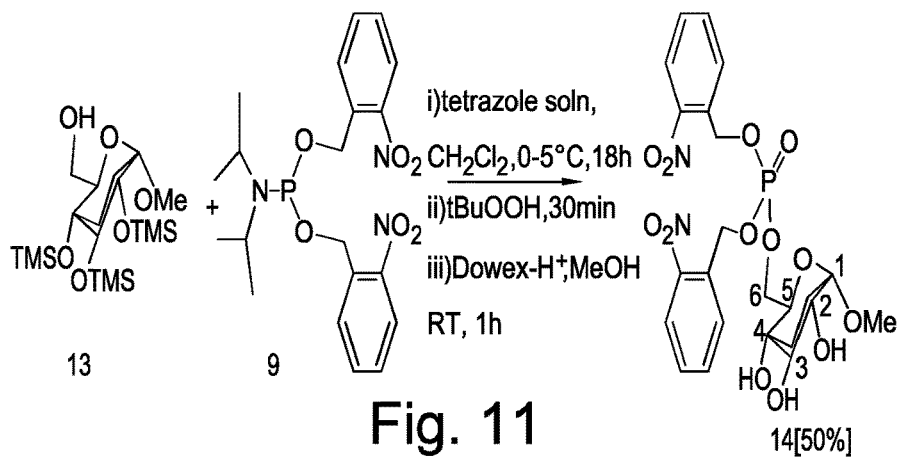
FIG. 11 shows the synthesis of compound 14.

To a solution of 13 (100 mg, 0.24 mmol, 1 equiv.) and 1H-tetrazol (85 mg, 1.21 mmol, 5.0 equiv. 3.0 mL of 0.4 M soln in CH$_3$CN) in dry CH$_2$Cl$_2$ (8 mL) under an argon atmosphere at 0° C., bis-(2-nitrobenzyl)-N,N-diisopropylphosphoramidite 9 (156 mg, 0.36 mmol, 1.5 equiv.) was added. The solution was stirred overnight at 0-5° C. After complete disappearance of starting material (18 h), tBuOOH (64.8 mg, 0.72 mmol, 3.0 equiv. ~0.2 ml of 5.0 M soln in decane) was added at 0° C. After 30 min of stirring the mixture was concentrated to dryness. The residue was dissolved in methanol (15 mL) and stirred with 30 mg of Dowex-H+ resin for 1 h to obtain deprotected compound. After 1 h the mixture was filtered and the filtrate was concentrated to yield deprotected crude product which on flash chromatography purification yielded desired product 14 (66 mg) in 50% isolable yield. (see FIG. 11)

Methyl 6-O-bis-(2-nitrobenzyloxyphosphoryl)-α-D-glucopyranoside 14

$R_f$0.50 (1 Methanol: 9 dichloromethane); $[\alpha]_D^{21}$+49.5 (c 1.0, MeOH); FT-IR (ATR) ν cm$^{-1}$ 3354 (br, OH), 1525 (s, N=O), 1342 (s, N=O), 1255 (P=O); $^1$H NMR (400 MHz, CD$_3$OD): δ 8.00 (d, J=8.0 Hz, 2H, ArH), 7.67-7.61 (m, 4H, ArH), 7.48 (t, J=8.0 Hz, 1H, ArH), 7.47 (t, J=8.0 Hz, 1H, ArH), 5.44 (d, J=7.2 Hz, 4H, 2×CH$_2$Ar), 4.50 (d, $J_{1,2}$=3.6 Hz, 1H, HA), 4.31 (ddd, $J_{6a,6b}$=11.2 Hz, $J_{6a,31P}$=6.4 Hz, $J_{6a,5}$=1.6 Hz, 1H, H-6a), 4.22 (ddd, $J_{6b,6a}$=12.0 Hz, $J_{6b,31P}$=7.2 Hz, $J_{6b,5}$=4.8 Hz, 1H, H-6b), 3.57 (ddd, $J_{5,4}$=10.0 Hz, $J_{5,6}$=4.8 Hz, $J_{5,6}$=1.6 Hz, 1H, H-5) 3.50 (brt, $J_{3,2}$=9.2 Hz $J_{3,4}$=9.2 Hz, 1H, H-3), 3.24 (dd, $J_{2,1}$=3.6 Hz, $J_{2,3}$=9.2 Hz, 1H, H-2), 3.23 (s, 3H, OMe), 3.20 (dd, $J_{4,3}$=9.2 Hz, $J_{4,5}$=9.7 Hz, 1H, H-4); 13C NMR (400 MHz, CD$_3$OD): δ 147.3 (qC Ar), 143.3 (qC Ar), 134.2, 132.0, 129.4, 128.8, 125.0 (ArC), 100.3 (C-1), 73.9 (C-3), 72.3 (C-2), 70.7 (C5), 70.1 (C-4), 67.9 (C-6), 66.5 (CH$_2$Ar), 54.7 (OMe); $^{31}$P NMR (162 MHz, CD$_3$OD) δ −1.65; ESI-HRMS m/z calculated for C$_{21}$H$_{25}$N$_2$O$_{13}$P [M+Na]$^+$: 567.0986; Found 567.0983.

Synthesis of Compound 15

Figure 12:
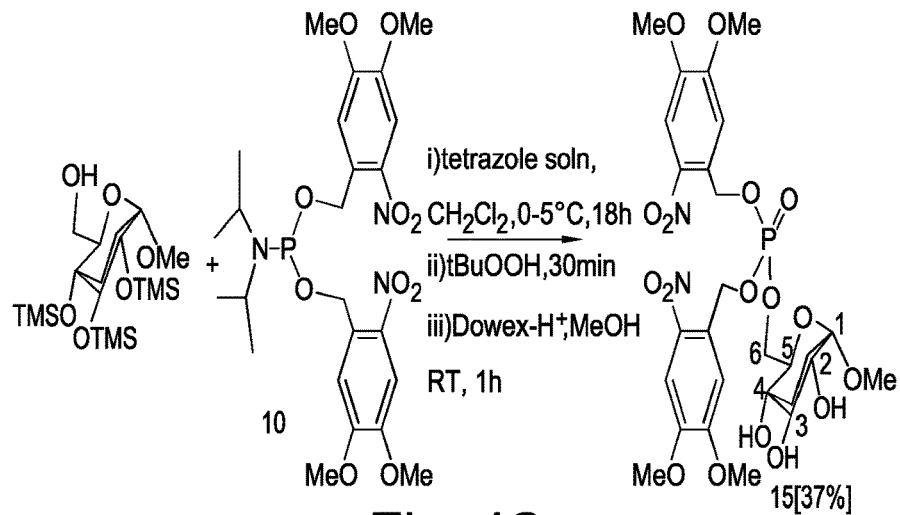
FIG. 12 shows the synthesis of compound 15.

To a solution of 13 (100 mg, 0.24 mmol, 1 equiv.) and 1H-tetrazol (85 mg, 1.21 mmol, 5.0 equiv, 3.0 mL of 0.4 M soln in CH$_3$CN) in dry CH$_2$Cl$_2$ (8 mL) under an argon atmosphere at 0° C., bis-(4,5-dimethoxy-2-nitrobenzyl)-N,N-diisopropylphosphoramidite 10 (200 mg, 0.36 mmol, 1.5 equiv.) was added. The solution was stirred overnight at 0-4° C. After complete disappearance of starting material (18 h), tBuOOH (64.8 mg, 0.72 mmol, 3.0 equiv. ~0.2 mL of 5.0 M soln in decane) was added at 0° C. After 30 min of stirring the mixture was concentrated to dryness. The residue was dissolved in methanol (15 mL) and stirred with 30 mg of Dowex-H+ resin for 1 h to obtain deprotected compounds. After 1 h the mixture was filtered and the filtrate was concentrated to yield fully deprotected crude product which on flash chromatography yielded desired product 15 (60 mg) in 37% isolable yield. (see FIG. 12)

Methyl 6-O-bis-(4,5-dimethoxy-2-nitrobenzyloxy-phosphoryl-α-D-glucopyranoside 15

$R_f$0.40 (1 Methanol: 9 dichloromethane); $[\alpha]_D^{21}$+40.7 (c 1.09, MeOH); FT-IR (ATR) ν cm$^{-1}$ 3355 (br, OH), 1519 (s, N=O), 1326 (s, N=O), 1220 (P=O); $^1$H NMR (400 MHz, CD$_3$OD): δ 7.51 (s, 2H, ArH), 7.03 (s, 2H, ArH), 5.37 (d, J=8.0 Hz, 4H, 2×CH$_2$Ar), 4.50 (d, $J_{1,2}$=3.6 Hz, 1H, H-1), 4.32 (ddd, $J_{6a,6b}$=11.2 Hz, $J_{6a,31P}$=6.4 Hz, $J_{60}$=1.6 Hz, 1H, H-6a), 4.22 (ddd, $J_{6b,6a}$=12.0 Hz, $J_{6b,31P}$=7.2 Hz, $J_{6N5}$=4.8 Hz, 1H, H-6b), 3.80 (s, 3H, OMe), 3.78 (s, 3H, OMe), 3.57 (dd, $J_{5,4}$=10.0 Hz, $J_{5,6b}$=4.8 Hz, 1H, H-5), 3.50 (brt, $J_{3,2}$=9.2 Hz, $J_{3,4}$=9.2 Hz, 1H, H-3), 3.25 (dd, $J_{2,1}$=3.6 Hz, $J_{2,3}$=9.2

Hz, 1H, H-2), 3.24 (s, 3H, OMe), 3.21-3.16 (m, 1H, H-4); $^{13}$C NMR (400 MHz, CD$_3$OD): δ 154.1, 148.9 (qC Ar), 143.2, 139.5 (qC Ar), 126.6 110.3, 108.1 (ArC), 100.3 (C-1), 73.9 (C-3), 72.3 (C-2), 70.7 (C-5), 70.1 (C-4), 68.0 (C-6), 66.8 (CH$_2$AR), 56.0, 55.8 (OMe), 54.7 (OMe); $^{31}$P NMR (162 MHz, CD$_3$OD) δ −1.62; ESI-HRMS m/z calculated for C$_{25}$H$_{33}$N$_2$O$_{17}$P [M+Na]$^+$ 687.1409; Found 687,1421.

Synthesis of Compound 16

Figure 13:
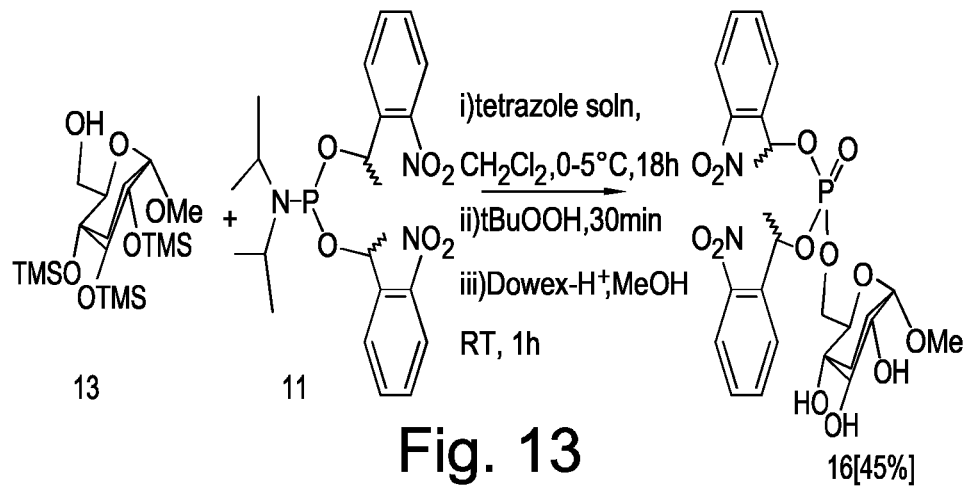
FIG. 13 shows the synthesis of compound 16.

To a solution of 13 (100 mg, 0.24 mmol, 1 equiv.) and 1H-tetrazol (85 mg, 1.21 mmol, 5.0 equiv, 3.0 mL of 0.4 M sole in CH$_3$CN) in dry CH$_2$Cl$_2$ (5 mL) under an argon atmosphere at 0° C., bis-[1-(2-nitrophenyl)-ethyl]-N,N-diisopropylphosphoramidite 11 (167 mg, 0.36 mmol, 1.5 equiv.) was added. The solution was stirred overnight (15 h) at 0-4° C. After complete disappearance of starting material, t-BuOOH (64.8 mg, 0.72 mmol, 3.0 equiv ~0.2 ml of 5.0 M soln in decane) was added at 0° C. After 30 min of stirring the mixture was concentrated in vacuo. The residual mixture was deprotected by stirring in methanol (15 mL) with 25 mg of Dowex-H$^+$ resin for 1 h. After filtration the filtrate was concentrated to yield fully deprotected crude product which on flash chromatography purification yielded desired product 16 (62 mg) in 45% yield. (see FIG. 13)

Methyl 6-O-bis[1-(2-nitrophenyl)-ethoxyphosphoryl]-α-D-glucopyranoside 16

R$_f$0.55 (1 Methanol: 9 dichloromethane); Isolated as a mixture of four diastereomers, FT-IR (ATR) v 3334 cm$^{-2}$ (br, OH), 1520 (s, N=O), 1325 (s, N=O), 1219 (P=O); $^1$H NMR (400 MHz, CD$_3$OD); δ 7.86-7.84 (m, 2H, ArH), 7.75-7.50 (m, 3H, ArH), 7.45-7.34 (m, 3H, ArH), 5.89-5.80 (m, 2H, 2×CH(CH$_3$), 4.57-4.45 (4d, J$_{1,2}$=3.6 Hz, 1H, H-1), 4.16-3.89 (m, 2H, H-6), 3.51-3.40 (m, 2H, H-5 and 11-3), 3.31-3.25 (m, 1H, H-2), 3.25, 3.22 3.17, 3.13 (4s, 3H, OMe), 3.16-3.12 (m, 1H, H-4), 1.68-1.57 (4d, J=6.8 Hz, 6H, 2×CH(CH$_3$): $^{13}$C NMR (400 MHz, CD$_3$OD): δ 137.2, 137.2, 134.3, 134.2, 129.4, 129.3, 127.8, 127.7, 127.6, 127.5, 124.6, 124.5 (ArC), 100.7, 100.3, 100.2, 100.1 (C-1), 74.0, 73.9 (C-3), 73.3, 73.2 (C-2), 72.9, 72.3 (C-5), 72.2, 70.6 (C-4), 70.5, 70.1 (C-6), 70.0, 67.4 (CH(CH$_3$)), 55.1, 54.8, 54.7, 54.6 (OMe), 23.6, 23.5, 23.4 (CH(CH$_3$)); $^{31}$P NMR (162 MHz, CD$_3$OD) δ −3.2, −3.7, −3.8, −4.0; ESI-HRMS m/z calculated for C$_{23}$H$_{29}$N$_2$O$_{13}$P [M+Na]$^+$: 595.1299; Found 595.1305.

Synthesis of Compound 17

Figure 14:
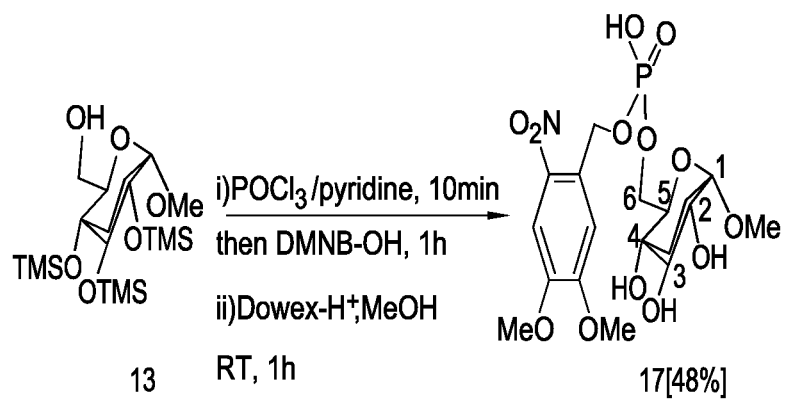
FIG. 14 shows the synthesis of compound 17.
Figure 15:
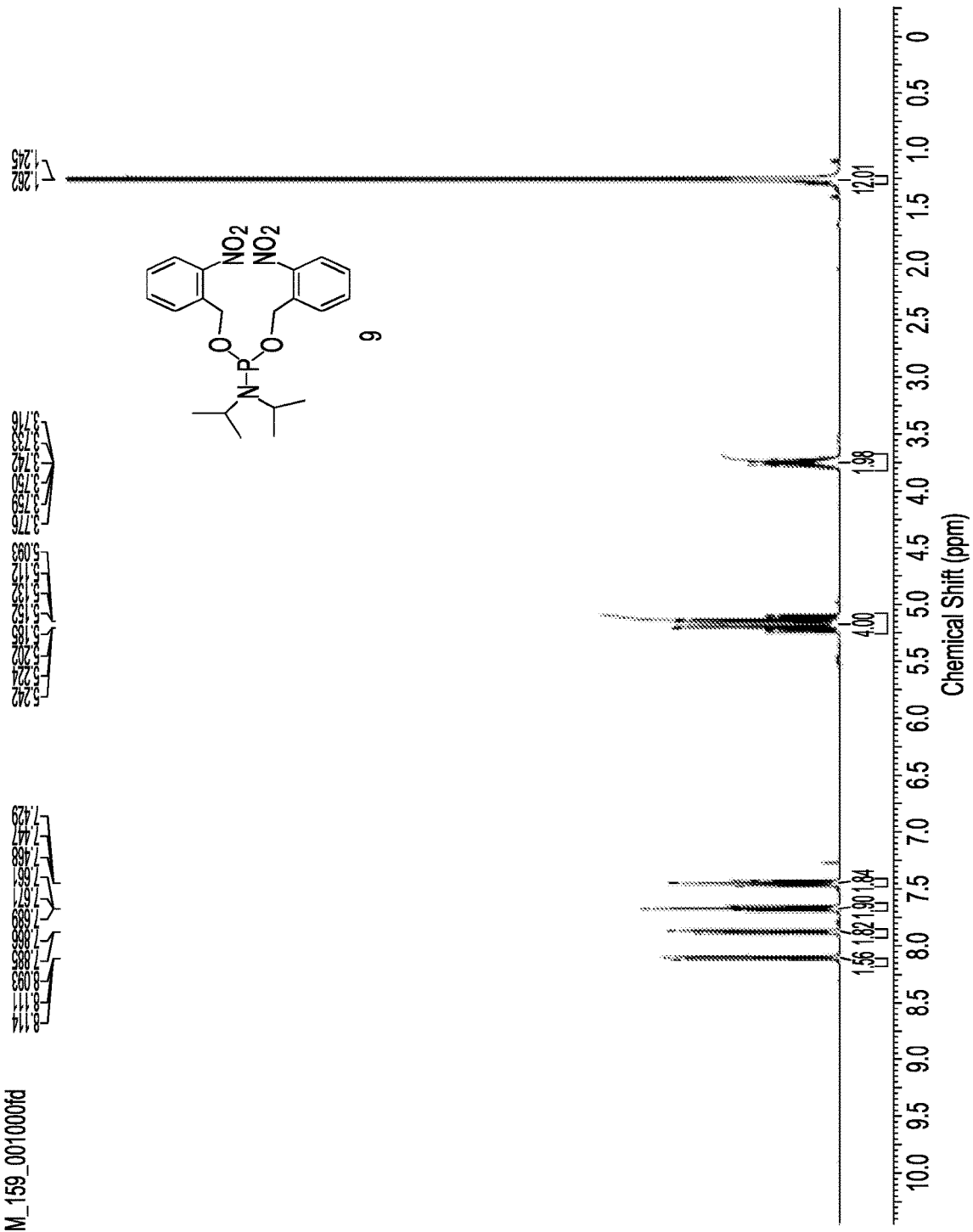
FIG. 15 shows the $^1$H and $^{13}$C NMR Spectra of compound 9.
Figure 16:
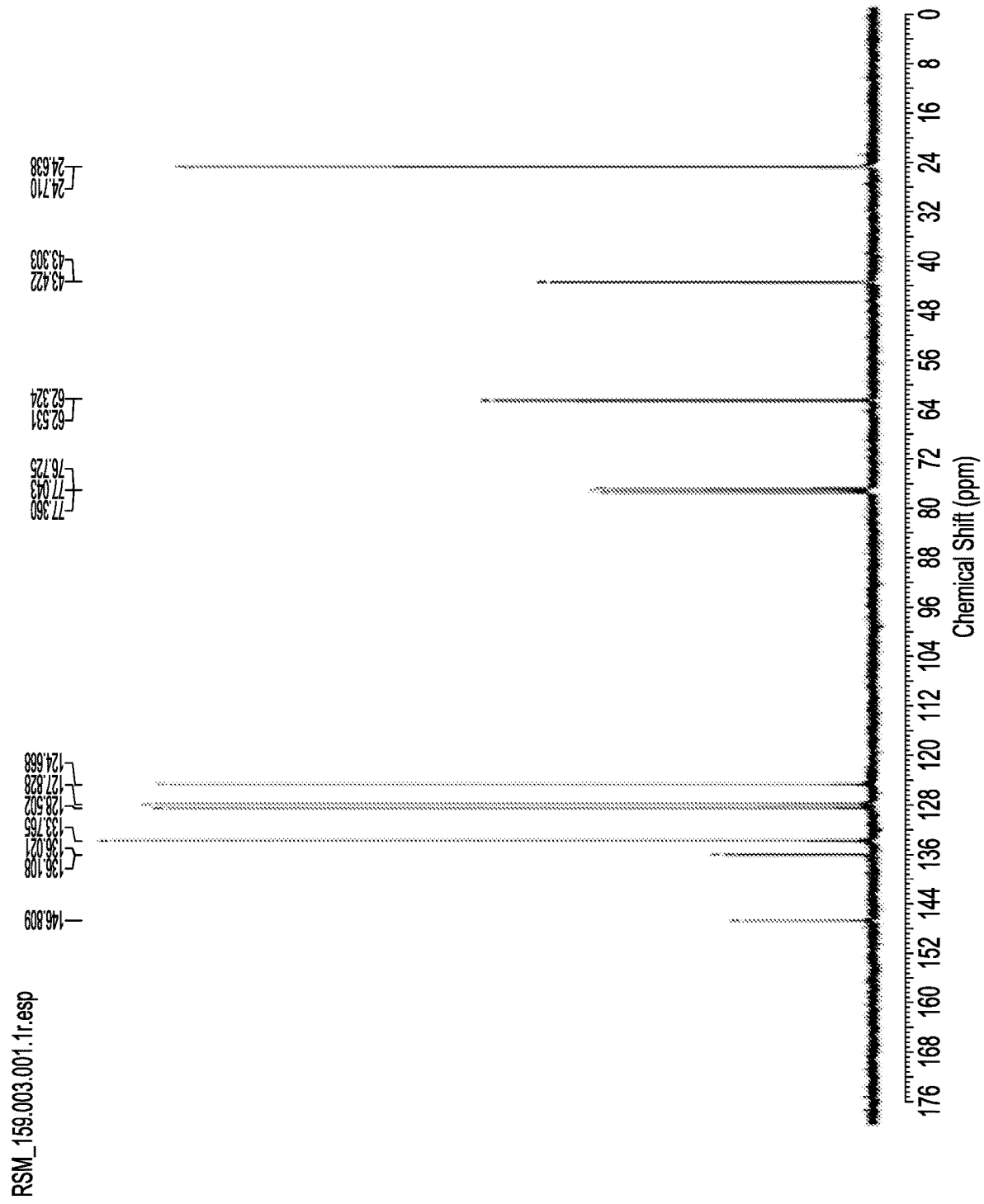
FIG. 16 shows the $^1$H and $^{13}$C NMR Spectra of compound 9.
Figure 17:
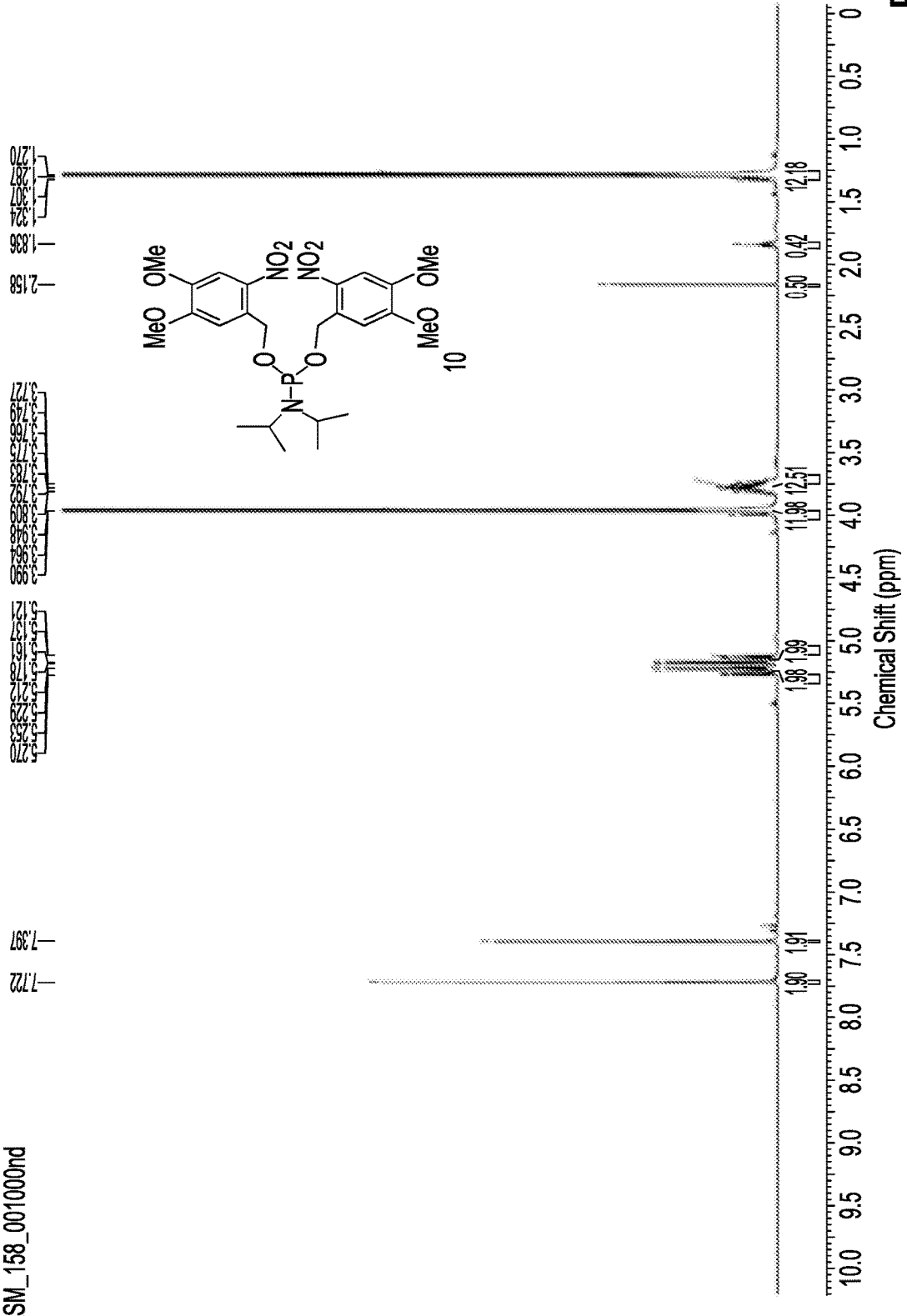
FIG. 17 shows the $^1$H and $^{13}$C NMR Spectra of compound 10.
Figure 18:
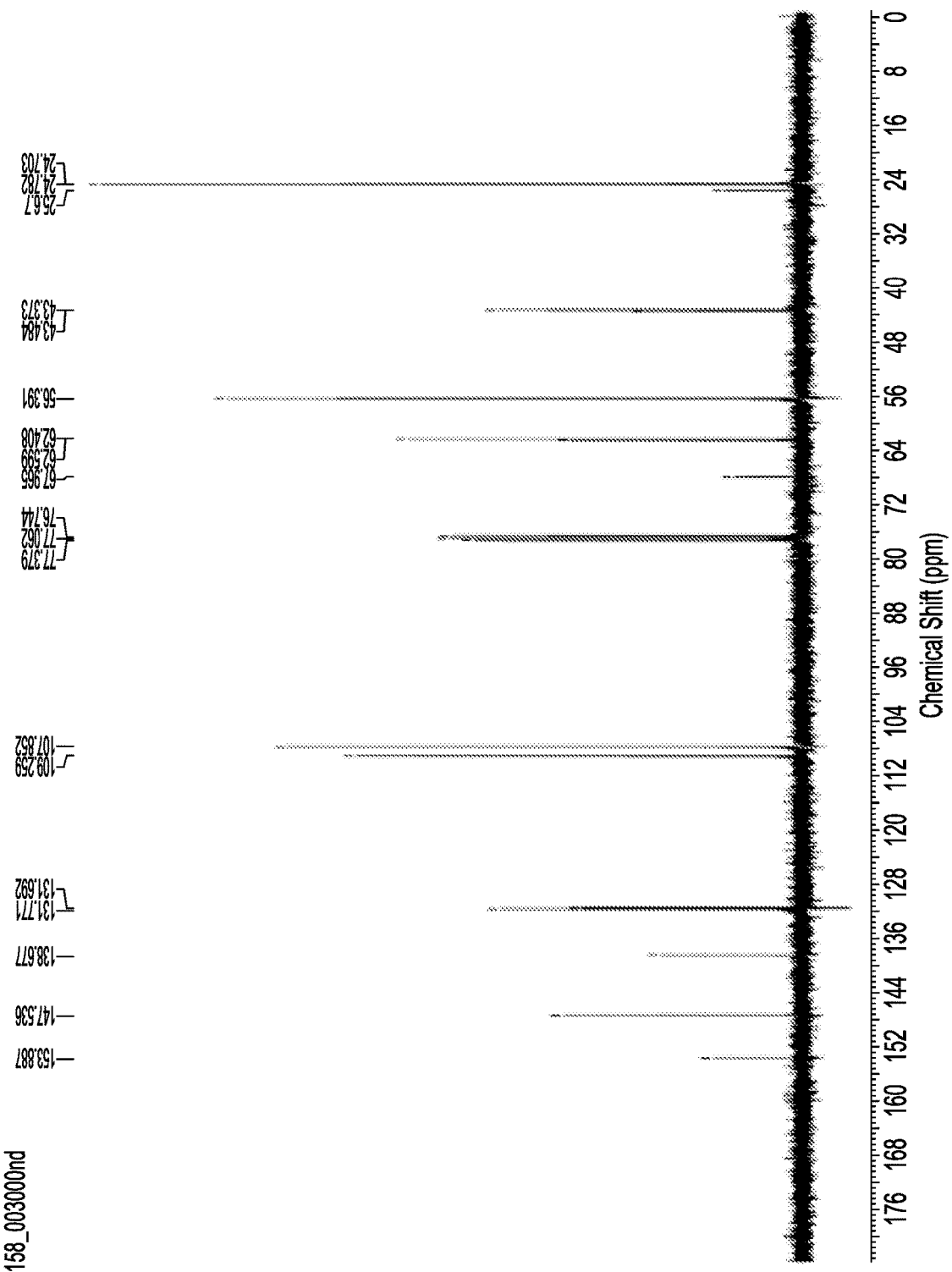
FIG. 18 shows the $^1$H and $^{13}$C NMR Spectra of compound 10.
Figure 19:
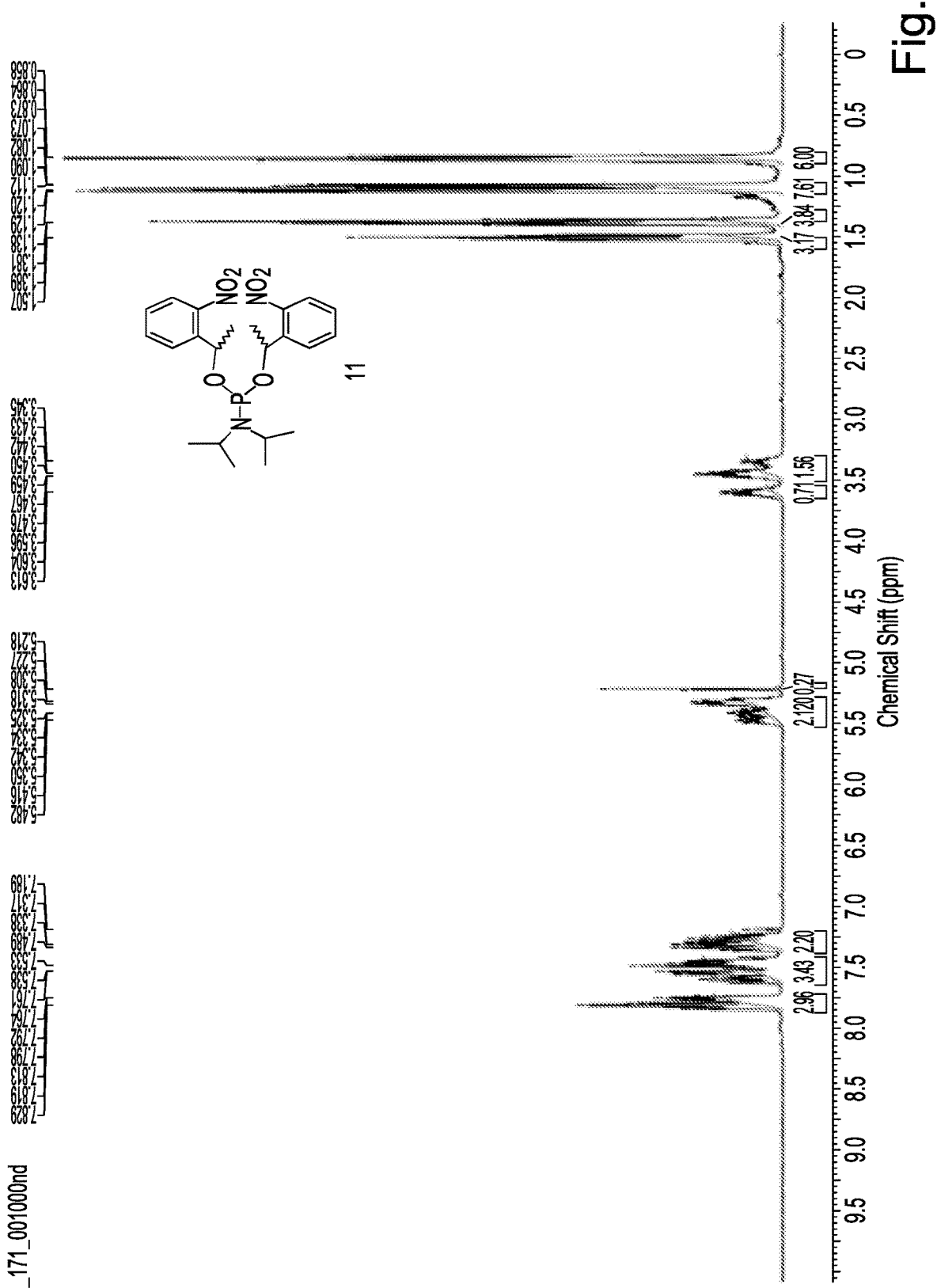
FIG. 19 shows the $^1$H and $^{13}$C NMR Spectra of compound 11.
Figure 20:
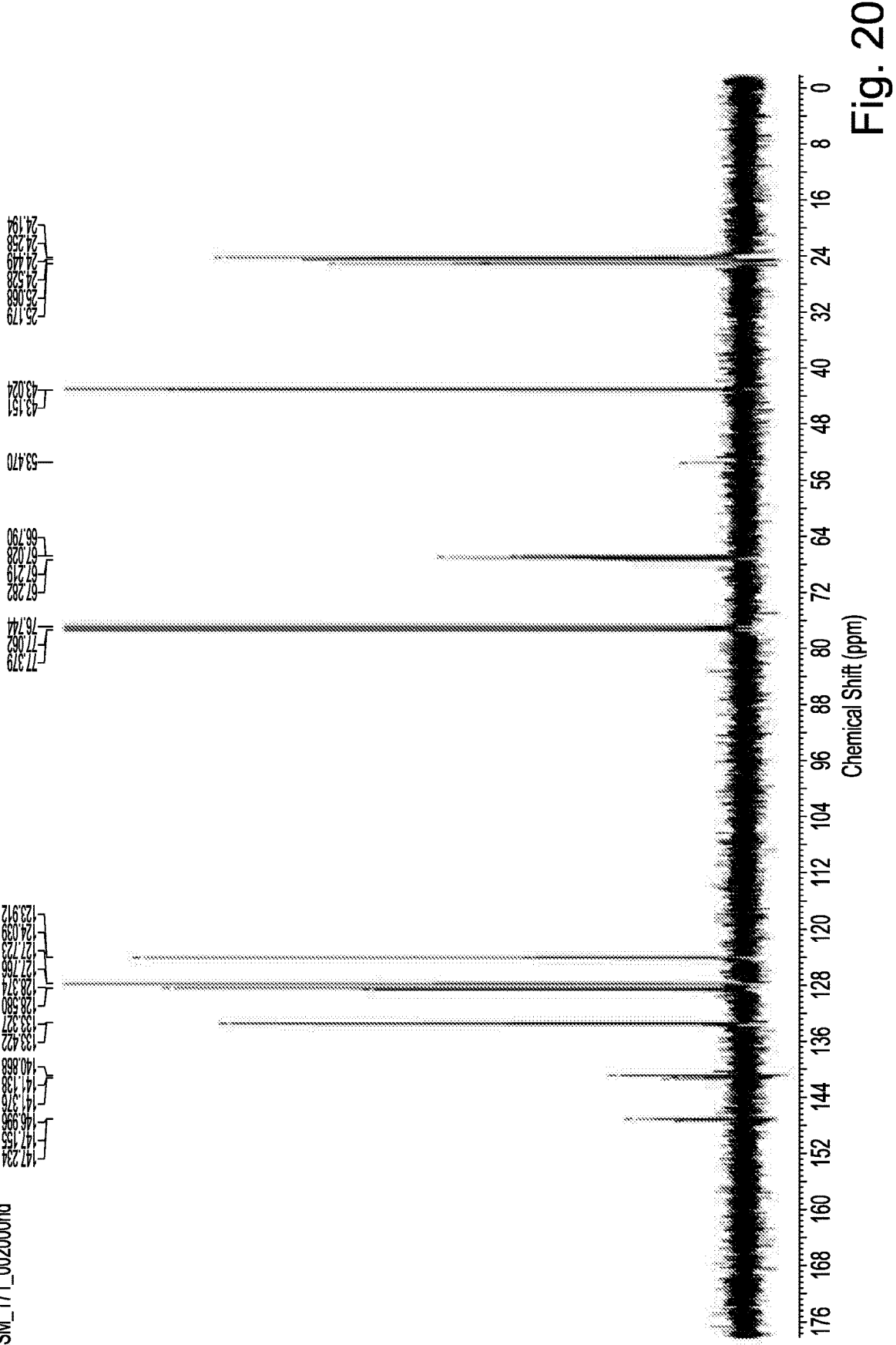
FIG. 20 shows the $^1$H and $^{13}$C NMR Spectra of compound 11.
Figure 21:
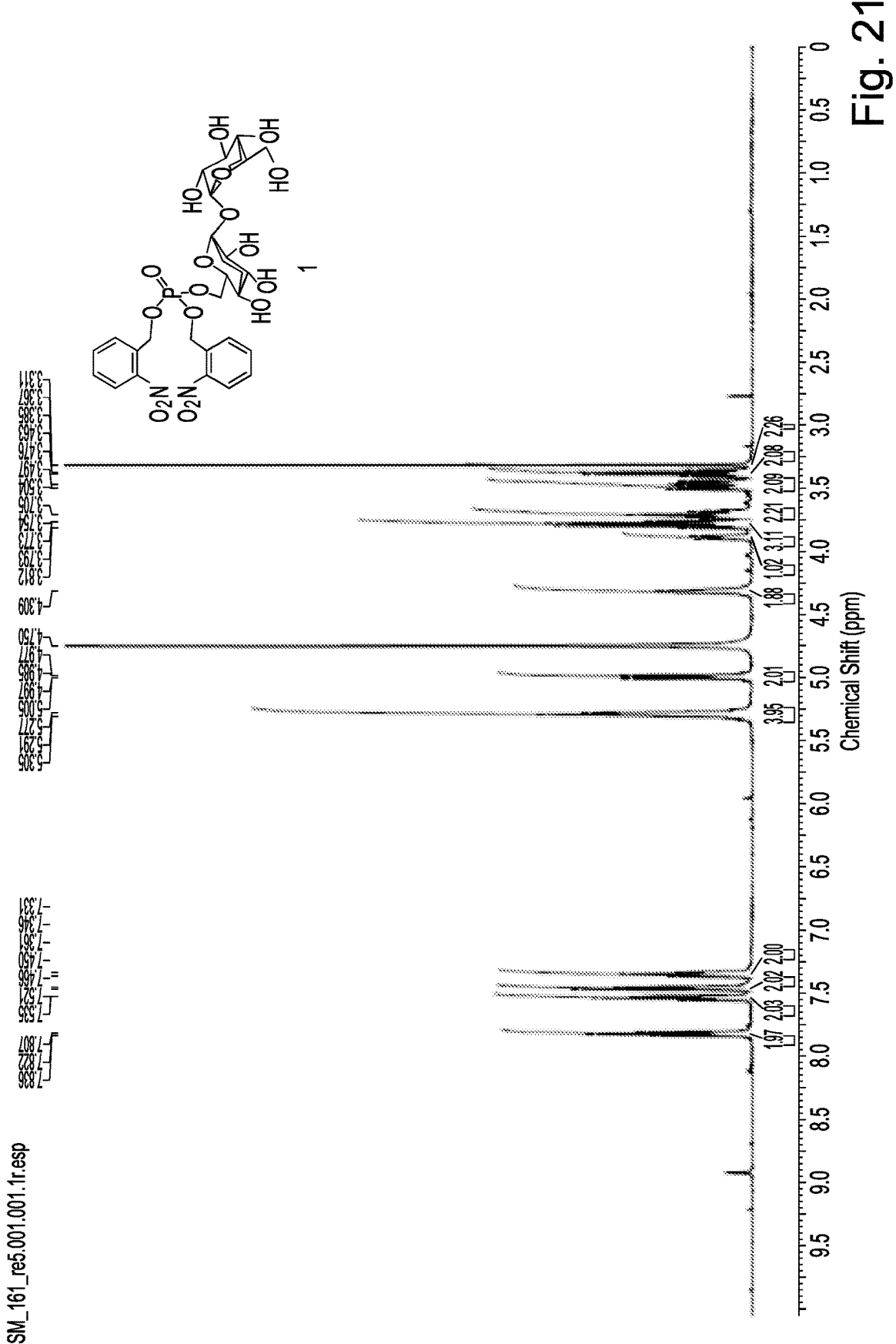
FIG. 21 shows the $^1$H and $^{13}$C NMR Spectra of compound 1.
Figure 22:
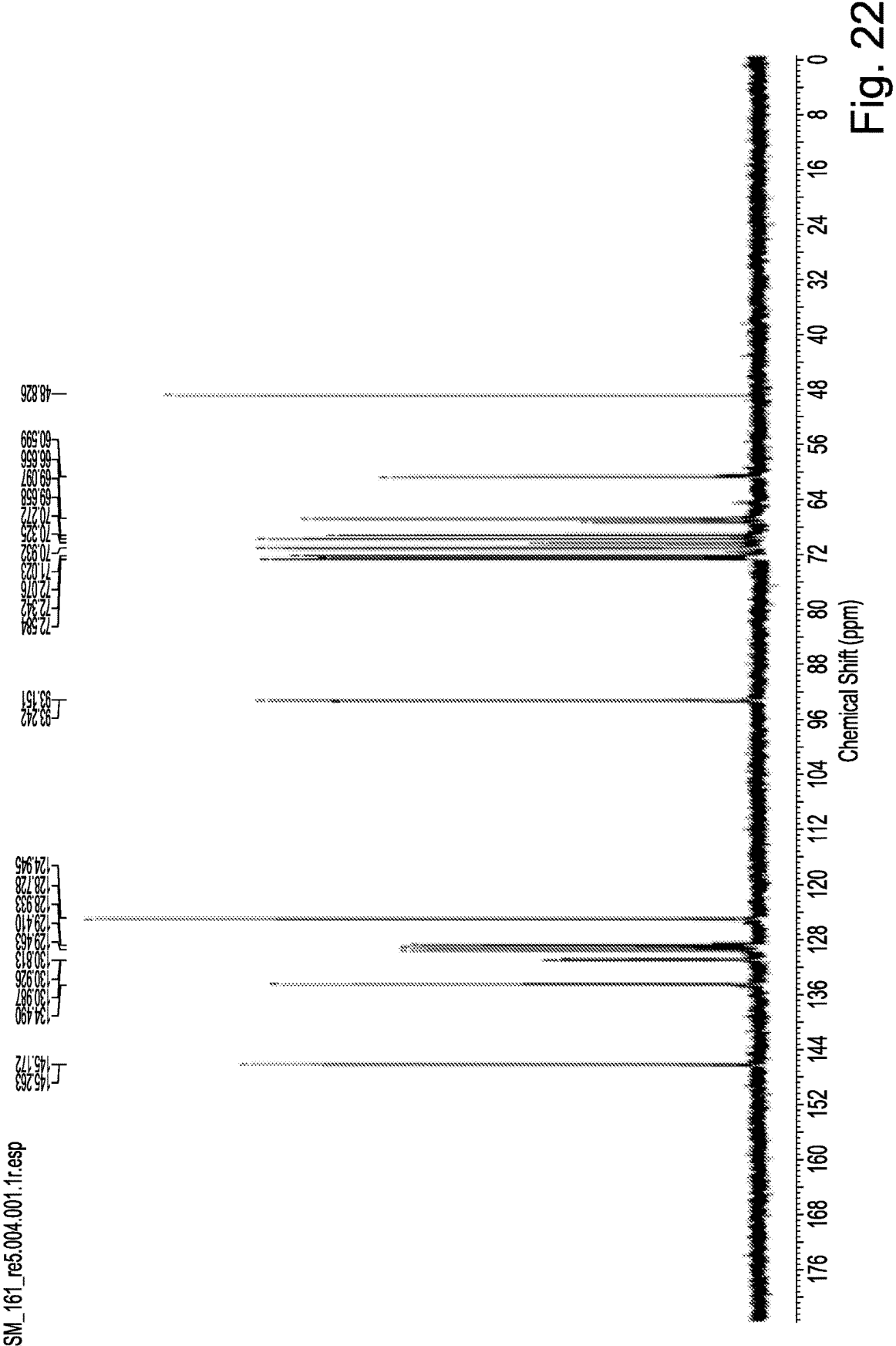
FIG. 22 shows the $^1$H and $^{13}$C NMR Spectra of compound 1.
Figure 23:
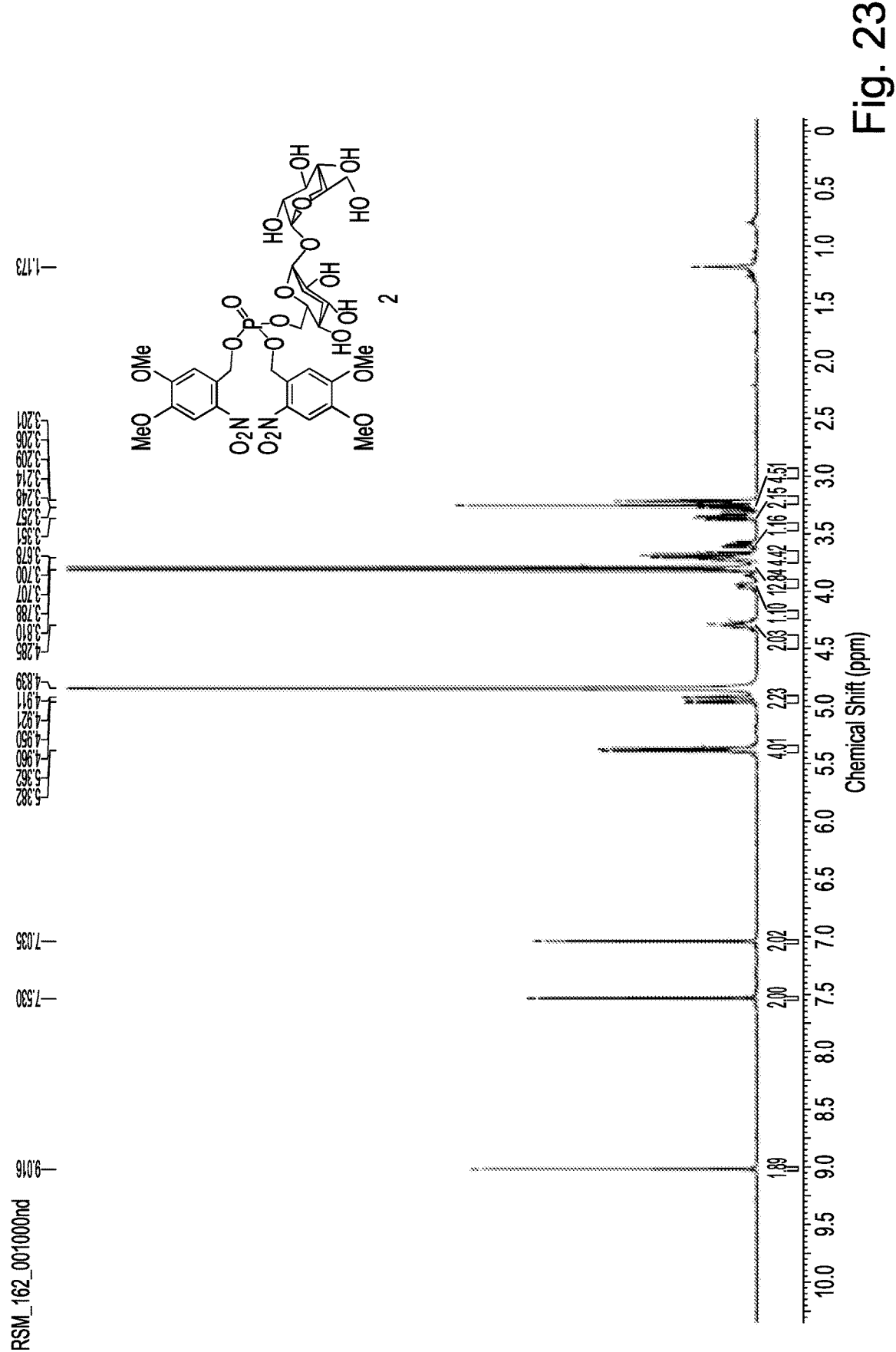
FIG. 23 shows the $^1$H and $^{13}$C NMR Spectra of compound 2.
Figure 24:
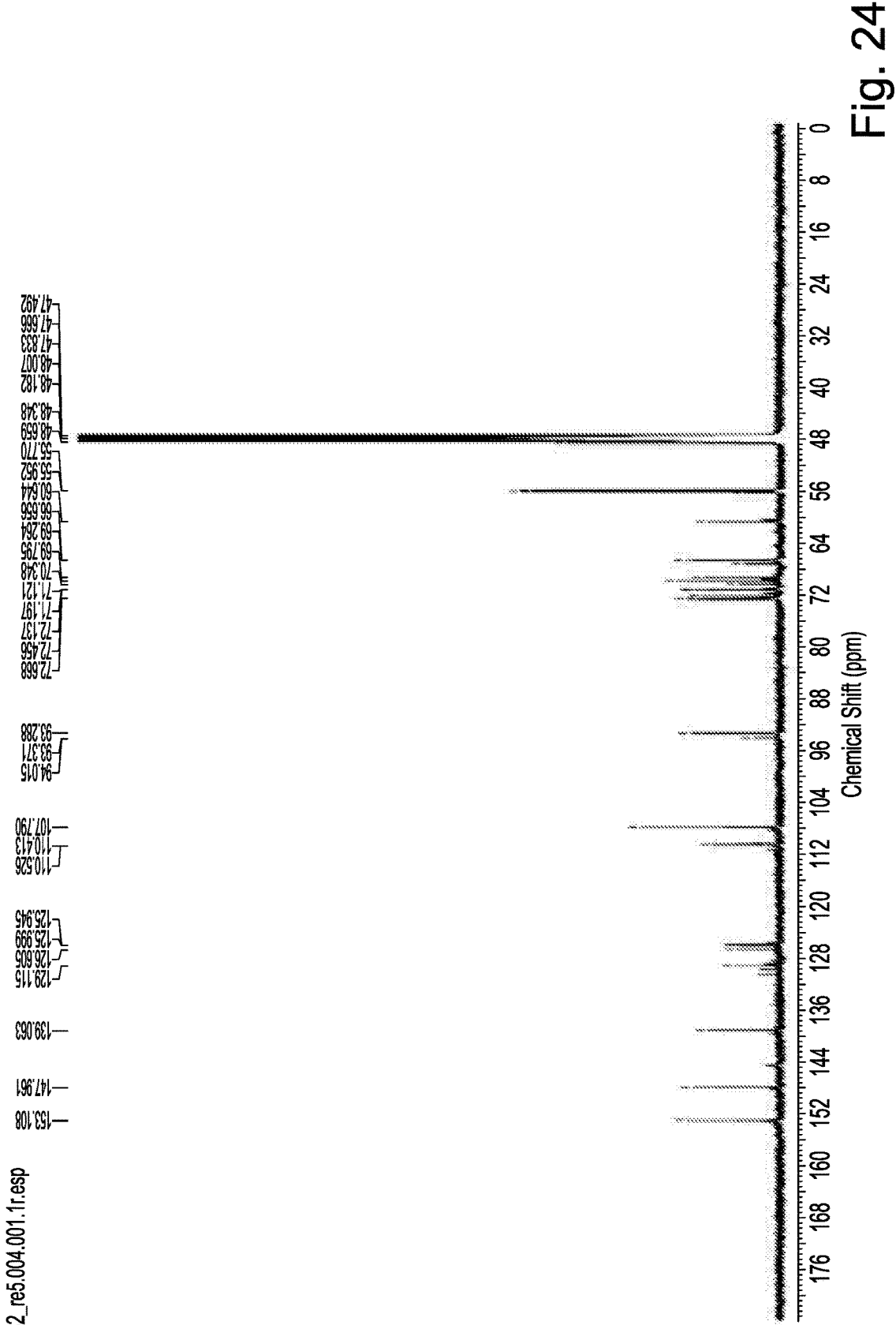
FIG. 24 shows the $^1$H and $^{13}$C NMR Spectra of compound 2.
Figure 25:
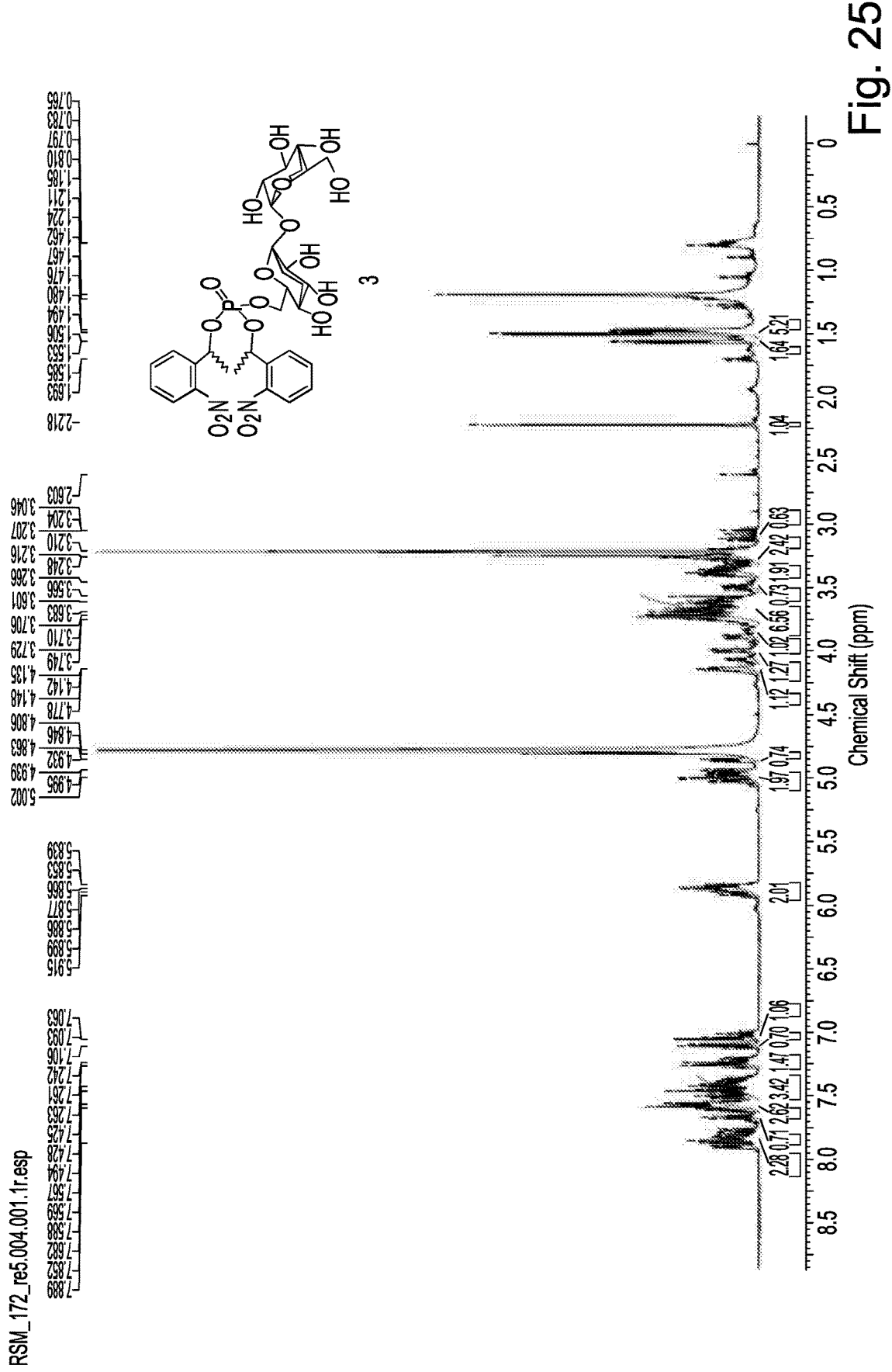
FIG. 25 shows the $^1$H and $^{13}$C NMR Spectra of compound 3.
Figure 26:
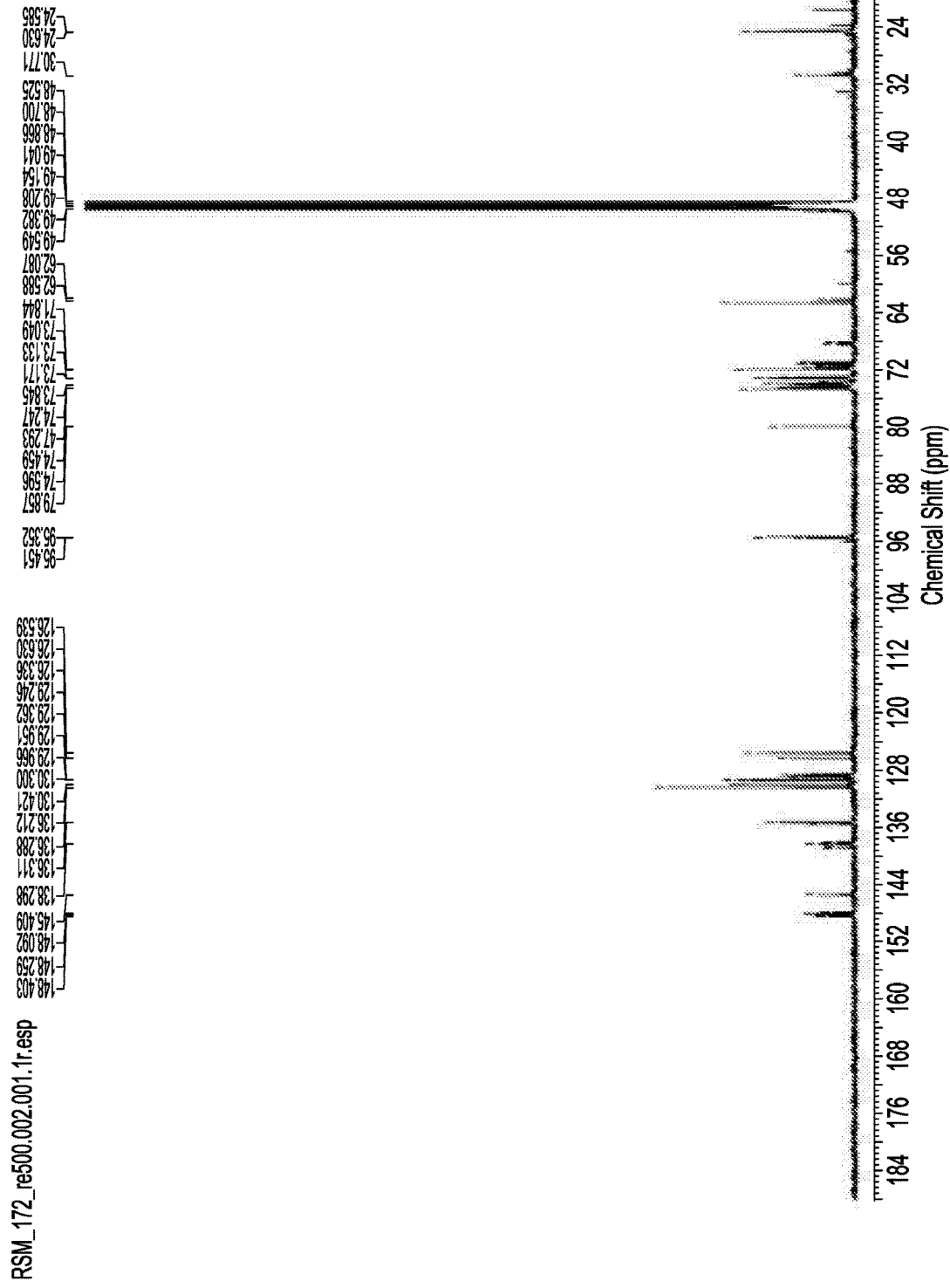
FIG. 26 shows the $^1$H and $^{13}$C NMR Spectra of compound 3.
Figure 27:
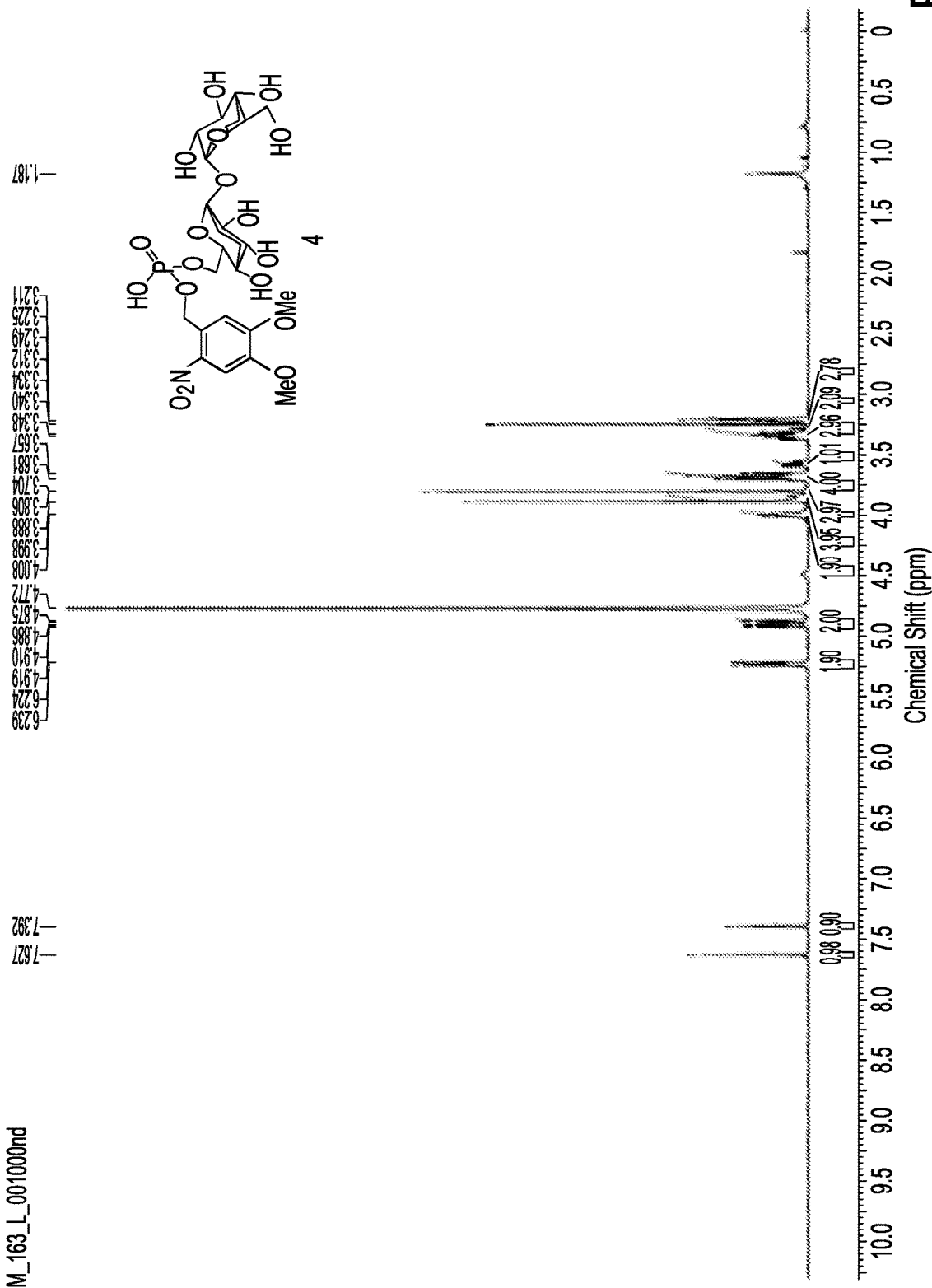
FIG. 27 shows the $^1$H and $^{13}$C NMR Spectra of compound 4.
Figure 28:
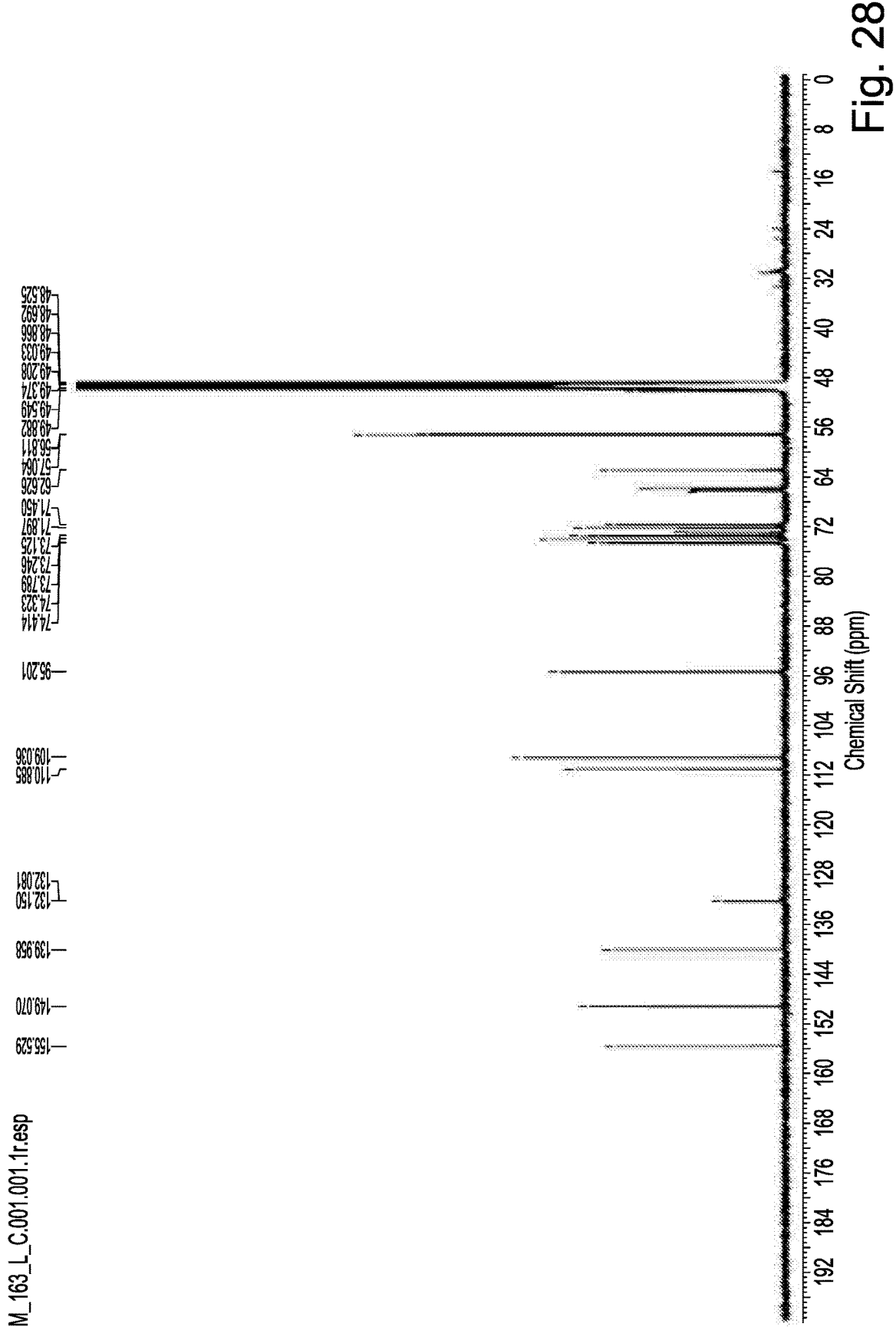
FIG. 28 shows the $^1$H and $^{13}$C NMR Spectra of compound 4.
Figure 29:
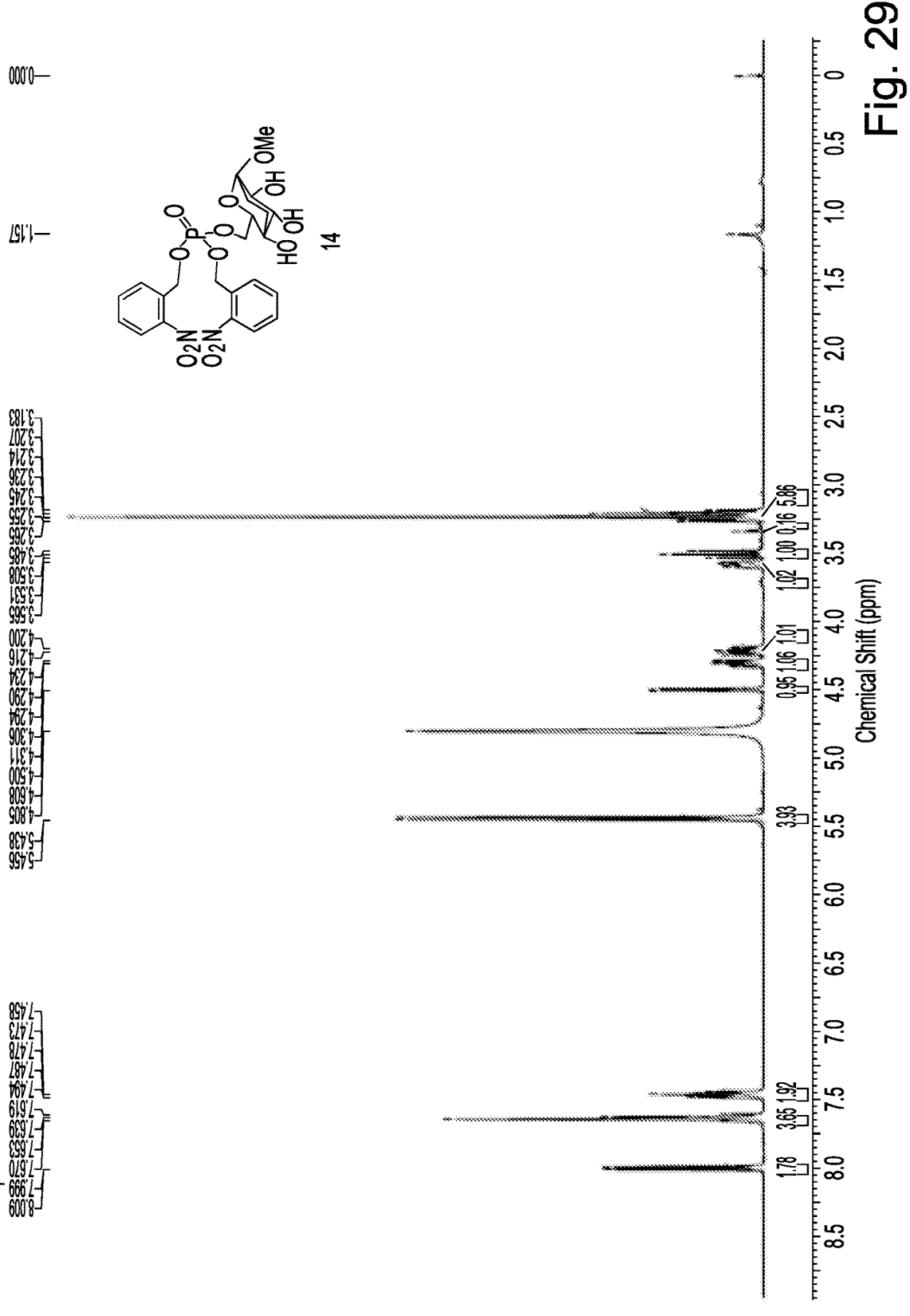
FIG. 29 shows the $^1$H and $^{13}$C NMR Spectra of compound 14.
Figure 30:
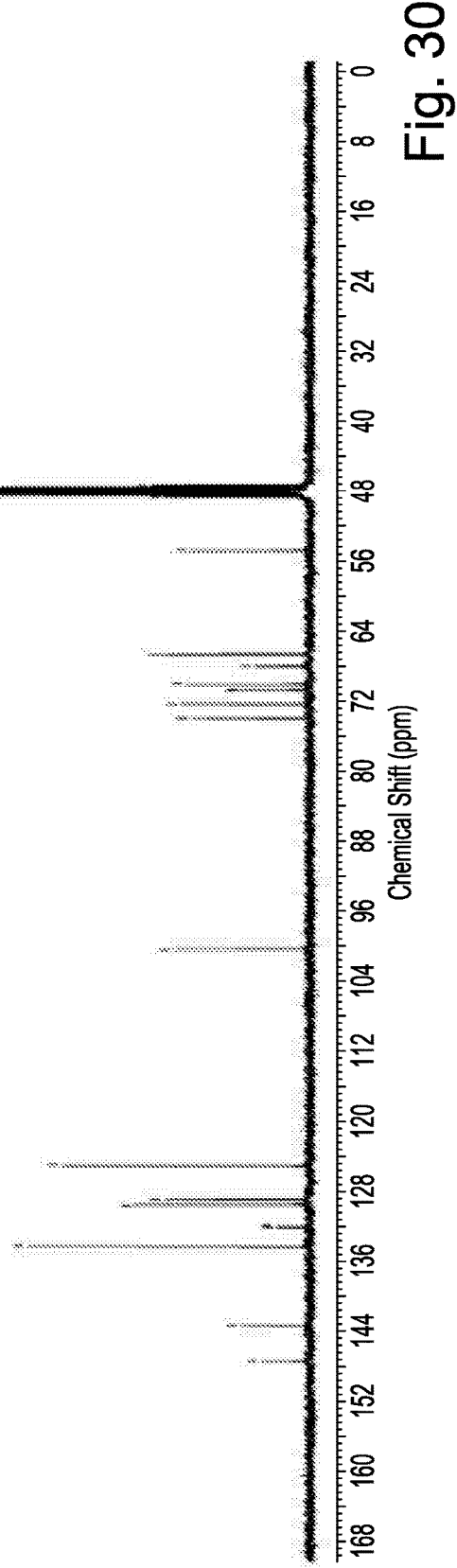
FIG. 30 shows the $^1$H and $^{13}$C NMR Spectra of compound 14.
Figure 31:
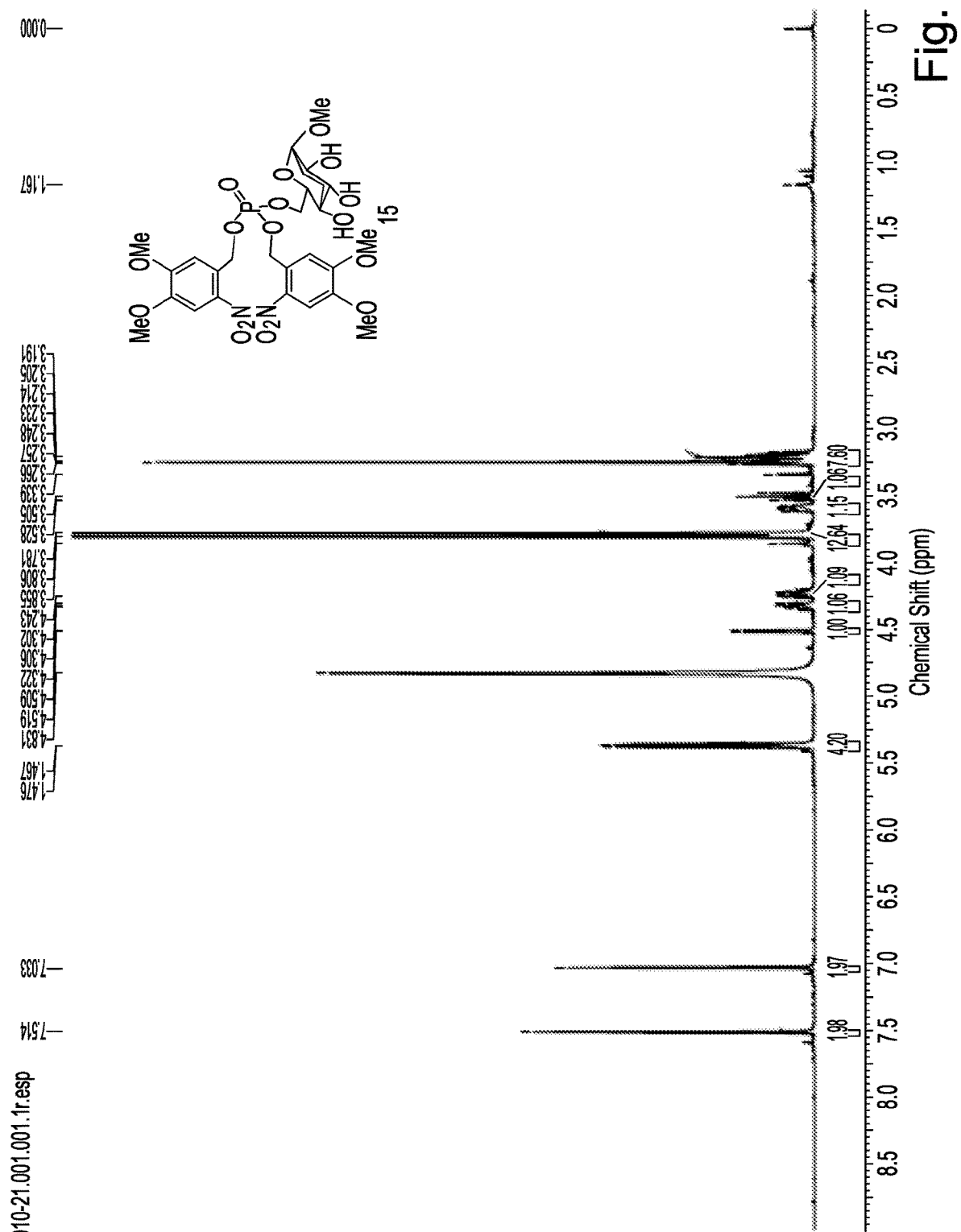
FIG. 31 shows the $^1$H and $^{13}$C NMR Spectra of compound 15.
Figure 32:
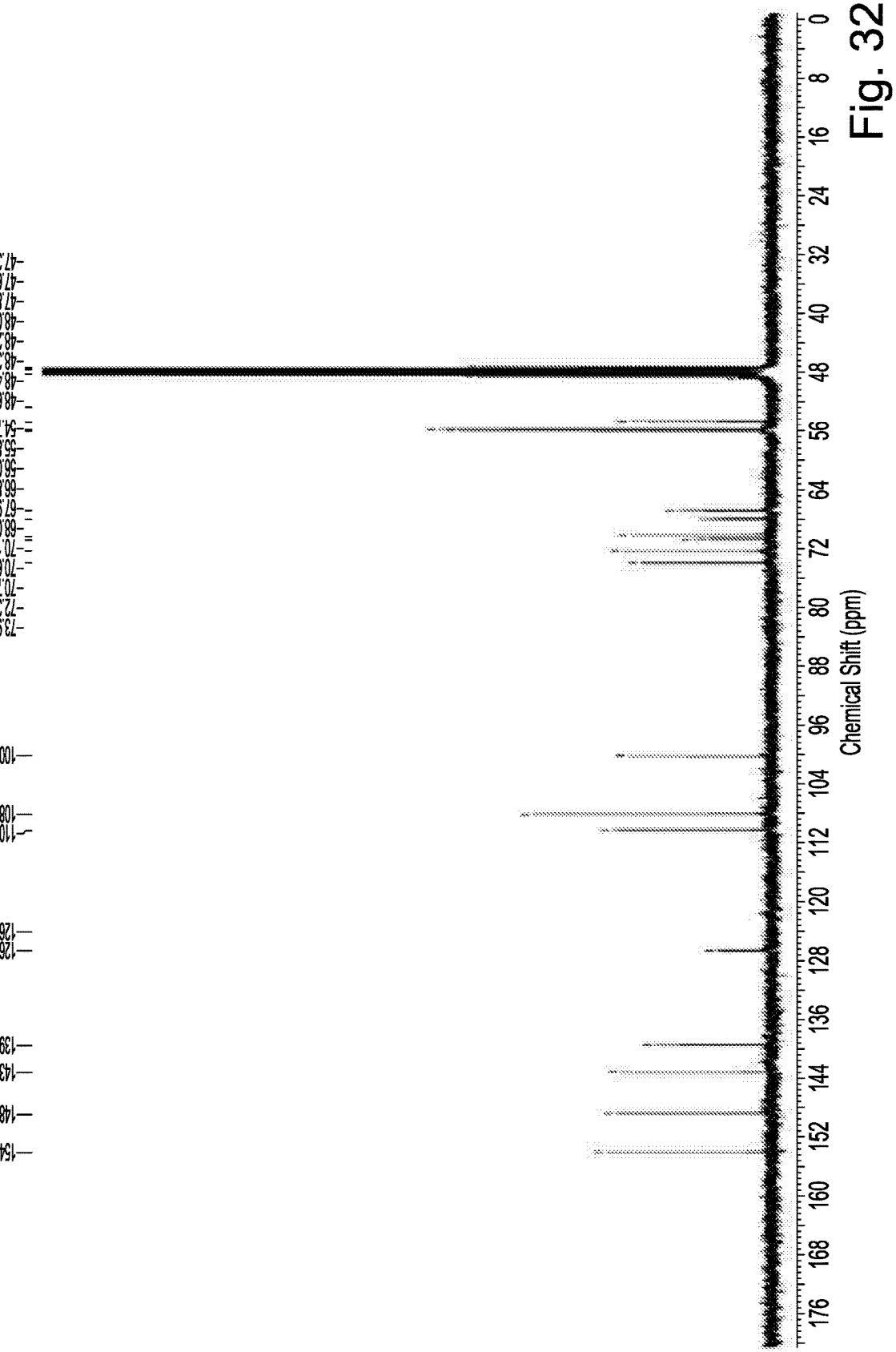
FIG. 32 shows the $^1$H and $^{13}$C NMR Spectra of compound 15.
Figure 33:
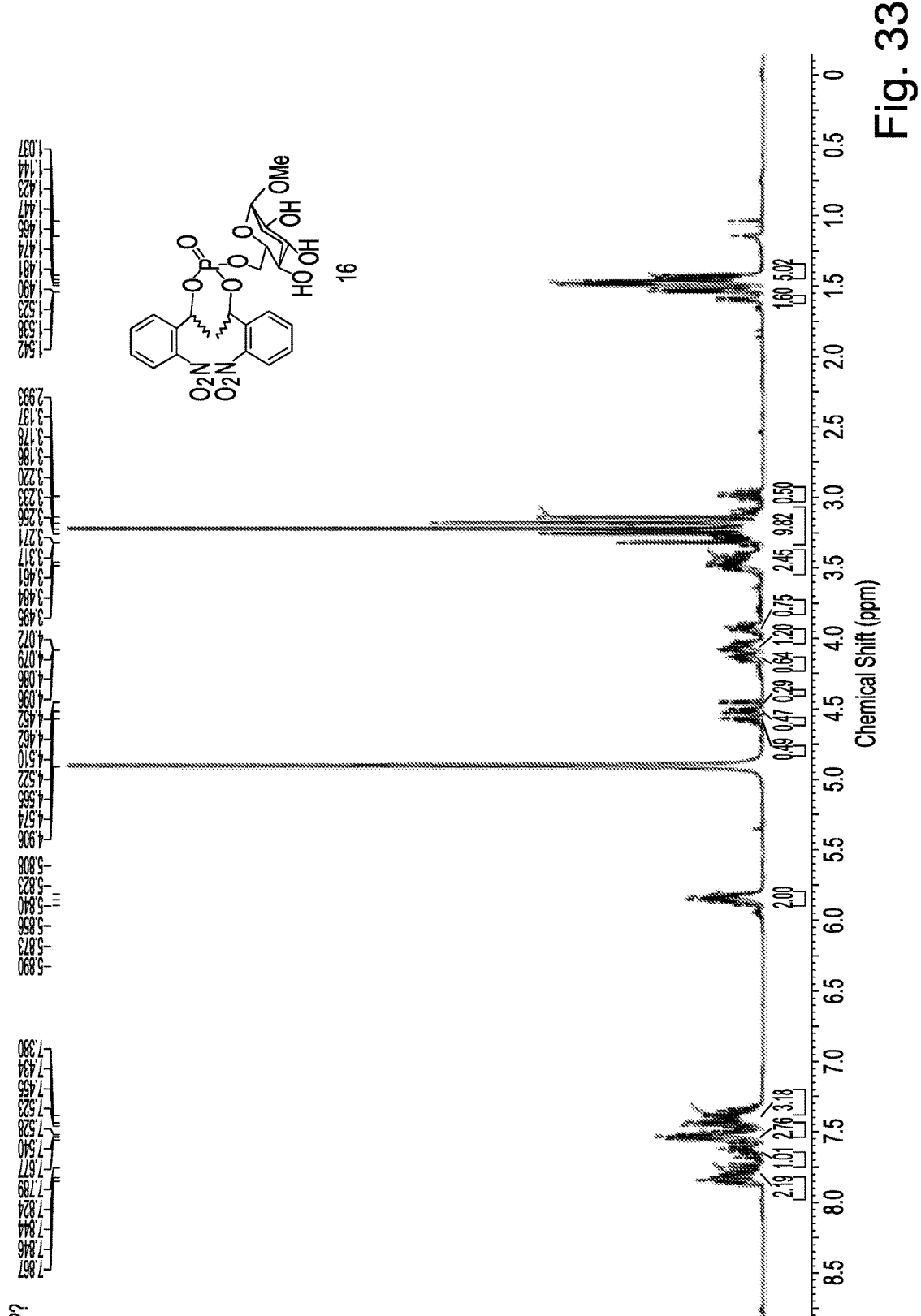
FIG. 33 shows the $^1$H and $^{13}$C NMR Spectra of compound 16.
Figure 34:
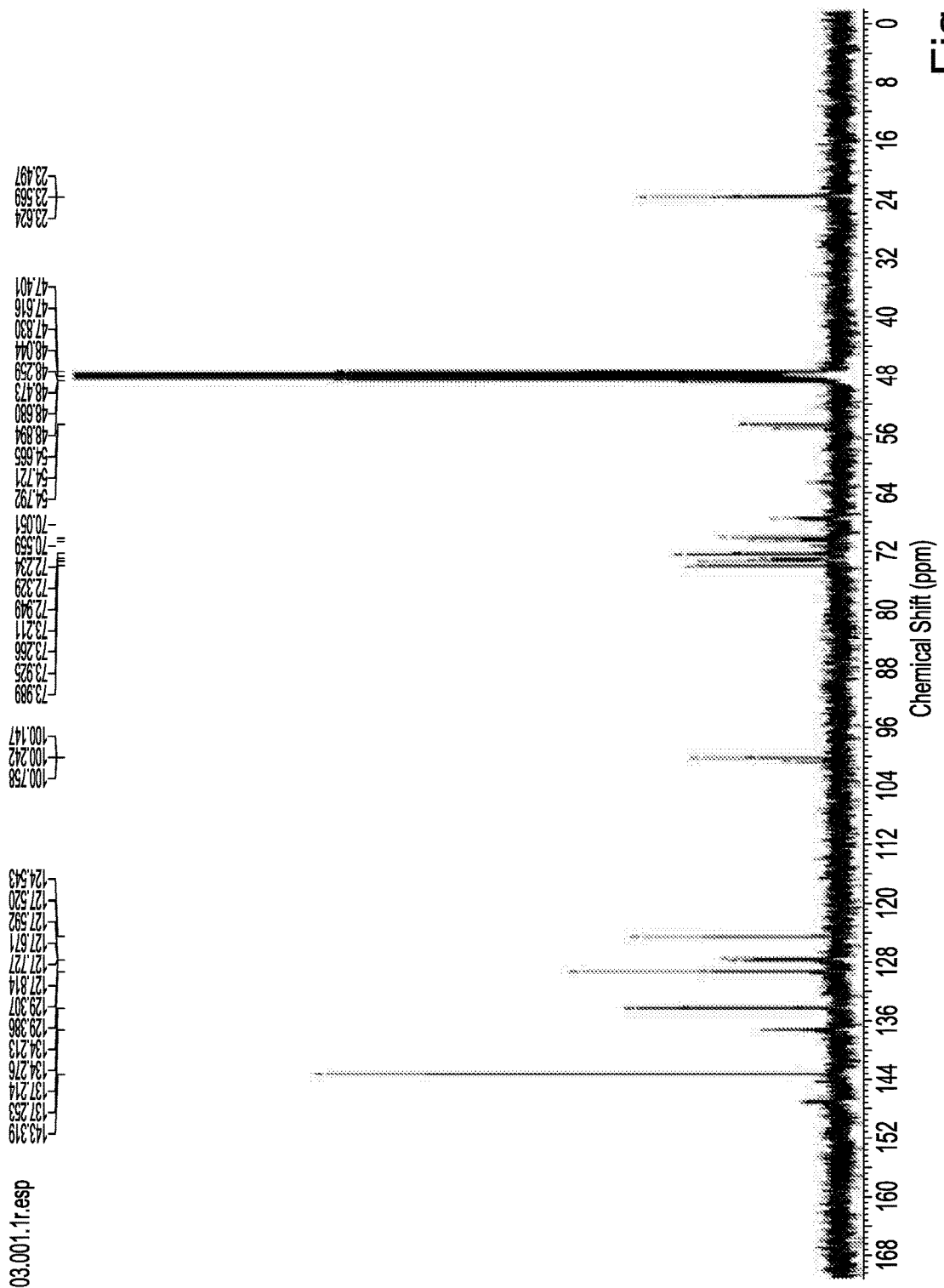
FIG. 34 shows the $^1$H and $^{13}$C NMR Spectra of compound 16.
Figure 35:
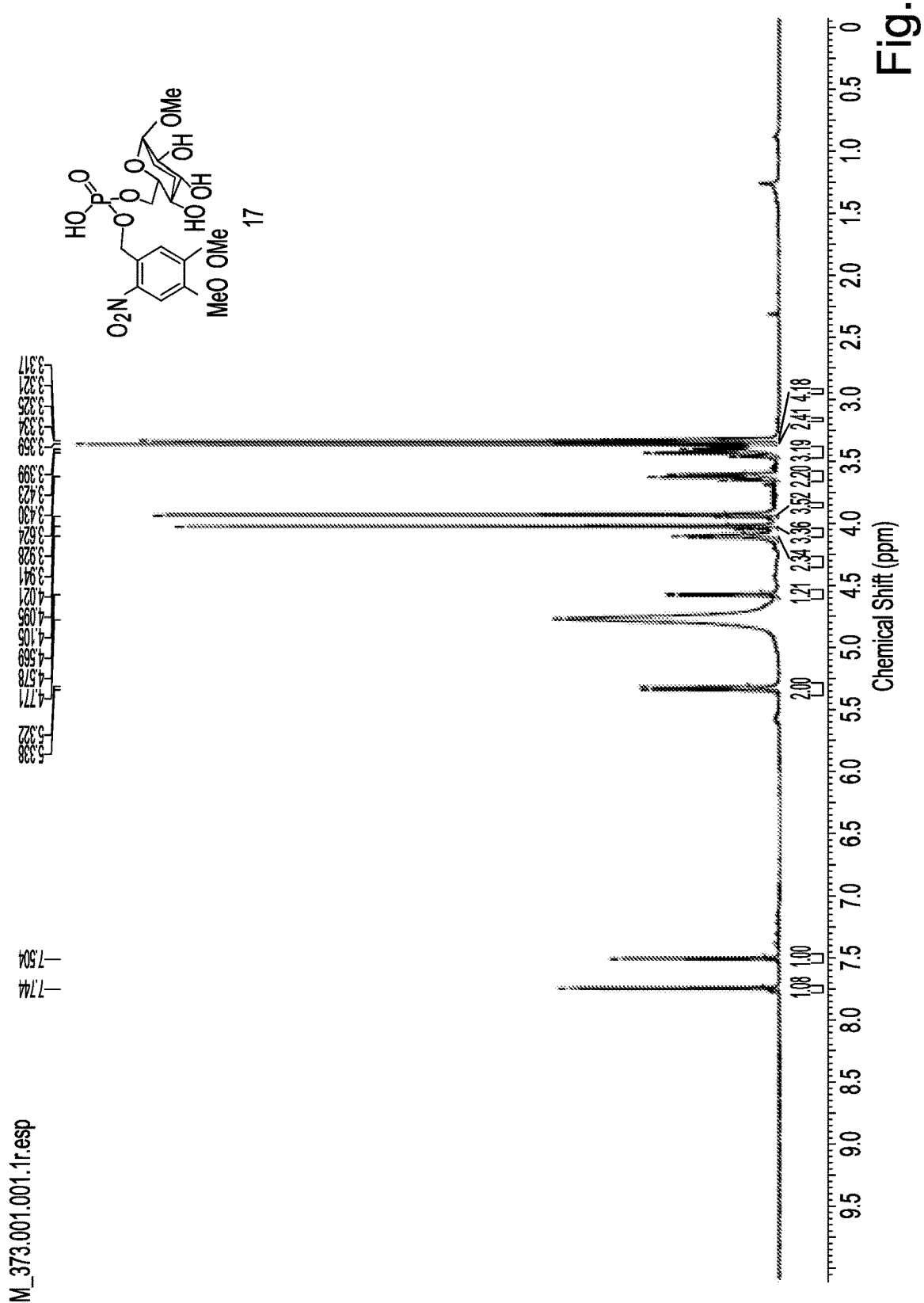
FIG. 35 shows the $^1$H and $^{13}$C NMR Spectra of compound 17.
Figure 36:
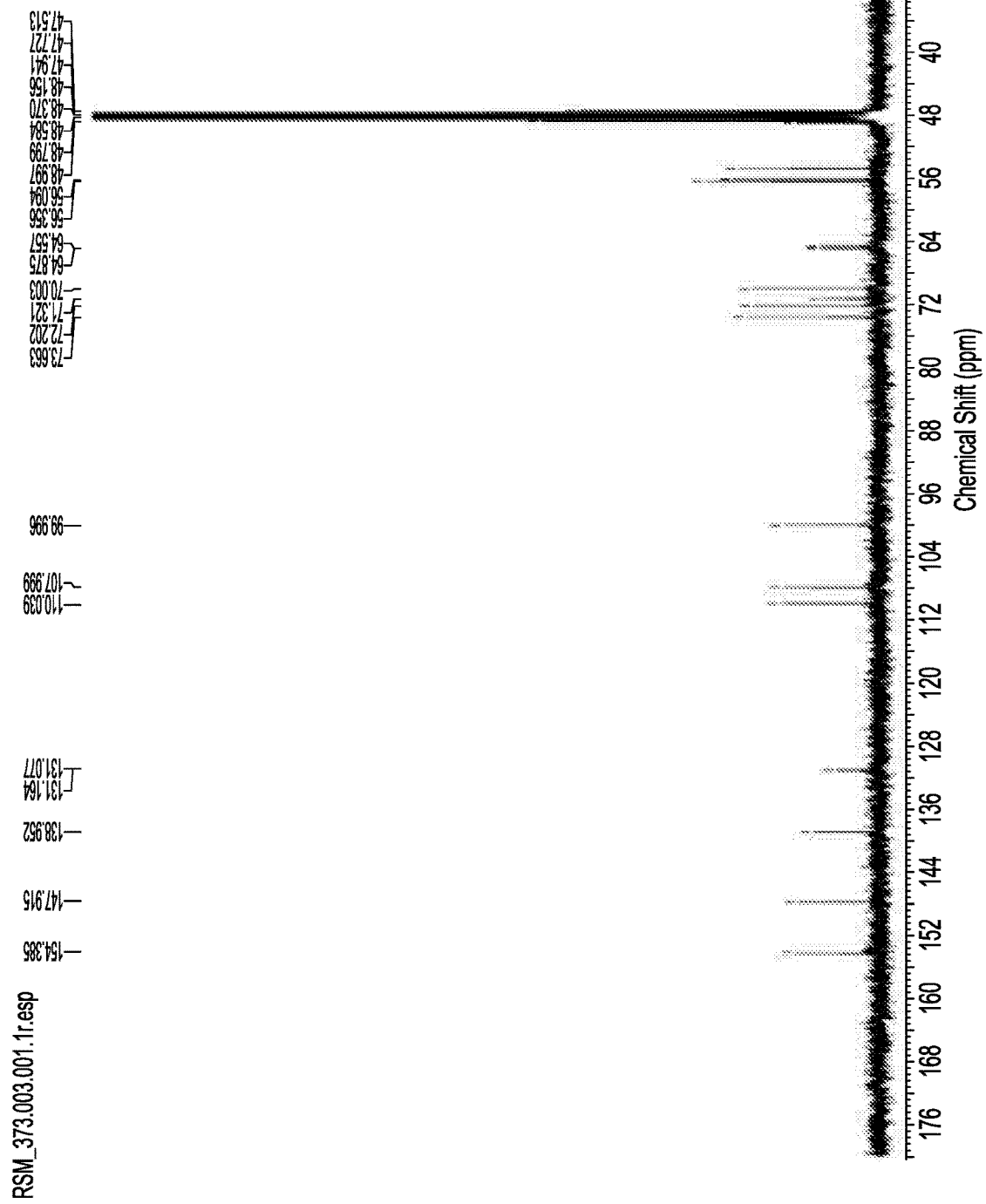
FIG. 36 shows the $^1$H and $^{13}$C NMR Spectra of compound 17.
Figure 37:
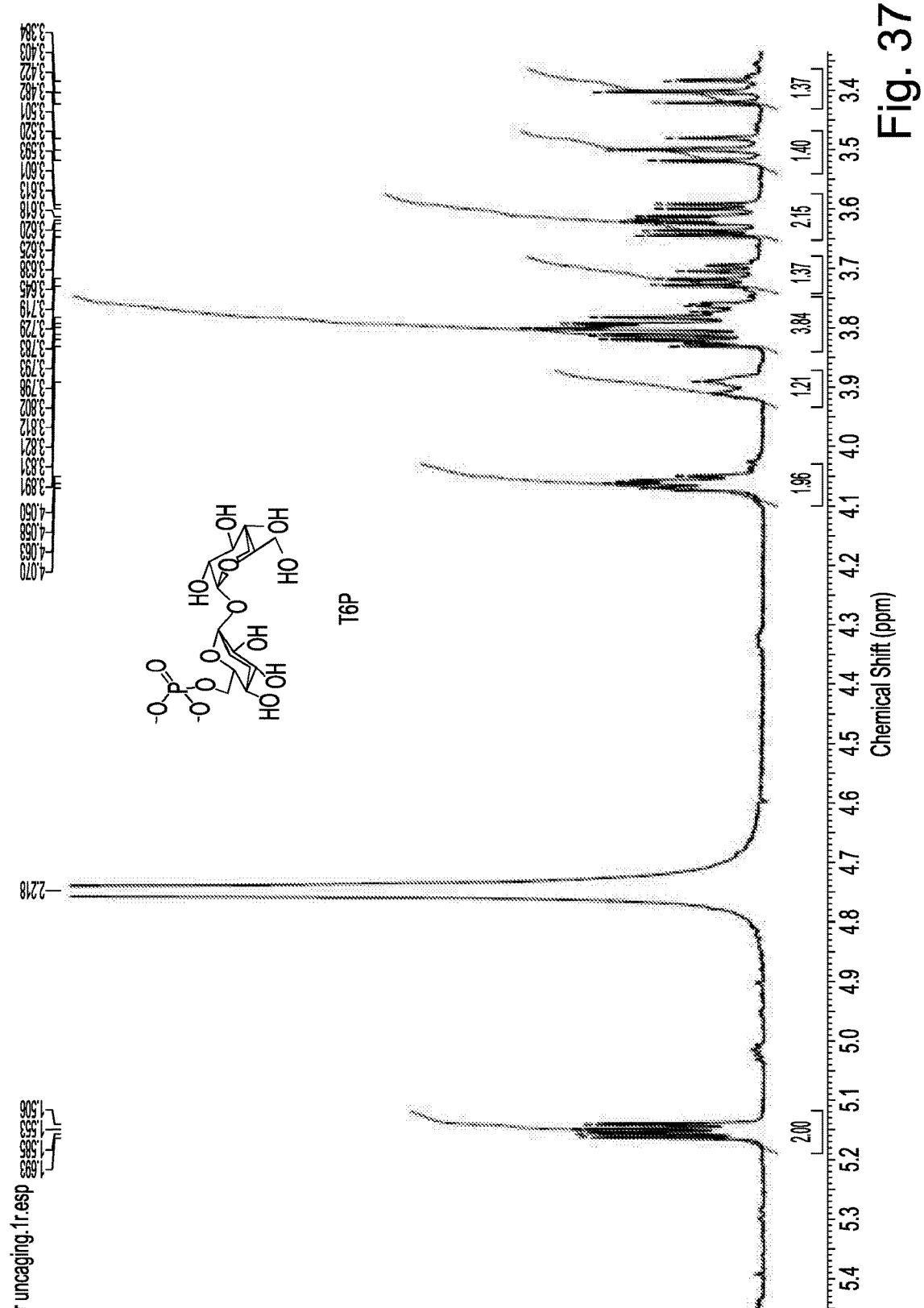
FIG. 37 shows the $^1$H and $^{13}$C NMR Spectra of compound T6P.
Figure 38:
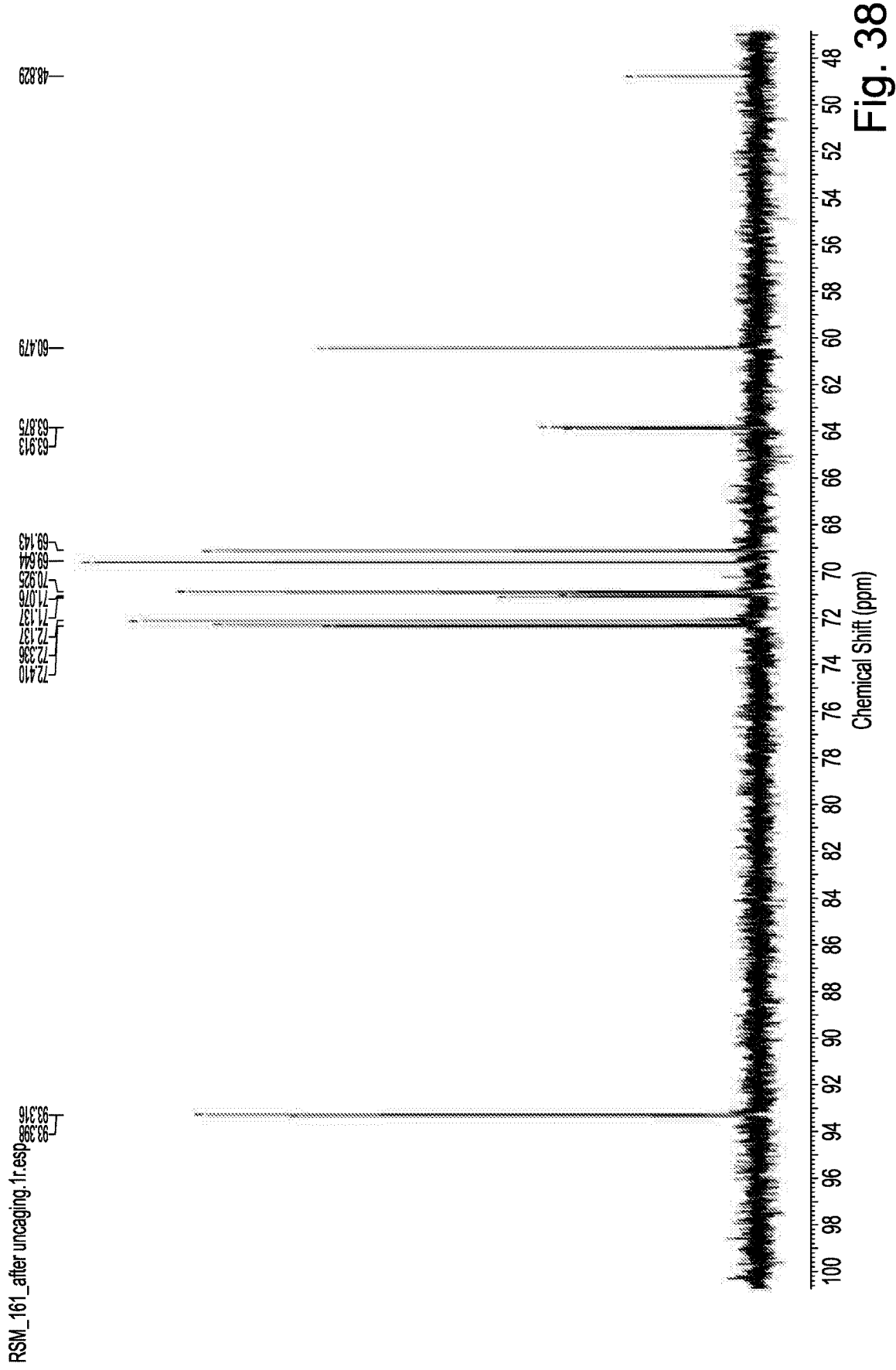
FIG. 38 shows the $^1$H and $^{13}$C NMR Spectra of compound T6P.
Figure 39:
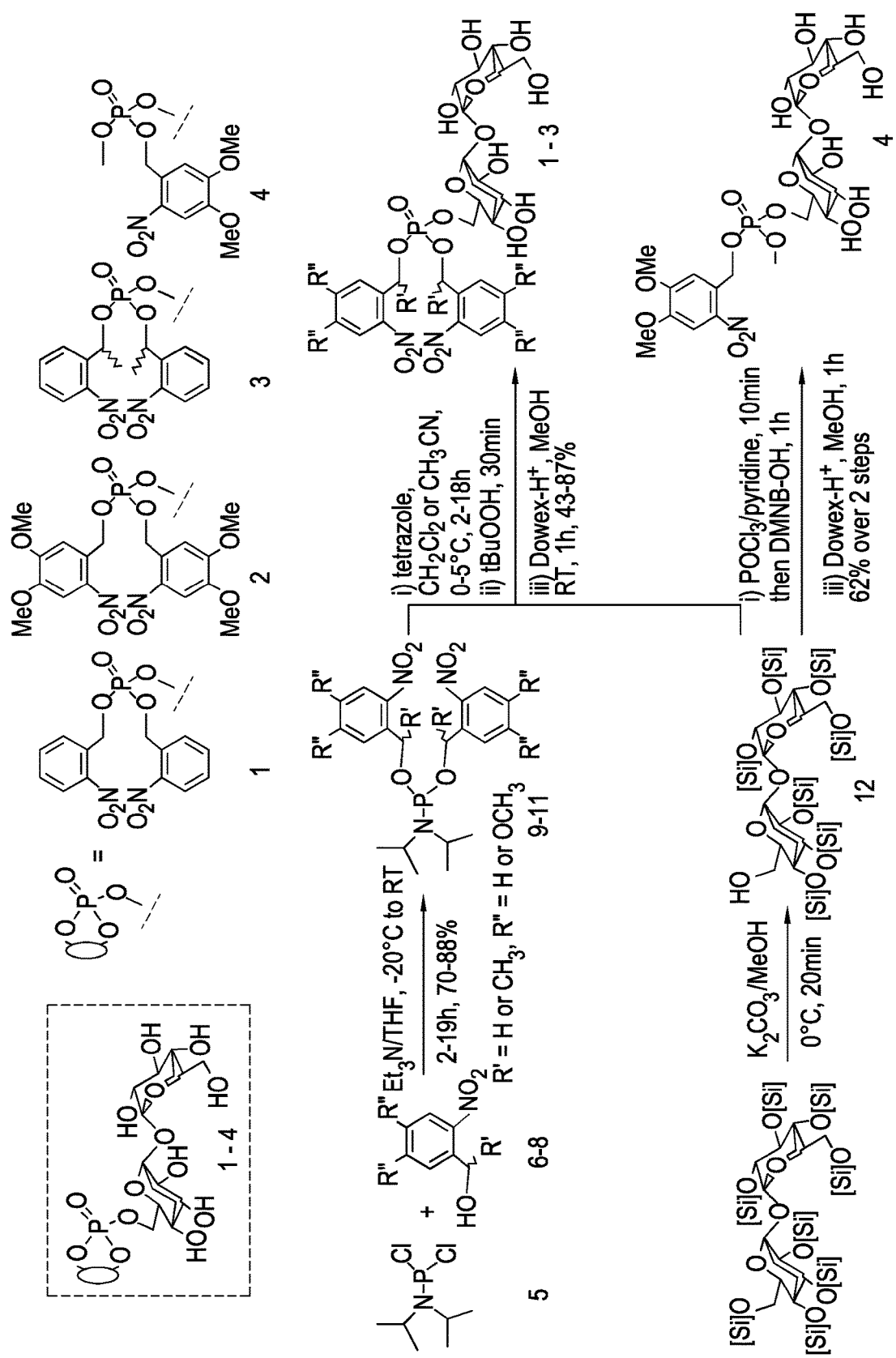
FIG. 39 shows the known biochemical structures and one-pot synthesis of designed permeable, signalling precursor variants from suitable precursors.

To a stirred solution of compound 13 (100 mg, 0.24 mmol) in pyridine (2 mL) at room temperature POCl$_3$ (0.024 mL, 0.26 mmol) was added and the mixture stirred. After 10 min, 4,5-dimethoxy-2-nitrobenzyl alcohol (153.4 mg, 0.72 mmol) was added and the reaction mixture was left stirring at the same temperature for 1 h. The reaction mixture was then concentrated in vacuo to yield crude product mixture, which after treatment with Dowex-H$^+$ resin (50 mg) in methanol (2 mL) furnished compound 15 and 17. Filtration, concentration in vacuo and flash chromatography purification yielded compound 17 (55 mg, 48%) as a pure solid. (see FIG. 14)

Methyl 6-O-(4,5-dimethoxy-2-nitrobenzyloxyphosphoryl)-α-D-glucopyranoside 17

R$_f$ 0.35 (1 water:2 isopropanol:4 ethyl acetate): [α]$_D^{21}$+ 38.9 (c 0.64, MeOH), FT-IR (ATR) v cm$^{-1}$ 3319 (br OH), 1521 (s, N=O), 1326 (s, N=O), 1220 (P=O); $^1$H NMR (400 MHz, CD$_3$OD): δ 7.74 (s, 1H, ArH), 7.50 (s, 1H, ArH), 5.33 (d, J=6.4 Hz, 2H, CH$_2$Ar), 4.57 (d, J$_{1,2}$=3.6 Hz, 1H, H-1), 4.02 (s, 3H, OMe), 3.92 (s, 3H, OMe), 3.64-3.60 (m, 2H, H-6), 3.42 (dd, J$_{5,4}$=9.6 Hz, J$_{5,6b}$=2.8 Hz, 1H, H-5), 3.40 (brt, J$_{3,2}$=9.2 Hz, J$_{3,4}$=9.2 Hz, 1H, H-3), 3.39 (dd, J$_{2,3}$=9.6 Hz, J$_{2,1}$=3.0 Hz, 1H, H-2), 3.32 (s, 3H, OMe), 3.32-3.31 (m, 1H, H-4); $^{13}$C NMR (400 MHz, CD$_3$OD): δ 154.3, 147.9, 138.9, 131.1, 110.0, 107.9 (ArC), 100.0 (C-1), 73.6 (C-3), 72.2 (C-2), 71.3 (C-5), 70.0 (C-4), 64.8 (C-6), 64.5 (CH$_2$Ar), 56.3 (OMe), 56.0 (OMe), 54.8 (OMe); $^{31}$P NMR (162 MHz, CD$_3$OD) δ 0.66; ESI-HRMS m/z calculated for C$_{16}$H$_{24}$NO$_{13}$P [M−H]$^-$: 468.0907; Found 468.0905.

The $^1$H and $^{13}$C NMR. Spectra of all compounds are shown in FIGS. 15-38.

The signalling-precursor strategy was based on release by light (FIG. 2). Light-activated control is a potent strategy in biology because it can allow temporal and even spatial resolution that surpasses that of standard genetic methods (Mayer and Heckel, 2006, Angew Chem Int Ed Engl 45: 4900-4921). In principle, this resolution can be increased yet further when combined with small molecule chemical control given these too can be applied with localization and at predetermined time points (Adams and Tsien, 1993, Annu Rev Physiol 55: 755-784; Givens and Kueper, 1993, Chem. Rev. 93, 55-66; Ellis-Davies, 2007, Nat Methods 4: 619-628). The potency of such a method is increased further still when it leads to the release of a signalling molecule whose effect is amplified several fold. Notably, however, no such light-controlled approaches have, until now, been applied to sugar biology.

Figure 3:
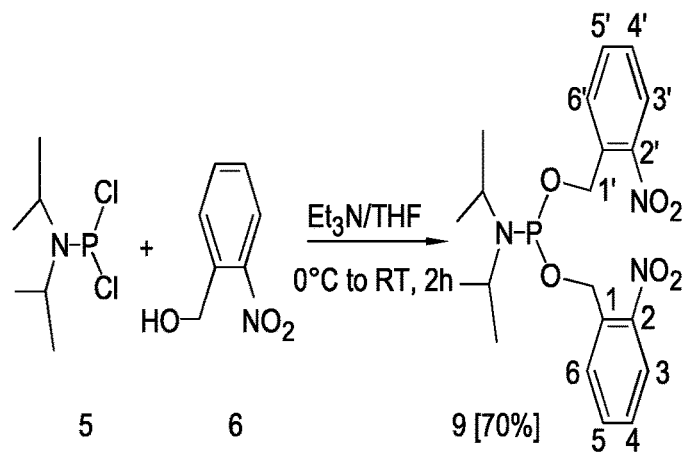
FIG. 3 shows the synthesis of bis-(2-nitrobenzyl)-N,N-diisopropylphosphoramidite 9.

Additionally, hydrophilic sugar molecules or charged molecules do not readily cross into plants unless actively transported. It was hypothesised that unnatural precursors could be designed that contain groups that would both mask charge/increase hydrophobicity and also be released by light. Four water-soluble precursors (1-4) of T6P were selected (FIG. 3). Each contained different light-sensitive moieties that functionally encapsulated T6P in an inactive and neutral form to facilitate entry into cells and that would then be liberated into active molecule upon irradiation with light: ortho-nitrobenzyl (oNB) in 1; 4,5-dimethoxynitrobenzyl (DMNB) in 2 and 4 and 2-(ortho-nitrophenyl)ethyl (oNPE) in 3. These differing groups were intended to permit the generation of create precursors with different behaviours in light and to fine-tune both uptake and release through change of both physical and chemical properties.

Construction of the precursors (FIG. 3) used different phosphorus chemistries: phosphoramidite chemistry (Scheigetz and Roy, 2000, Synth. Commun. 30: 1437-1445; Arslan, et al., 1997, J. Am. Chem. Soc. 119: 10877-10887) to create P(III) intermediates that were then oxidized to corresponding P(V) phosphotriester intermediates or direct P(V) phosphorylation chemistry (FIG. 3). Regioselective access to the OH-6 group in trehalose was achieved through the use of trimethylsilyl (TMS) as a protecting group to form corresponding ethers. The TMS ether is chemically orthogonal to the phosphotriester group found in each of the light-sensitive moieties and its removal under mildly acidic conditions was successfully achieved. This was important since phosphate esters are highly prone to migration under basic conditions (Billington, 1989, Chem. Soc. Rev. 18: 83-122). Thus, intermediate 12 was prepared in gram quantities by regioselective removal of an 0-6 TMS ether group on persilylated trehalose (Ronnow et al., (1994) Carbohydr. Res. 260: 323-328). Overall phosphorylation of the revealed OH-6 hydroxyl in 12 involved reaction with phosphoramidites 9-11 (Scheigetz and Roy, 2000, Synth. Commun. 30: 1437-1445; Arslan, et al., 1997, J. Am. Chem. Soc. 119: 10877-10887) followed by in situ oxidation using tBuOOH. Using alternative direct P(V) chemistry a variant containing only a single DMNB was also created to explore the effect of different copy numbers of light-sensitive moieties; 12 was treated with 1 equiv. of POCl3 in pyridine (Meldal et al., (1992) Carbohydr. Res. 235: 115-127) followed by the addition of DMNB alcohol. Finally, all of the resulting intermediates were stirred in methanol in the presence of Dowex-H+ to induce mild deprotection which furnished the corresponding signalling precursors 1-4 (see SI). This synthetic route proved efficient and effective, allowing preparation of grams of signalling precursors at scales for application in plant trials (vide infra).

Example 2. Signalling Precursor Application to Water Stressed Wheat Plants

Spring wheat (Triticum aestivum Cadenza) seeds were sown in Rothamsted Prescription Compost Mix (75% medium grade (L+P) peat, 12% screened sterilised loam, 3% medium grade vermiculite, 10% grit (lime-free), 3.5 kg Osmocote Exact 3-4 month/m$^3$ (Scott's UK Professional, Ipswich, Suffolk, www.scottinternational.com), 0.5 kg PG mix/m$^3$ (Hydro Agri Ltd., Immingham, UK), Wetting agent and Lime) and grown in controlled environment conditions with a photoperiod of 16 hours light, 8 hours dark, day/night temperatures of 20° C./16° C., photon flux density of 600 μmol m$^{-2}$ s$^{-1}$, and ambient relative humidity. Once the plants had reached Feekes stage 4, water was withheld for 10 days. On the 9th day, 30 ml 1 mM solutions of oNPE-T6P and DMNBT6P were applied to all above-ground biomass, on the 10th day the watering schedule was reinstated. Plants were harvested to measure biomass production every 5 days for 30 days after watering was reinstated. Both experiments were completed in replicates of 6.

vi) Statistical Methods

Analysis of Variance (ANOVA) was applied to data to test for differences between treatments. A natural log transformation was used where necessary to ensure constant variance. The GENSTAT statistical system was used for this analysis (2011, 14th edition, ©VSN International Ltd, Hemel Hempstead, UK).

Figure 40:
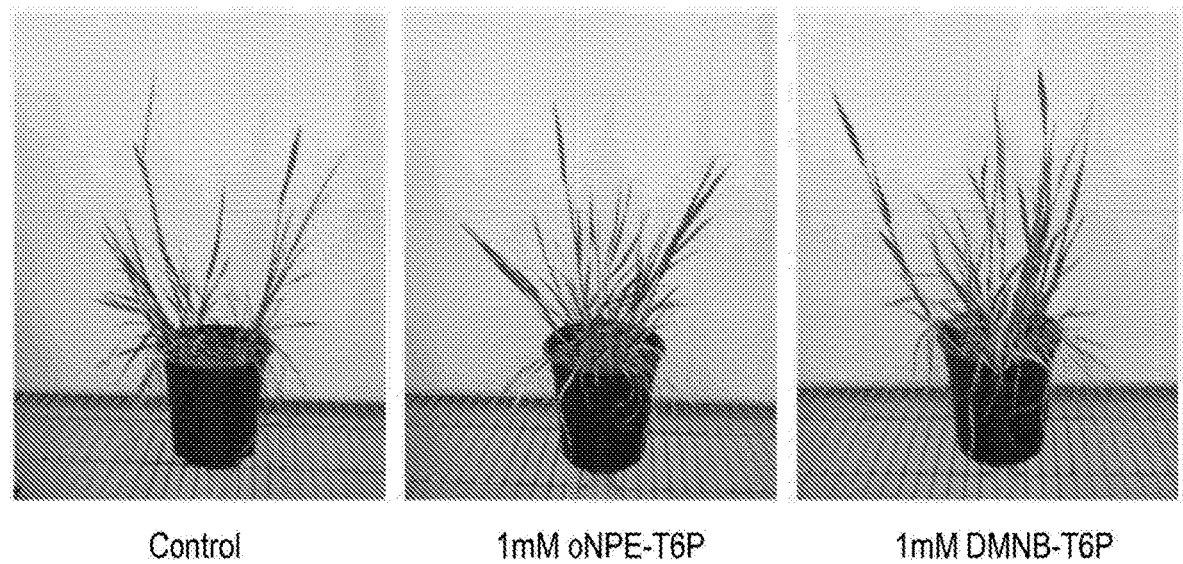
FIG. 40 shows the effect of spraying T6P signalling precursors on crop resilience; overall phenotypes of plants after one application of 1 mM oNPE-T6P (3) or 1 mM DMNB-T6P (2) one day prior to re-watering after 20 days recovery.
Figure 41:
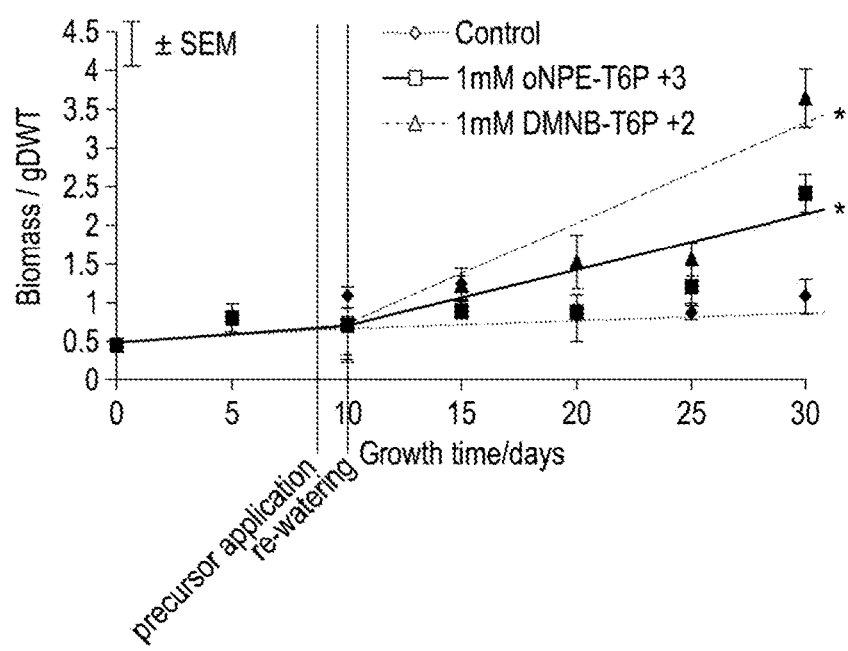
FIG. 41 shows the biomass from the experimental plants of FIG. 4. Asterisks indicate statistical significance.

The effect of the signalling precursors upon plant resilience and recovery were tested. The results are shown in FIGS. 40-43. Drought is still the biggest global factor that limits crop yields, even in developed countries, such as the UK (Boyer, 1982, Science 218: 443-448). When 4-week-old wheat plants were sprayed with DMNB-T6P 2 or oNPE-T6P 3 (30 mL of 1 mM, once only) after 9 days of drought and then regrowth measured (recovery response) following resumption of watering 1 day after the initial chemical treatment, the effects were dramatic (FIGS. 40 and 41).

Figure 42:
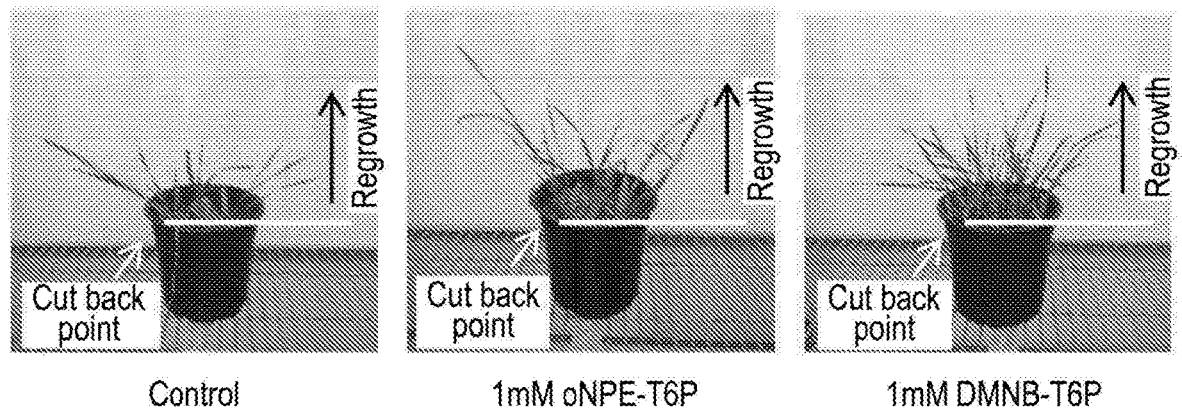
FIG. 42 shows overall phenotypes of plants after one application of 1 mM oNPE-T6P (3) or 1 mM DMNB-T6P (2) one day prior to re-watering, cut at 5 days after re-watering, and left to regrow for 10 days. Cut back point is indicated by white arrow and line. Regrowth is indicated by black arrow.
Figure 43:
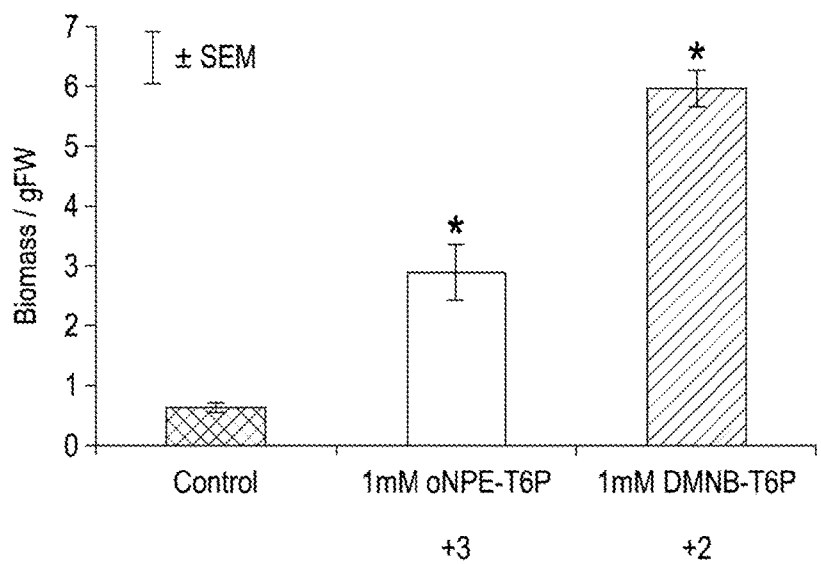
FIG. 43 shows the fresh weight biomass of regrowth. Asterisks indicate statistical significance.

In addition, regrowth (resurrection response) of new tissue from plants that had been cut back after drought treatment was higher in T6P precursor-treated plants (FIGS. 42 and 43). This demonstrates the capacity of T6P precursors to facilitate growth of new tissue (in the case of resurrection response) as well as salvage and grow new tissue (recovery response) in drought-treated plants. It should be noted that in all of these experiments, use of T6P solution alone gave identical results to use of water alone, consistent with the failure of T6P to enter into plants, further highlighting the success of the design principles for these signalling precursors.

The invention claimed is:

1. A method of increasing the yield of a drought stressed crop plant, the method comprising applying a compound to the plant, wherein the compound is of formula (I) or agriculturally acceptable salt thereof:

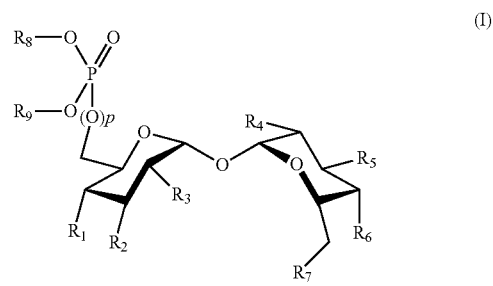

(I)

wherein;

p is 0 or 1;

$R_1$ to $R_7$ independently represent F, $N_3$, NR'R", $C_{1-4}$alkyl, —($C_{1-4}$alkyl)OH or OH, wherein R' and R" independently represent hydrogen or $C_{1-4}$alkyl;

and $R_8$ and $R_9$ are the same or different and represent H or a photo-labile protecting group, wherein at least one of $R_8$ and $R_9$ represents a photo-labile protecting group, and wherein the photo-labile protecting group is of formula (II):

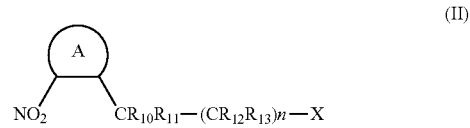

(II)

wherein;

ring A is selected from the group consisting of a $C_{6-10}$ aryl group, and a dibenzofuranyl ring, and further wherein the aryl group is unsubstituted or substituted with one or more substituents selected from $C_{1-4}$ alkyl, —OR', halogen, CN, —NR'R", —COOR', —($C_{1-4}$ alkyl) COOR' and —O($C_{1-4}$ alkyl)COOR', wherein R' and R" are independently selected from hydrogen and $C_{1-4}$ alkyl or wherein two adjacent ring positions of the $C_{6-10}$ aryl group are substituted with a —$CH_2$—O—$CH_2$ moiety;

either (i) $R_{10}$ and $R_{11}$ are the same or different and are selected from hydrogen, $C_{1-4}$alkyl which is unsubstituted or substituted with one or more halogen atoms, —OR', halogen, —NR'R" or —$CO_2R'$, wherein R' and R" are independently selected from hydrogen and $C_{1-4}$alkyl, or (ii) two $R_{10}$ groups on adjacent photo-labile protecting groups together form a bond and $R_{11}$ represents hydrogen, $C_{1-4}$alkyl which is unsubstituted or substituted with one or more halogen atoms, —OR', halogen, —NR'R" or —$CO_2R'$, wherein R' and R" are independently selected from hydrogen and $C_{1-4}$alkyl; n is 0 or 1; and $R_{12}$ and $R_{13}$ are the same or different and are selected from hydrogen, $C_{1-4}$alkyl which is unsubstituted or substituted with one or more halogen atoms, —OR', halogen, —NR'R" or —$CO_2R'$, wherein R' and R" are independently selected from hydrogen and $C_{1-4}$ alkyl; wherein X represents the link to the remainder of the compound of formula (I).

2. The method of claim 1, wherein the photo-labile group is selected from;

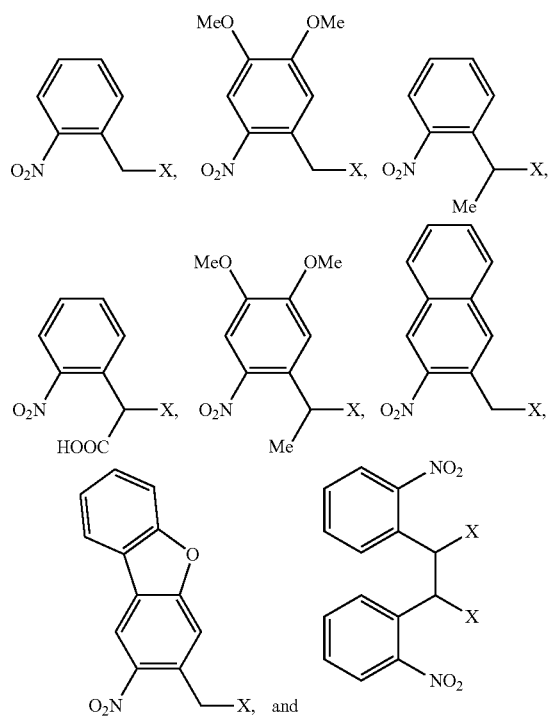

wherein X represents the link to the remainder of the compound of formula (I).

3. The method of claim 1, wherein the photo-labile protecting group is of formula (II) and ring A represents a $C_{6-10}$ aryl group or a dibenzofuranyl ring, wherein the aryl is unsubstituted or substituted with one or more substituents selected from $C_{1-4}$alkyl, —OR', halogen, CN, —NR'R", —COOR', —($C_{1-4}$alkyl)COOR', and —O($C_{1-4}$alkyl)COOR', wherein R' and R" are independently selected from hydrogen and $C_{1-4}$alkyl.

4. The method of claim 1, wherein the photo-labile protecting group is of formula (II) and ring A represents a phenyl, or naphthalenyl.

5. The method of claim 1, wherein the photo-labile protecting group is of formula (IIa):

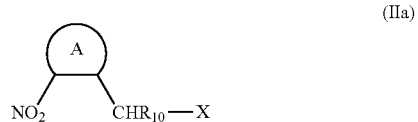

(IIa)

wherein; ring A represents an unsubstituted or substituted group selected from phenyl, naphthyl or dibenzofuranyl, wherein a substituted phenyl, naphthyl or dibenzofuranyl group is substituted with one or two methoxy substituents or wherein two adjacent ring positions are substituted with a —CH$_2$—O—CH$_2$— moiety; and the $R_{10}$ represents hydrogen, methyl, —CF3 or —COOH; wherein X represents the link to the remainder of the compound of formula (I).

6. The method of claim 1, wherein $R_1$ to $R_7$ represent hydroxyl.

7. The method of claim, wherein p is 1.

8. The method of claim 1, wherein the crop plant is a cereal crop selected from a genera selected from the group consisting of *Triticum, Zea, Oryza, Hordeum, Sorghum, Panicum, Avena*, and *Secale*.

9. The method of claim 1, wherein the compound of formula (I) is applied to the drought stressed plant at least 24 hours prior to re-watering the drought stressed plant.

10. The method of claim 1, wherein the drought stressed plant has been under drought stress prior to treatment for a period falling in the range of 8 hours to 10 days.

11. The method of claim 1, wherein the compound of formula (I) is applied to the drought stressed plant together with at least one fertilizer, fungicide, herbicide, insecticide or plant growth regulator.

12. The method of claim 1, wherein the drought stressed plant following treatment has increased growth, biomass and yield compared with corresponding untreated drought stressed plants.

* * * * *